United States Patent
Mazor et al.

(10) Patent No.: US 10,106,785 B2
(45) Date of Patent: Oct. 23, 2018

(54) ACETYLCHOLINESTERASE-FC DOMAIN FUSION PROTEIN

(71) Applicant: The Israel Institute of Biological Research (IIBR), Ness-Ziona (IL)

(72) Inventors: Ohad Mazor, Ness-Ziona (IL); Ofer Cohen, Netaim (IL); Tal Noy-Porat, Ness-Ziona (IL)

(73) Assignee: THE ISRAEL INSTITUTE OF BIOLOGICAL RESEARCH (IIBR), Ness-Ziona (IL)

( * ) Notice: Subject to any disclaimer, the term of this patent is extended or adjusted under 35 U.S.C. 154(b) by 0 days.

(21) Appl. No.: 15/089,738

(22) Filed: Apr. 4, 2016

(65) Prior Publication Data

US 2016/0289657 A1 Oct. 6, 2016

Related U.S. Application Data

(60) Provisional application No. 62/142,188, filed on Apr. 2, 2015.

(51) Int. Cl.
*C12N 9/18* (2006.01)
*A61K 38/00* (2006.01)

(52) U.S. Cl.
CPC ........ *C12N 9/18* (2013.01); *C12Y 301/01007* (2013.01); *A61K 38/00* (2013.01); *C07K 2319/30* (2013.01)

(58) Field of Classification Search
None
See application file for complete search history.

(56) References Cited

U.S. PATENT DOCUMENTS

2009/0249503 A1 10/2009 Rosendahl

FOREIGN PATENT DOCUMENTS

| WO | 02087624 A2 | 11/2002 | | |
|---|---|---|---|---|
| WO | 03061562 A2 | 7/2003 | | |
| WO | WO 2011005621 A1 * | 1/2011 | ....... | A61K 39/39591 |

OTHER PUBLICATIONS

Eddleston, M. "Management of acute organophosphorus Pesticide poisoning" Lancet (371): 597-607 (2008).
Raveh, L et al.,"Human Butyrylcholinesterase as a General Prophylactic Antidote for Nerve Agent Toxicity", Biochem. Pharmacol. (45) 2465-2474 (1993).
Cohen, O et al., "Comparison of Polyethylene Glycol-Conjugated Recombinant Human Acetylcholinesterase and Serum Human Butyrylcholinesterase as Bioscavengers of Organophosphate Compounds" Mol. Pharmacol. (70) 1121-1131 (2006).
Kronman, C. et al., "Production and secretion of high levels of recombinant human acetylcholinesterase in cultured cell lines: microheterogeneity of the catalytic subunit" Gene (121) 295-304 (1992).
Taylor et al. , "The structure of acetylcholinesterase: relationship to its function and cellular disposition" TINS (10) 93-95 (1987).
Czajkowsky, D. M. et al., "FC-Fusion Proteins: New Developments and Future Perspectives" EMBO Mol. Med. (4) 1015-1018 (2012).
Mazor, O. et al., " Aging-Resistant Organophosphate Bioscavenger Based on Polyethylene Glycol-Conjugated F338A Human Acetylcholinesterase" Mol Pharmacol. 74(3):755-63. (2008).
Ellman, G. L. et al., "A New and Rapid Colorimetric Determination of Acetylcholinesterase Activity" Biochem. Pharmacol. (7) 88-95. (1961).
Ordentlich, A. et al., "The Architecture of Human Acetylcholinesterase Active Center Probed by Interactions with Selected Organophosphate Inhibitors" J Biol. Chem. 271: 11953-11962 (1996).
Cohen, O. et al., "Effect of chemical modification of recombinant human acetylcholinesterase by polyethylene glycol on its circulatory longevity" , Biochem. J. (357) 795-802. (2001).

* cited by examiner

*Primary Examiner* — Brian Gangle

(74) *Attorney, Agent, or Firm* — Browdy and Neimark, PLLC

(57) ABSTRACT

Fusion polypeptides are provided including modified human Acetylcholinesterase conjugated to the Fc region of an immunoglobulin. Methods of preparing these polypeptide constructs and uses thereof as scavenging agents of organophosphate compounds are described.

17 Claims, 10 Drawing Sheets

Specification includes a Sequence Listing.

Fig. 1A

MDMRAHVHLLGLLLLWLPGAKCEGREDAELLVTVRGGRLRGIRLKTPGGPVSAFLGIPFAEPPMGPRR
FLPPEPKQPWSGVVDATTFQSVCYQYVDTLYPGFEGTEMWNPNRELSEDCLYLNVWTPYPRPTSPTP
VLVWIYGGGFYSGASSLDVYDGRFLVQAERTVLVSMNYRVGAFGFLALPGSREAPGNVGLLDQRLALQ
WVQENVAAFGGDPTSVTLFGESAGAASVGMHLLSPPSRGLFHRAVLQSGAPNGPWATVGMGEARR
RATQLAHLVGCPPGGTGGNDTELVACLRTRPAQVLVNHEWHVLPQESVFRFSFVPVVDGDFLSDTPEA
LINAGDFHGLQVLVGVVKDEGSYFLVYGAPGFSKDNESLISRAEFLAGVRVGVPQVSDLAAEAVVLHYT
DWLHPEDPARLREALSDVVGDHNVVCPVAQLAGRLAAQGARVYAYVFEHRASTLSWPLWMGVPHG
YEIEFIFGIPLDPSRNYTAEEKIFAQRLMRYWANFARTGDPNEPRDPKAPQWPPYTAGAQQYVSLDLRP
LEVRRGLRAQACAFWNRFLPKLLSATASEAPEPKSSDKTHTCPPCPAPELLGGPSVFLFPPKPKDTLMI
SRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK

Fig. 1B

EGREDAELLVTVRGGRLRGIRLKTPGGPVSAFLGIPFAEPPMGPRRFLPPEPKQPWSGVVDATTFQSVC
YQYVDTLYPGFEGTEMWNPNRELSEDCLYLNVWTPYPRPTSPTPVLVWIYGGGFYSGASSLDVYDGRF
LVQAERTVLVSMNYRVGAFGFLALPGSREAPGNVGLLDQRLALQWVQENVAAFGGDPTSVTLFGESA
GAASVGMHLLSPPSRGLFHRAVLQSGAPNGPWATVGMGEARRRATQLAHLVGCPPGGTGGNDTEL
VACLRTRPAQVLVNHEWHVLPQESVFRFSFVPVVDGDFLSDTPEALINAGDFHGLQVLVGVVKDEGSY
FLVYGAPGFSKDNESLISRAEFLAGVRVGVPQVSDLAAEAVVLHYTDWLHPEDPARLREALSDVVGDH
NVVCPVAQLAGRLAAQGARVYAYVFEHRASTLSWPLWMGVPHGYEIEFIFGIPLDPSRNYTAEEKIFAQ
RLMRYWANFARTGDPNEPRDPKAPQWPPYTAGAQQYVSLDLRPLEVRRGLRAQACAFWNRFLPKLL
SATASEAPEPKSSDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKL
TVDKSRWQQGNVFSCSVMHEALHNHYTQKSLSLSPGK

Figure 2

```
1-    atggacatgagggcccatgtgcaccttctggggctcctgctgctctggctgcccggggccaaatgtgagg
71-   gccgggaggatgcagagctgctggtgacggtgcgtgggggccggctgcggggcattcgcctgaagacccc
141-  cggggccctgtctctgctttcctgggcatccccttttgcggagccaccccatgggacccccgtcgctttctg
211-  ccaccggagcccaagcagccttggtcaggggtggtagacgctacaaccttccagagtgtctgctaccaat
281-  atgtggacacccctatacccaggttttgagggcaccgagatgtggaaccccaaccgtgagctgagcgagga
351-  ctgcctgtacctcaacgtgtggacaccataccccccgcctacatccccaccctgtcctcgtctggatc
421-  tatgggggtggcttctacagtggggcctcctccttggacgtgtacgatggccgcttcttggtacaggccg
491-  agaggactgtgctggtgtccatgaactaccgggtgggagcctttggcttcctggccctgccggggagccg
561-  agaggccccgggcaatgtgggtctcctggatcagaggctggccctgcagtgggtgcaggagaacgtggca
631-  gccttcggggggtgacccgacatcagtgacgctgtttggggagagcgcggggagccgcctcggtgggcatgc
701-  acctgctgtccccgcccagccggggcctgttccacagggccgtgctgcagagcggtgccccaatggacc
771-  ctgggccacggtgggcatgggagaggcccgtcgcagggccacgcagctggcccaccttgtgggctgtcct
841-  ccaggcggcactggtgggaatgacacagagctggtagcctgccttcggacacgaccagcgcaggtcctgg
911-  tgaaccacgaatggcacgtgctgcctcaagaaagcgtcttccggttctccttcgtgcctgtggtagatgg
981-  agacttcctcagtgacacccagaggccctcatcaacgcgggagacttccacggcctgcaggtgctggtg
1051- ggtgtggtgaaggatgagggctcgtattttctggtttacggggcccccaggcttcagcaaagacaacgagt
1121- ctctcatcagccgggccgagttcctggccggggtgcgggtcggggttccccaggtaagtgacctggcagc
1191- cgaggctgtggtcctgcattacacagactggctgcatcccgaggacccggcacgcctgagggaggccctg
1261- agcgatgtggtgggcgaccacaatgtcgtgtgccccgtggcccagctggctgggcgactggctgcccagg
1331- gtgcccgggtctacgcctacgtctttgaacaccgtgcttccacgctctcctggcccctgtggatggggt
1401- gccccacggctacgagatcgagttcatctttgggatccccctggaccccctctcgaaactacacggcagag
1471- gagaaaatcttcgcccagcgactgatgcgatactgggccaactttgcccgcacagggggatcccaatgagc
1541- cccgagaccccaaggccccacaatggcccccgtacacggcggggctcagcagtacgttagtctggacct
1611- gcggccgctggaggtgcggcggggctgcgcgcccaggcctgcgccttctggaaccgcttcctccccaaa
1681- ttgctcagcgccaCCgcctcggaggctcccgagcccaaatctagtgacaaaactcacacatgcccaccgt
1751- gcccagcacctgaactcctggggggaccgtcagtcttcctcttccccccaaaacccaaggacacctcat
1821- gatctcccggaccctgaggtcacatgcgtggtggtggacgtgagccacgaagaccctgaggtcaagttc
1891- aactggtacgtggacggcgtggaggtgcataatgccaagacaaagccacgggaggagcagtacaacagca
1961- cctaccgggtggtcagcgtcctcaccgtcctgcaccaggactggctgaatggcaaggagtacaagtgcaa
2031- ggtctccaacaaagccctcccagcccccatcgagaaaaccatctccaaagccaaagggcagccacgggaa
2101- ccacaggtttacacccctgccccatcccgcgaggagatgaccaagaaccaggtcagcctgacctgcctgg
2171- tcaaaggcttctatcccagcgacatcgccgtggagtgggagagcaatgggcagccgagaacaactacaa
2241- gaccaccctcccgtgctggactccgacggctccttcttcctctatagcaagctcaccgtggacaagagc
2311- aggtggcagcaggggaacgtcttctcatgctccgtgatgcacgaggctctgcacaaccactacacccaga
2381- agagcctctccctgtctccggtaaatga 2410
```

Figure 5A

1- ATGCGGCCGCCACAGTGCCTTCTGCATACCCCCAGCCTTGCCAGCCCT
51- CTGCTGCTGCTGCTGTTGTGGCTCCTGGGAGGTGGTGTTGGGGCGGAAGG
101- TCGAGACGACGCCGAGTTGCTGGTGACTGTCCGACGGGGACGGCTCCGGG
151- GAATCCGCCTCAAAACACCTGGGGGCCCCGTCTCTGCGTTTCTGGGCATC
201- CCTTTCGCAGAGCCACCCATGGGCCCCCGGAGATTCCTGCCCCCGGAACC
251- CAAACAGCCTTGGTCAGGGGTGGTCGATGCCACAACTTTCCAGAGCGTGT
301- GCTATCAGTACGTTGACACCTTGTATCCCGGATTTGAAGGCACTGACATG
351- TGGAACCCGAATCGAGAGCTGAGTGAGGACTGCCTGTATCTGAATGTGTG
401- GACCCCGTACCCTAGACCAACCTCACCCACCCCTGTTCTCGTGTGGATCT
451- ACGGGGGAGGTTTTTACTCTGGGGCCAGCTCCCTGGACGTGTATGATGGC
501- AGATTCCTGGTCCAGGCAGAACGGACAGTGCTCGTGAGTATGAATTATCG
551- GGTGGGCGCCTTCGGATTCTTGGCACTGCCCGGATCCCGGGAGGCCCCAG
601- GTAACGTGGGACTCCTCGACCAGCGCCTGGCTCTGCAGTGGGTGCAAGAA
651- AATGTAGCAGCGTTTGGTGGGGACCCAACCAGTGTGACTCTCTTTGGTGA
701- AAGCGCAGGGGCAGCTTCCGTGGGCATGCATCTGTTGTCACCACCATCTA
751- GGGGATTGTTCCACCGGGCTGTACTGCAGTCTGGAGCGCCAAATGGACCA
801- TGGGCCACAGTGGGGATGGGTGAAGCCAGACGGCGCGCCACCCAGCTGGC
851- ACATCTGGTGGGCTGCCCACCTGGGGGCACCGGAGGCAACGATACAGAAC
901- TGGTGGCCTGCCTTAGGACCCGCCCCGCTCAAGTCCTGGTGAATCACGAG
951- TGGCATGTGCTCCCTCAGGAAAGCGTGTTTCGGTTCTCATTCGTGCCCGT
1001- GGTGGATGGCGACTTTCTCAGCGACACACCCGAAGCGCTGATTAACGCCG
1051- GAGATTTCCATGGCCTCCAGGTTCTTGTGGGTGTCGTAAAGGACGAGGGG
1101- TCCTACTTCCTGGTTTATGGCGCGCCAGGCTTCTCTAAGGATAATGAGAG
1151- CTTGATCTCTCGCGCGGAGTTTTTGGCAGGCGTGCGCGTCGGCGTGCCTC
1201- AGGTTTCAGACTTGGCAGCCGAGGCCGTGGTCCTCCATTATACGGACTGG
1251- CTGCACCCGGAGGATCCTGCCAGACTTCGCGAAGCTCTGTCAGACGTGGT
1301- CGGAGACCATAATGTCGTGTGCCCCGTGGCTCAGTTGGCTGGGCGCCTCG
1351- CAGCCCAAGGCGCCAGGGTATATGCGTACGTTTTCGAGCACCGCGCCAGC
1401- ACACTCTCATGGCCTCTTTGGATGGGCGTGCCCCACGGGTATGAAATCGA
1451- GTTCATATTCGGCATCCCTCTGGATCCATCCAGAAACTACACCGCCGAAG
1501- AGAAGATCTTCGCCCAGAGATTGATGAGATACTGGGCCAACTTTGCTCGG

Figure 5B

1551- ACCGGTGACCCTAACGAGCCCAGAGACCCGAAGGCTCCCCAGTGGCCTCC
1601- TTATACCGCGGGTGCACAGCAGTACGTAAGCCTGGACCTGAGACCACTGG
1651- AGGTGCGACGCGGACTGCGAGCACAGGCCTGCGCCTTTTGGAATCGGTTC
1701- CTCCCCAAGCTGTTGTCAGCCACCGCATCCGAAGCCCCCGAGCCCAAATC
1751- TAGTGACAAAACTCACACATGCCCACCGTGCCCAGCACCTGAACTCCTGG
1801- GGGGACCGTCAGTCTTCCTCTTCCCCCCAAAACCCAAGGACACCCTCATG
1851- ATCTCCCGGACCCCTGAGGTCACATGCGTGGTGGTGGACGTGAGCCACGA
1901- AGACCCTGAGGTCAAGTTCAACTGGTACGTGGACGGCGTGGAGGTGCATA
1951- ATGCCAAGACAAAGCCACGGGAGGAGCAGTACAACAGCACCTACCGGGTG
2001- GTCAGCGTCCTCACCGTCCTGCACCAGGACTGGCTGAATGGCAAGGAGTA
2051- CAAGTGCAAGGTCTCCAACAAAGCCCTCCCAGCCCCCATCGAGAAAACCA
2101- TCTCCAAAGCCAAAGGGCAGCCACGGGAACCACAGGTTTACACCCTGCCC
2151- CCATCCCGCGAGGAGATGACCAAGAACCAGGTCAGCCTGACCTGCCTGGT
2201- CAAAGGCTTCTATCCCAGCGACATCGCCGTGGAGTGGGAGAGCAATGGGC
2251- AGCCCGAGAACAACTACAAGACCACCCCTCCCGTGCTGGACTCCGACGGC
2301- TCCTTCTTCCTCTATAGCAAGCTCACCGTGGACAAGAGCAGGTGGCAGCA
2351- GGGGAACGTCTTCTCATGCTCCGTGATGCACGAGGCTCTGCACAACCACT
2401- ACACCCAGAAGAGCCTCTCCCTGTCTCCCGGTAAATGA

ACETYLCHOLINESTERASE-FC DOMAIN FUSION PROTEIN

The Sequence Listing in ASCII text file format of 70,213 bytes in size, created on Oct. 25, 2017, with the file name "2017-10-25SequenceListing_MAZOR2A," filed in the U.S. Patent and Trademark Office on Oct. 25, 2017, is hereby incorporated herein by reference.

TECHNOLOGICAL FIELD

The present invention generally relates to fusion polypeptides comprising fragments of human Acetylcholinesterase conjugated to the Fc region of an immunoglobulin. The present invention also relates to methods of preparing these polypeptide constructs and to uses thereof as scavenging agents of organophosphate compounds.

BACKGROUND ART

References considered to be relevant as background to the presently disclosed subject matter are listed below:
[1] Eddleston, M. 2008, Lancet (371): 597-607
[2] Raveh, L et al., 1993, Biochem. Pharmacol. (45) 2465-2474
[3] Cohen, O et al., 2006, Mol. Pharmacol. (70) 1121-1131
[4] WO 02/087624
[5] US 2009/0249503
[6] WO 03/061562
[7] Kronman, C. et al., 1992, Gene (121) 295-304
[8] Taylor et al. 1987, TINS (10) 93-95
[9] Czajkowsky, D. M. et al., 2012, EMBO Mol. Med. (4) 1015-1018
[10] Mazor, O. et al., 2008, Mol Pharmacol. 74(3):755-63.
[11] Ellman, G. L. et al., 1961, Biochem. Pharmacol. (7) 88-95.
[12] Ordentlich, A. et al., 1996, J Biol. Chem. 271: 11953-11962.
[13] Cohen, O. et al., 2001, Biochem. J. (357) 795-802.

Acknowledgement of the above references herein is not to be inferred as meaning that these are in any way relevant to the patentability of the presently disclosed subject matter.

BACKGROUND

Organophosphorus (OP) compounds are a diverse group of chemicals that include, among others, insecticides, antihelmintics (drugs that are used for killing parasitic worms) and nerve gases.

Organophosphates inhibit the enzyme acetylcholinesterase (AChE) by phosphorylating the serine hydroxyl residue in the AChE active site. AChE is critical for nerve function, so the irreversible blockage of this enzyme upon exposure to organophosphates (OP poisoning), causes acetylcholine accumulation, and results in muscle overstimulation that may lead to death.

An arsenal of OP compounds was developed as chemical warfare agents, for example tabun, sarin, soman and agent VX. In addition to the warfare context, organophosphorus pesticide self-poisoning is also a serious clinical problem in rural regions of the developing world, and kills an estimated 200,000 people every year (1).

Current treatment of OP poisoning includes a pretreatment with carbamates to protect AChE from inhibition by OP compounds and post-exposure treatments with anti-cholinergic drugs that act to counteract the effects of excess acetylcholine and reactivate AChE. While some OP poisoning antidotes are effective at preventing lethality from OP poisoning, current treatment lacks the ability to prevent post-exposure incapacitation, performance deficits, or permanent brain damage.

Choline esterases, such as AChE or Butyrylcholinesterase (BChE), were used for development of OP scavengers. Such enzyme scavengers are being developed as a pretreatment to sequester highly toxic OPs before they can reach their physiological targets and prevent the toxic effects from occurring (2, 3).

Since recombinant choline esterases have short half lives in the circulation system, with a mean retention time of 60 minutes (3), various conjugates of choline esterases were developed for preventing their rapid clearance from the circulation. For example, the publication WO 02/087624 (4) describes a circulatory long-lived cholinesterase, which is coupled with a non-antigenic polymer.

Cholinesterases which are covalently fused to another protein that naturally has a long circulating half-life (including human IgG1) were described for example in US 2009/0249503 (5) and in WO 03/061562 (6).

GENERAL DESCRIPTION

In a first of its aspects, the present invention provides a fusion polypeptide comprising:
  (a) an acetylcholinesterase (AChE) polypeptide component comprising a modified human AChE polypeptide having an amino acid sequence denoted by SEQ ID NO: 8 or variants thereof; and
  (b) a fragment crystallizable (Fc) domain of human IgG or variants thereof, wherein the fusion polypeptide retains the functional activity of human AChE.

In one embodiment, said AChE polypeptide component is covalently linked through its C-terminus to said Fc domain.

In another embodiment, said AChE polypeptide component is covalently linked through its N-terminus to said Fc domain.

In certain embodiments, said Fc domain of human IgG is an Fc domain of IgG1 or of IgG2.

In certain specific embodiments, said Fc domain comprises an amino acid sequence that is at least 70% identical to the amino acid sequence denoted by SEQ ID NO: 15 and wherein said Fc domain retains its functional activity.

In one embodiment, said fusion polypeptide comprises a dimer of two identical monomers, wherein each one of the identical monomers comprises an acetylcholinesterase (AChE) polypeptide component and an Fc domain of human IgG.

In another embodiment, said fusion polypeptide comprises a dimer of a first and second monomers, wherein said first monomer comprises an AChE polypeptide component and an Fc domain of human IgG and the second monomer comprises an Fc domain of human IgG.

In certain embodiments, said fusion polypeptide further comprises a spacer covalently linking the AChE polypeptide component and the Fc domain.

In one specific embodiment, said spacer comprises the amino acid sequence ASEAP denoted by SEQ ID NO: 9.

In one specific embodiment, said spacer consists of the amino acid sequence ASEAP denoted by SEQ ID NO: 9.

In one embodiment, said modified human AChE polypeptide comprises an amino acid sequence that is at least 70% identical to the amino acid sequence denoted by SEQ ID NO: 8 and wherein said human AChE polypeptide component retains the functional activity of human AChE.

In other embodiments, said modified human AChE polypeptide comprises an amino acid substitution in at least one position of SEQ ID NO: 8 and wherein said human AChE polypeptide component retains the functional activity of human AChE.

In a specific embodiment, said modified human AChE polypeptide comprises the amino acid Ala at a position corresponding to position 338 of the amino acid sequence denoted by SEQ ID NO: 8.

In another specific embodiment, said modified human AChE polypeptide consists of the amino acid sequence denoted by SEQ ID NO: 8.

In another specific embodiment, said fusion polypeptide comprises the amino acid sequence denoted by SEQ ID NO: 17.

In another specific embodiment, said fusion polypeptide consists of the amino acid sequence denoted by SEQ ID NO: 17.

In another one of its aspects, the present invention provides an isolated nucleic acid construct comprising a nucleic acid sequence encoding the fusion polypeptide of the invention.

In one embodiment, said nucleic acid construct further comprises a sequence encoding a secretion signal situated at the 5' end of said nucleic acid sequence.

In a specific embodiment, said secretion signal is a kappa-leader sequence having the amino acid sequence denoted by SEQ ID NO: 11 or the native signal peptide of human AChE having the amino acid sequence denoted by SEQ ID NO: 12.

In another specific embodiment, said nucleic acid construct is of the nucleic acid sequence denoted by SEQ ID NO: 18 or by SEQ ID NO: 19.

The invention also provides an expression vector comprising the isolated nucleic acid construct of the invention, as well as an isolated host cell comprising the nucleic acid construct or the expression vector as described above.

In another one of its aspects, the present invention provides a method of producing the fusion polypeptide of the invention, comprising culturing the host cell under conditions suitable for expression of the fusion polypeptide in the host cell and recovering the fusion polypeptide thereby produced.

In another aspect, the present invention provides a pharmaceutical composition comprising the fusion polypeptide of the invention and a pharmaceutically acceptable carrier.

In certain embodiments, said pharmaceutical composition further comprises an additional therapeutic agent.

In another aspect, the fusion polypeptide of the invention, or the pharmaceutical composition of the invention are for use in prophylaxis of organophosphate poisoning.

In another aspect, the present invention provides a method of prophylaxis of organophosphate poisoning comprising administering an effective amount of the fusion polypeptide or the pharmaceutical composition of the invention to a patient in need thereof.

In one embodiment, said method further comprises administering at least one additional therapeutic agent.

In certain embodiments, said at least one additional therapeutic agent is selected from atropine, glycopyrrolate, benzodiazepines, pralidoxime and native (non-fused) cholinesterase(s).

In one specific embodiment, said additional therapeutic agent is administered after exposure to organophosphate poisoning.

In another one of its aspects, the invention provides a method of increasing the circulatory half-life of AChE, said method comprising preparing a fusion polypeptide comprising:
(a) an acetylcholinesterase (AChE) polypeptide component comprising a modified human AChE polypeptide having an amino acid sequence denoted by SEQ ID NO: 8 or variants thereof; and
(b) a fragment crystallizable (Fc) domain of human IgG, or variants thereof wherein the human AChE polypeptide component retains the functional activity of human AChE.

In still another one of its aspects, the invention provides a kit comprising:
(i) at least one fusion polypeptide comprising:
(a) an acetylcholinesterase (AChE) polypeptide component comprising a modified human AChE polypeptide having an amino acid sequence denoted by SEQ ID NO: 8 or variants thereof; and
(b) a fragment crystallizable (Fc) domain of human IgG or variants thereof, wherein the fusion polypeptide retains the functional activity of human AChE; and
(ii) instructions for use.

In some embodiments the kit further comprises at least one additional therapeutic agent.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A-FIG. 1B show the amino acid sequence of the AChE-Fc fusion protein (SEQ ID NO:22, also termed herein the "NL1 fusion protein") with an intact Kappa-leader sequence (FIG. 1A) and after cleavage of the leader sequence (FIG. 1B; SEQ ID NO. 23). Underlined letters represent the Kappa-leader sequence, grey letters represent the modified AchE sequence, grey boxed letters (ASEAP) represent the spacer and bold letters represent the Fc portion comprised of hinge, CH2 and CH3 domains.

FIG. 2 shows the nucleotide sequence (SEQ ID NO:24) encoding the NL1 fusion protein, comprising the Kappa-leader sequence. Underlined letters represent the Kappa-leader sequence, grey letters represent the modified AChE sequence, grey boxed letters represent the spacer and bold letters represent the Fc portion comprised of hinge, CH2 and CH3 domains.

FIGS. 5A and 5B show the nucleotide sequence (SEQ ID NO:25) encoding the NL1 fusion protein comprising the native signal peptide of AChE. Underlined letters represent the native signal peptide of AChE, grey letters represent the modified AChE sequence, grey boxed letters represent the spacer and bold letters represent the Fc portion.

DETAILED DESCRIPTION OF EMBODIMENTS

Figure 3:
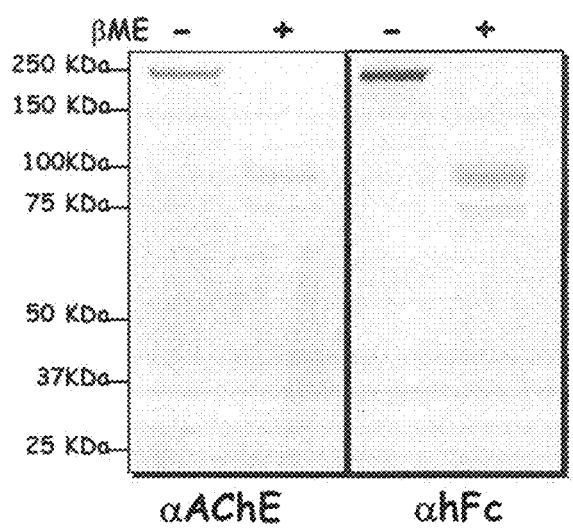
FIG. 3 shows a Western blot analysis of NL1 fusion protein preparations, performed in the absence and in the presence of β-mercaptoethanol while using either an antibody directed to AChE (left panel) or an antibody directed to human Fc (right panel), confirming that NL1 consist of both AChE and Fc and that the protein is present as a dimer.

The present invention is based on the construction of a chimeric recombinant molecule of human acetylcholinesterase (AChE) coupled to the Fc region of human IgG1 (also termed herein AChE-Fc fusion protein) that is compatible with biotechnological production and purification, maintains the catalytic activity of the human AChE enzyme and has a significantly longer half-life as compared to the half-life of free human AChE.

The novel fusion product was shown to have a bioscavenging reactivity toward the organophosphate-AChE inhibitors BW284c5, propidium, soman and VX. Owing to the ease of production, reactivity toward nerve agents and its optimized pharmacokinetics characteristics, AChE-Fc emerges as a promising next-generation bioscavenger.

The present invention thus provides a fusion polypeptide comprising:

(a) an acetylcholinesterase (AChE) polypeptide component comprising a modified human AChE polypeptide having an amino acid sequence denoted by SEQ ID NO: 8 or variants thereof; and (b) a fragment crystallizable (Fc) domain of human IgG or variants thereof;

wherein the AChE polypeptide component retains the functional activity of human AChE.

Acetylcholinesterase is an enzyme of cardinal importance in neurotransmission systems, and is responsible for rapid termination of impulse transmission at cholinergic synapses by hydrolysis of the neurotransmitter acetylcholine (7). Acetylcholinesterase is a primary target of inhibition by organophosphorus compounds.

Thus the term "acetylcholinesterase" (also termed AChE, acetylhydrolase or EC 3.1.1.7) as herein defined, refers to an enzyme that hydrolyzes the neurotransmitter acetylcholine. The amino acid sequence of human acetylcholinesterase is denoted for example by SEQ ID NO: 21.

As described below, an N-terminal and C-terminal truncated version of human AChE was prepared for use in conjugation. This truncated version lacks both the N and C termini of the full length human AChE, namely the native signal sequence of AChE and the C-terminal 40 amino acids of the AChE "tail". The resulting truncated polypeptide is termed herein "modified human AChE" or "modified AChE".

It was previously reported that the full length human AChE may assemble into tertramers of catalytic subunits that are disulfide-linked to a filamentous tail unit, which is remote from the AChE catalytic subunit (8). In order to circumvent the formation of AChE-Fc conjugate multi-polypeptide complexes, the tail unit of the full length human AChE was deleted, as detailed below. As shown for example in FIG. 7, deletion of the tail unit did not affect the catalytic activity of the AChE polypeptide component.

Thus the term "AChE enzyme tail" as used herein refers to the unit that forms a collagen-like structure at the C-terminal end of the AChE polypeptide, distal to the catalytic subunit. For example, the term AChE enzyme tail refers to amino acid residues DTLDEAERQWKAEFHRWSSYM-VHWKNQFDHYSKQDRCSDL at positions 575 to 614 (in the N- to C-terminus direction) in the sequence of full length human AChE denoted by SEQ ID NO: 21 (Table 2 below).

Therefore, the term "modified human AChE" (also referred to herein as "modified AChE") as used herein refers to a polypeptide fragment of the full length human AChE enzyme, which lacks the N-terminal signal peptide and at least 4 amino acid residues at the C-terminal tail of the full length human AChE enzyme. In certain embodiments the modified AchE enzyme lacks the N-terminal signal peptide and between about 4 and about 40 amino acid residues at the C-terminal tail of the full length human AChE enzyme. In a specific embodiment, the modified AchE enzyme lacks the N-terminal signal peptide and 40 amino acid residues at the C-terminal tail of the full length human AChE enzyme.

In some embodiments the amino acid sequence of the modified human AChE polypeptide as herein defined is denoted by SEQ ID NO: 8. Methods for preparing the modified human AChE polypeptide as herein defined based on the disclosed amino acid sequence thereof are well known in the art. For example, the modified human AChE polypeptide as herein defined may be prepared as described in Example 1 below. The modified AChE as well as the fusion polypeptide comprising the modified AChE retain the functional activity of human AChE.

The high reactivity of acetylcholinesterase towards Organophosphorus (OP) compounds renders exogenous acetylcholinesterase an effective scavenging agent in the prophylaxis of OP-poisoning. However, the use of acetylcholinesterase as a scavenging agent in the prophylaxis of OP-poisoning depends on the retention of the enzyme in the circulation for sufficiently long periods of time. As indicated above, recombinant choline esterases have rather short half lives in the circulation system, with a mean retention time of 60 minutes (3, 7).

As demonstrated in appended FIG. 9 and in Table 3 below, the AChE half-life was significantly longer when fused to a fragment crystallizable (Fc) domain of human IgG, compared to the half-life of free AChE, with a half-life of about 4000 minutes and a mean retention time (MRT) of about 5800 minutes as compared to the half life and MRT of about 29 and 40 minutes, respectively, of free AChE. It should be appreciated that by the term "free AChE" it is meant human (native) AchE that is not conjugated to another polypeptide.

Thus, as indicated above, the present invention provides a fusion polypeptide comprising an AChE polypeptide component (element) comprising a modified human AChE polypeptide and a fragment crystallizable (Fc) domain of human IgG.

The term "fusion polypeptide" in the context of the present invention concerns a sequence of amino acids, predominantly (but not necessarily) connected to each other by peptidic bonds. The term "fused" in accordance with the fusion polypeptide of the present invention refers to the fact that the amino acid sequences of at least two different origins, namely, the modified AChE as herein defined and the Fc domain of human IgG, are linked to each other by covalent bonds either directly or via an amino acid linker or spacer, joining (bridging, conjugating, covalently binding) the amino acid sequences. The fusion may be performed by chemical conjugation or by genetic engineering methods that are well known in the art, for example using the procedure to described below.

The term "polypeptide" as used herein refers to amino acid residues, connected by peptide bonds. A polypeptide sequence is generally reported from the N-terminal end containing free amino group to the C-terminal end containing free carboxyl group. A polypeptide may also be termed amino acid sequence, peptide, or protein and can be modified, for example, by manosylation, glycosylation, amidation, carboxylation or phosphorylation.

By the term "covalently linked" or "covalently linking" it is meant that the indicated domains are connected or linked by covalent bonds.

Fusion polypeptides based on the fragment crystallizable (Fc) domain of human IgG (Fc) are composed of an immunoglobulin Fc domain that is directly or indirectly linked to another peptide. It was previously reported that the presence of the Fc domain markedly increases the plasma half-life of the resulting fusion polypeptide, owing to its interaction with the salvage neonatal Fc-receptor (9). In the present invention, the Fc domain is directly or indirectly linked to the modified AChE.

In some embodiments the AChE polypeptide component as herein defined is covalently linked through its C-terminus to the Fc domain of human IgG. Namely, in some embodiments, in the N- to C-terminal direction, the fusion polypeptide according to the invention comprises the AChE polypeptide component and the Fc domain component.

In other embodiments the AChE polypeptide component as herein defined is covalently linked through its N-terminus to the Fc domain of human IgG. Namely, in some embodiments, in the N- to C-terminal direction, the fusion polypeptide of the invention comprises the Fc domain component and the AChE polypeptide component.

The term "fragment crystallizable (Fc) domain" (or Fc fragment) of human immunoglobulins G (IgG) as herein defined refers to the tail region of a human IgG antibody and encompasses native Fc and Fc variant molecules and sequences as defined herein below.

Human immunoglobulins are a group of structurally and functionally similar glycoproteins that confer humoral immunity in humans. As known in the art, the immunoglobulin protein "backbone" consists of two identical "heavy" and two identical "light" chains. Five classes of immunoglobulins (IgG, IgA, IgM, IgD, and IgE) have been distinguished. Human IgG subclasses are glycoproteins composed of two heavy and two light chains linked together by inter-chain disulfide bonds. The human IgG subclasses are further divided to IgG 1, 2, 3 and 4, which differ one from the other in their hinge region.

The term "Fc domain" includes molecules in a monomeric or a dimeric form (for example as in Immunoglobulin G) that may be digested from a whole antibody or produced by other means. In structural terms, the term Fc refers to a polypeptide that includes the hinge region, the heavy chain constant region 2 (CH2 domain) and the heavy chain constant region 3 (CH3 domain) of an immunoglobulin in an N-terminal to C-terminal direction.

In specific embodiments the Fc domain of human IgG is a monomeric polypeptide comprising the hinge region, the heavy chain constant region 2 (CH2 domain) and the heavy chain constant region 3 (CH3 domain) of an immunoglobulin in the N-terminal to C-terminal direction.

In some embodiments, the Fc domain is a native Fc domain of human IgG.

The term "native Fc" refers to a molecule or sequence comprising the amino acid sequence of a non-antigen-binding fragment resulting from digestion of a whole IgG antibody, whether in monomeric or dimeric form, at which a peptide may be added or conjugated by being covalently bound, directly or indirectly through a linker or a spacer, to the hinge region of the Fc domain of human IgG.

In some embodiments the fusion polypeptide according to the invention is wherein the Fc domain of human IgG is an Fc domain of IgG1 or of IgG2.

As indicated above, the present invention also encompasses variants of the modified AChE and variants of the Fc domain of human IgG.

By the term "variant" it is meant sequences of amino acids or nucleotides that are different from the sequences specifically identified herein, in which one or more amino acid residues or nucleotides are deleted, substituted or added, without affecting the functional activity of the original molecule (for example the functional activity of the human AChE or the functional activity of the Fc domain).

It should be appreciated that by the term "added", as used herein it is meant any addition(s) of amino acid residues to the sequences described herein. For example, the variant antibodies of the invention may be extended at their N-terminus and/or C-terminus with various identical or different amino acid residues.

Variants also encompass various amino acid substitutions. An amino acid "substitution" is the result of replacing one amino acid with another amino acid which has similar or different structural and/or chemical properties Amino acid substitutions may be made on the basis of similarity in polarity, charge, solubility, hydrophobicity, hydrophilicity, and/or the amphipathic nature of the residues involved.

Variants also encompass conservative amino acid substitutions. Conservative substitution tables providing functionally similar amino acids are well known in the art. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Conservative nucleic acid substitutions are nucleic acid substitutions resulting in conservative amino acid substitutions as defined above.

As used herein, the term "amino acid" or "amino acid residue" refers to naturally occurring and synthetic amino acids, as well as amino acid analogs and amino acid mimetics that function in a manner similar to the naturally occurring amino acids.

Variant sequences refer to amino acid or nucleic acid sequences that may be characterized by the percentage of the identity of their amino acid or nucleotide sequences to the amino acid or nucleotide sequences described herein (namely the amino acid sequence of or the nucleotide sequence encoding the modified AChE and Fc domain herein described).

In some embodiments, variant sequences as herein defined refer to nucleic acid sequences that encode the polypeptides as herein defined (namely the modified AChE or the Fc domain of human IgG), each having a sequence of nucleotides with at least 70% or 75% of sequence identity, around 80% or 85% of sequence identity, around 90%, 91%, 92%, 93%, 94%, 95%, 96%, 97%, 98% or 99% of sequence identity when compared to the nucleic acid sequences that encode the modified AChE or the Fc domain of human IgG described herein.

In some embodiments, variant sequences as herein defined refer to the amino acid sequences of the polypeptides as herein defined (namely the modified AChE or the Fc domain of human IgG), each having a sequence of amino acid residues with at least 70% or 75% of sequence identity, around 80% or 85% of sequence identity, around 90%, 91%, 92%, 93%, 94%, 95%, 96%, 97%, 98% or 99% of sequence identity when compared to the amino acid sequences of the modified AChE or the Fc domain of human IgG described herein.

In some embodiments the modified human AChE polypeptide as herein defined comprises an amino acid sequence that is at least 70% identical to the amino acid sequence denoted by SEQ ID NO: 8, wherein said human AChE polypeptide component retains the functional activity of human AChE.

In other embodiments the modified human AChE polypeptide as herein defined comprises an amino acid substitution in at least one position of SEQ ID NO: 8, wherein said human AChE polypeptide component retains the functional activity of human AChE.

An aging-resistant organophosphate bioscavenger based on polyethylene glycol-conjugated F338A human Acetylcholinesterase was previously reported (10). Therefore in further embodiments the modified human AChE polypeptide as herein defined comprises the amino acid Ala at a position corresponding to position 338 of the amino acid sequence denoted by SEQ ID NO: 8. In other words, in specific embodiments the amino acid Ala replaces the amino acid Phe at position 338 of the amino acid sequence denoted by SEQ ID NO: 8.

In yet further embodiments the modified human AChE polypeptide as herein defined consists of the amino acid sequence denoted by SEQ ID NO: 8.

By the term "the AChE polypeptide component retains the functional activity of human AChE" it is meant that the fusion polypeptide as herein defined is capable of hydrolyzing acetylcholine to a level comparable to that of human AChE. In other words, by this term it is meant that the fusion polypeptide as herein defined maintains to cholinesterase activity of free human AChE. Assays for determining cholinesterase activity are well known in the art. For example, the functional activity of fusion polypeptides prepared as herein described may be determined by an ELISA assay using Acetyl-thio-cholin (ATC) as substrate, as exemplified below, while comparing the enzymatic activity of the fusion polypeptide described herein to that of free human AChE.

By the term "a level comparable to that of human AChE" it is meant that the fusion polypeptides as herein defined retains at least 50, 55, 60, 65, 70, 75, 80, 85, 90, 95 or 100% of the functional activity of free human AChE acetylcholine.

As indicated above, the Fc domain of human IgG also encompasses Fc variants of the Fc domain of human IgG.

The term "Fc variant" refers to a molecule or sequence that is modified from a native Fc but still comprises a binding site for the salvage receptor, FcRn. In some embodiments the term "Fc variant" encompasses a molecule or sequence that is humanized from a native Fc domain of a non-human IgG. The term "Fc variant" also contemplates a molecule or sequence that lacks one or more native Fc sites or residues that affect or are involved in (i) disulfide bond formation, (ii) incompatibility with a selected host cell (iii) N-terminal heterogeneity upon expression in a selected host cell, (iv) glycosylation, (v) interaction with complement, (vi) binding to an Fc receptor other than a salvage receptor, or (vii) antibody-dependent cellular cytotoxicity (ADCC).

Determining whether an Fc variant still comprises a binding site for the salvage receptor, FcRn may be performed by methods known to a person skilled in the art, for example by measuring its binding to recombinant FcRn molecules using ELISA, Octet or surface plasmon resonance (SPR).

In some embodiments the fusion polypeptide according to the invention is wherein the Fc domain comprises an amino acid sequence that is at least 70% identical to the amino acid sequence denoted by SEQ ID NO: 15 and wherein said Fc domain retains its functional activity (namely its binding to the salvage receptor).

As demonstrated by FIG. 3, under non-reducing conditions, the fusion polypeptide prepared as described below migrated as a 250 KDa polypeptide, which apparently, without wishing to be bound by theory, forms a dimer of two identical monomers, each of which independently comprising a modified AChE component and an Fc domain.

Thus the fusion polypeptide according to the invention forms a dimer of two identical or different monomers, obtained by expression of the polypeptides as monomers that subsequently form stable dimers by non-covalent interactions. Thereby, a structure that is similar to the structural configuration of an antibody is obtained. A schematic presentation of a dimer of two identical monomers, where each one of the monomers comprises both the AChE and the Fc domain components, is demonstrated in FIG. 4.

In some embodiments, the fusion polypeptide according to the invention is wherein said fusion polypeptide comprises a dimer of two identical monomers, wherein each one of the identical monomers comprises an acetylcholinesterase (AChE) polypeptide component and an Fc domain of human IgG.

The fusion polypeptide according to the invention in the form of a dimer of two identical monomers may be prepared using any method known in the art, for example, as detailed below.

While it is essential that the Fc domain will be configured in a dimeric form, the AChE polypeptide component may reside in the resulting fusion protein as a monomer.

Therefore in other embodiments the fusion polypeptide according to the invention is wherein said fusion polypeptide as herein defined comprises a dimer of a first monomer and a second monomer, wherein said first monomer comprises an AChE polypeptide component and an Fc domain of human IgG and the second monomer comprises an Fc domain of human IgG.

The fusion polypeptide according to the invention comprising a dimer in which the first monomer comprises an AChE polypeptide component and an Fc domain of human IgG and the second monomer comprises an Fc domain of human IgG may be prepared by expressing the fusion polypeptide according to the invention alongside with a free Fc (in the same host cell), allowing the formation of a protein consisting of two FC arms with one AChE covalently linked to one of the arms.

As indicated above, the present invention provides a fusion polypeptide in which the AChE polypeptide component and the Fc domain of human IgG are linked to each other by covalent bonds either directly or via an amino acid linker or spacer. In other words, the fusion polypeptide in the context of the present invention may also optionally comprise at least one linker or spacer covalently joining the different domains of the polypeptide protein construct.

Therefore in some embodiments the fusion polypeptide according to the invention further comprises a spacer covalently linking the AChE polypeptide component and the Fc domain of human IgG.

The term "spacer" in the context of the invention concerns an amino acid sequence of from about 4 to about 20 amino acid residues positioned between the modified AChE and the Fc domain of human IgG and covalently joining them together. For example, a spacer in accordance with the invention may be 4, 5, 6, 7, 8, 9, 10, 11, 12, 13, 14, 15, 16, 17, 18, 19 or 20 amino acids long. Spacers are often composed of flexible amino acid residues, for example but not limited to glycine and serine so that the adjacent protein domains are free to move relative to one another. The term "spacer" can be interchangeably used with the term "linker".

The design of a spacer that enables proper folding of the various domains of a protein is well known in the art. A non-binding example of a spacer is the amino acid sequence ASEAP (Ala-Ser-Glu-Ala-Pro) as denoted by SEQ ID NO. 9. This sequence was used in the Examples below to construct the fusion proteins. An additional example for a spacer that may be used in accordance with the invention is the spacer GGGSxn (where n can be 1, 2, 3, 4 or 5 depending on the desired linker length; corresponding to residues 1-4, residues 1-8, residues 1-12, residues 1-16, and residues 1-10 of SEQ ID NO:26, respectively).

The use of a spacer or a linker is optional and not mandatory. In the present invention, a spacer having the amino acid sequence ASEAP (denoted by SEQ ID NO: 9) was added to the C terminus of the modified human AChE polypeptide, thereby replacing the "tail unit" of AChE, in order to facilitate the secretion of AChE.

Therefore in some embodiments the spacer as herein defined comprises the amino acid sequence ASEAP denoted by SEQ ID NO: 9. In other embodiments the spacer as herein defined consists of the amino acid sequence ASEAP denoted by SEQ ID NO: 9.

In fact, when the modified human AChE polypeptide is linked to the Fc domain through the C-terminal end of modified AChE, a spacer is less needed since the hinge region of the Fc domain serves as a flexible linker. However, when the modified human AChE polypeptide is fused to the Fc domain through the N-terminal end of modified AChE, a longer linker will be necessary in order to obtain a more flexible fusion polypeptide.

In some further embodiments the spacer as herein defined is of the amino acid sequence GGGSxn (wherein n can be 1, 2, 3, 4 or 5 depending on the desired linker length; corresponding to residues 1-4, residues 1-8, residues 1-12, residues 1-16, and residues 1-10 of SEQ ID NO:26, respectively).

In specific embodiments the fusion polypeptide as herein defined comprises, in the N- to C terminus direction, an acetylcholinesterase (AChE) polypeptide component (or variant thereof), a spacer and an Fc domain of human IgG (or variant thereof). Such fusion protein may be prepared as detailed below and is schematically presented in FIG. 4.

As shown in Example 3, a fusion polypeptide comprising the modified human AChE polypeptide, the spacer ASEAP and the Fc domain of human IgG was active, based on its ability to hydrolyze the Acetyl-thio-cholin (ATC) substrate (FIG. 7). In addition, as shown in Example 4, the above fusion polypeptide and free AChE shared similar kinetic hydrolysis parameters towards ATC (Table 4).

Therefore in some specific embodiments the fusion polypeptide according to the invention comprises the amino acid sequence denoted by SEQ ID NO: 17.

In other specific embodiments the fusion polypeptide according to the invention consists of the amino acid sequence denoted by SEQ ID NO: 17.

In some embodiments the fusion polypeptide according to the present invention is an isolated or purified fusion polypeptide.

In another one of its aspects, the present invention provides an isolated nucleic acid construct comprising a nucleic acid sequence encoding the fusion polypeptide according to the invention. One of skill will appreciate that, utilizing the sequence information provided for the various regions of the fusion polypeptide as herein defined, nucleic acids encoding these sequences may be obtained using any methods well known in the art. For example nucleic acids constructs in accordance with the present invention may be prepared using the recombinant procedures described below.

The isolated nucleic acid constructs according to the invention may further comprise additional elements, for example promoters, regulatory and control elements (for example a signal peptide or a leader peptide), translation, expression and other signals, operably linked to the nucleic acid sequence encoding the fusion polypeptide of the invention.

By the term "operably linked" is meant that a nucleic acid sequence and a regulatory sequence(s) are connected in such a way as to permit gene expression when the appropriate molecules (e.g., transcriptional activator proteins) are bound to the regulatory sequence(s).

The term "nucleic acid" or "nucleic acid construct" as herein defined refers to polymer of nucleotides, which may be either single- or double-stranded, which is a polynucleotide such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded polynucleotides. The term DNA used herein also encompasses cDNA, i.e. complementary or copy DNA produced from an RNA template by the action of reverse transcriptase (RNA-dependent DNA polymerase). A nucleic acid sequence as well known in the art is given in the 5' to 3' direction.

In some embodiments the nucleic acid construct according to the invention is an isolated or purified nucleic acid construct.

As indicated above, the isolated nucleic acid constructs according to the invention may further comprise additional elements such as regulatory and control elements.

As detailed in Example 1 below, the AChE-Fc fusion protein described herein was prepared by adding a sequence encoding the Kappa-leader sequence (also referred to herein as "K"), having the amino acid sequence of MDM-RAHVHLLGLLLLWLPGAKC (denoted by SEQ ID NO. 11, Table 2) to the 5' end of the nucleic acid sequence encoding the modified AChE fusion polypeptide.

As detailed in Example 2 below, an additional nucleic acid construct encoding the AChE-Fc fusion protein was prepared by adding a sequence encoding the signal peptide of the full length human AChE (also referred to herein as "SP"), having the amino acid sequence of MRPPQ-CLLHTPSLASPLLLLLLWLLGGGVGA (denoted by SEQ ID NO. 12, Table 2) to the 5' end of the nucleic acid sequence encoding the modified AChE fusion polypeptide.

The addition of a leader is mandatory for the secretion of the protein. Without wishing to be bound by theory, different leaders may affect the amount of protein secreted but will not affect its structure or activity.

Therefore, in some embodiments the isolated nucleic acid construct as herein defined further comprises a sequence encoding a secretion signal situated at the 5' end of the nucleic acid sequence encoding the fusion polypeptide according to the invention.

The term "secretion signal" as herein defined refers to a signal peptide (also referred to as a signal sequence, targeting signal, localization signal, localization sequence, transit peptides leader sequence or leader peptide) which is a short (5-30 amino acids long) peptide present at the N-terminus of the majority of newly synthesized proteins that are destined towards the secretory pathway.

In some embodiments the isolated nucleic acid construct according to the invention comprises a secretion signal which is a kappa-leader sequence having the amino acid sequence denoted by SEQ ID NO: 11. In other embodiments the secretion signal is the native signal peptide of human AChE having the amino acid sequence denoted by SEQ ID NO: 12.

In some further embodiments the isolated nucleic acid construct according to the invention is of the nucleic acid sequence denoted by SEQ ID NO: 18. In still further embodiments the nucleic acid construct according to the invention is of the nucleic acid sequence denoted by SEQ ID NO: 19.

The present invention further provides an expression vector comprising the isolated nucleic acid construct as herein defined.

The term "expression vector", also referred to as "expression vehicle" or "expression construct", as used herein, encompasses vectors such as plasmids, viruses, bacteriophage, integratable DNA fragments, and other vehicles, which comprise nucleic acid sequences encoding the desired polypeptide and enable its expression in a host cell. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. The expression vector in accordance with the invention may be competent with expression in bacterial, yeast, or mammalian host cells, to name but few.

For example, the fusion polypeptide according to the present invention was prepared by incorporating the nucleic acid construct encoding thereof into a mammalian expression vector, as detailed below. The mammalian expression vector (also referred to herein as the "plasmid") comprising the nucleic acid sequence of the fusion polypeptide was transiently transfected to FreeStyle HEK293 cells and the supernatant was collected after seven days.

The present invention further provides an isolated host cell comprising the nucleic acid construct or the expression vector according to the present invention.

The term "host cells" as used herein refers to cells which are susceptible to the introduction of the isolated nucleic acid construct or the expression vector according to the invention. Preferably, said cells are mammalian cells, for example CHO cells, or HEK 293 cells.

Any of the well known procedures for introducing foreign nucleotide sequences into host cells (transfection) may be used.

As detailed in Example 1 below, the AChE-Fc fusion protein construct according to the invention was prepared by fusing a modified AChE, which lacks both its N-terminal signal peptide and its C-terminal tail, to the Fc domain of human IgG1 using the K-leader sequence as a secretion signal sequence. Example 2 described the preparation of a AChE-Fc fusion protein construct according to the invention prepared using the signal peptide sequence of native AChE.

Figure 7A:
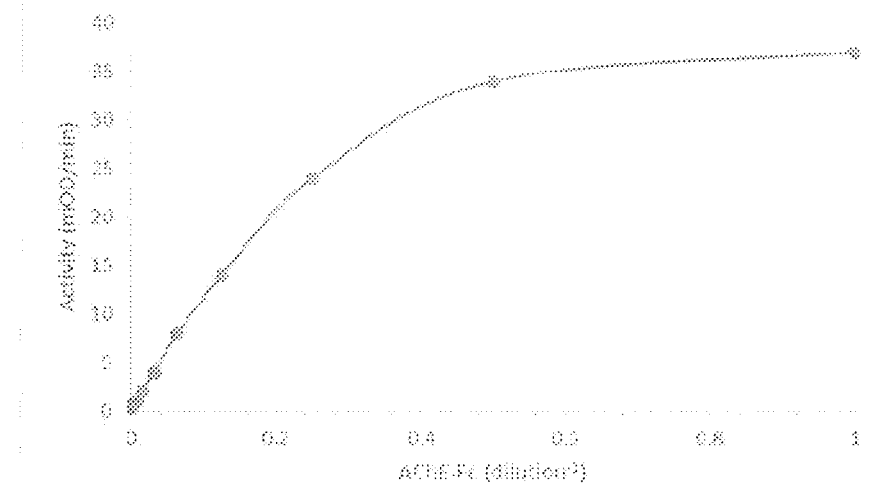
FIG. 7A is a graph showing AChE activity as measured in supernatant samples of the HEK293 cells that were transiently transfected with the plasmid encoding for the AChE fusion protein having the native signal sequence of AChE.
Figure 7B:
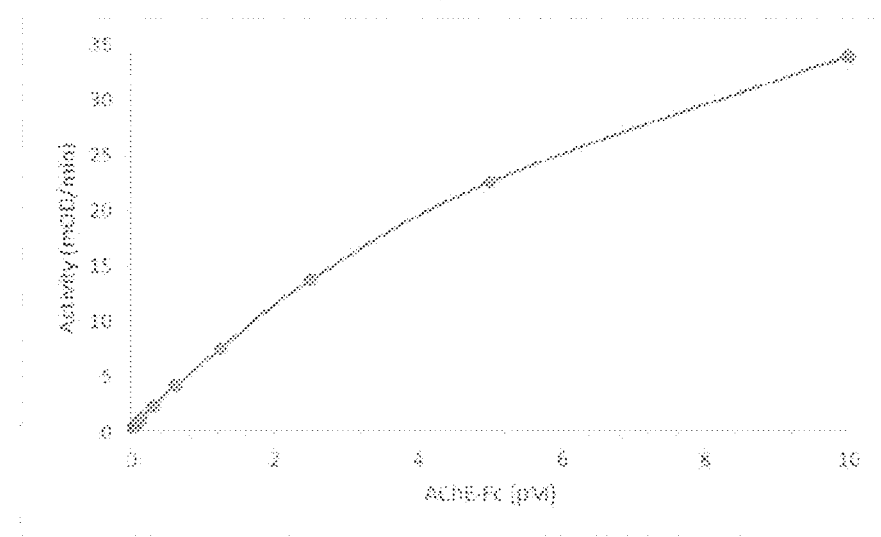
FIG. 7B is a graph showing AChE activity of purified AChE-Fc fusion protein obtained from cells transfected with a plasmid encoding the AChE fusion protein having the Kappa-leader sequence.
Figure 8:
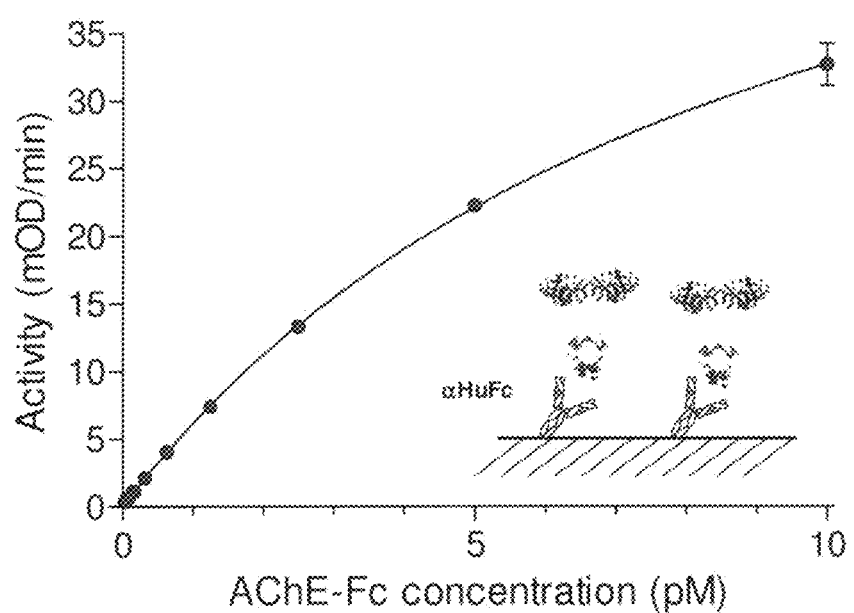
FIG. 8 is a diagram showing enzymatic activity (AChE activity mOD/minute) as a function of AChE-Fc concentration. Plates were coated with an anti-HuFc specific antibody, followed by the addition of increasing amounts of AChE-Fc fusion protein (as illustrated in the figure inset). The plates were then washed, the AChE specific substrate Acetyl-thiocholin (ATC) was added and the enzymatic activity was measured.

The activity of the AChE-Fc fusion polypeptide prepared as herein described is evidenced from FIG. 7A and FIG. 7B, which shows the results obtained in an ELISA assay conducted with supernatant samples of HEK293 cells that were transiently transfected with the plasmid encoding the AChE polypeptide as herein defined.

In addition, the AChE fusion polypeptide as herein defined was shown to have similar kinetic parameters as those of the native AChE enzyme, in an in vitro kinetic analysis, as detailed in Example 5 below.

Therefore, in another one of its aspects the present invention provides a method of producing the fusion polypeptide as herein defined, comprising culturing the host cell as herein defined under conditions suitable for expression of the fusion polypeptide in the host cell and recovering the fusion polypeptide thereby produced.

Laboratory techniques for culturing host cells are well known in the art. Cells are generally grown and maintained at an appropriate temperature and gas mixture (typically, 37° C., 5% $CO_2$ for mammalian cells) in a cell incubator. Culture conditions vary for each host cell type.

Any conditions suitable for expression of the fusion polypeptide in the host cell are encompassed by the present invention. As detailed below, the HEK293 cells transfected with the expression vector carrying the fusion polypeptide as herein defined were grown for 7 days under standard growth conditions.

Any of the well known procedures for recovering the fusion polypeptide as herein defined may be used. In some embodiments, cell-culture supernatants may be adsorbed to procainamide SEPHAROSE (a cross-linked, beaded form of agarose) 4B columns (4000 units/ml resin which are then rinsed with 50 mM sodium phosphate buffer, pH 8.0/1 mM EDTA and again with 50 mM sodium phosphate buffer, pH 8.0/0.4 M NaCl/1 mM EDTA. Elution of the fusion polypeptide as herein defined may be performed for example with decamethonium (0.02 M) in 50 mM sodium phosphate buffer, pH 8.0/1 mM EDTA.

In order to verify the activity and integrity of the obtained fusion polypeptide prepared as described herein, standard methods well-known in the art may be employed, as for example the ELISA assay and the kinetic assay described herein.

The present invention further provides a pharmaceutical composition comprising the fusion polypeptide according to the invention and a pharmaceutically acceptable carrier.

The term "pharmaceutical composition" as herein defined comprises the fusion polypeptide according to the invention as the active agent and a buffering agent, an agent which adjusts the osmolarity of the composition and optionally, one or more pharmaceutically acceptable carriers, excipients and/or diluents as known in the art. Supplementary active ingredients can also be incorporated into the compositions, e.g. additional prophylaxis or therapeutic agents.

Any known pharmaceutically acceptable carrier may be used for preparing the pharmaceutical composition according to the invention. For example, the term "pharmaceutically acceptable carrier, excipient or diluent" includes any and all solvents, dispersion media, coatings, antibacterial and antifungal agents and the like, as known in the art. The carrier can be solvent or dispersion medium containing, for example, water, ethanol, polyol (for example, glycerol, propylene glycol, and liquid polyethylene glycol, and the like), suitable mixtures thereof, and vegetable oils. Each carrier should be both pharmaceutically and physiologically acceptable in the sense of being compatible with the other ingredients and not injurious to the subject. Except as any conventional media or agent is incompatible with the active ingredient, its use in the therapeutic composition is contemplated.

As indicated above, organophosphate poisoning (OP poisoning) results from exposure to organophosphorus (OP) compounds, which cause the inhibition of acetylcholinesterase (AChE), leading to the accumulation of acetylcholine (ACh) in the body. The health effects associated with organophosphate poisoning are a result of excess acetylcholine (ACh) present at different nerves and receptors in the body. For example, accumulation of ACh at motor nerves causes overstimulation of nicotinic expression at the neuromuscular junction.

Organophosphorus (OP) compounds (organic compounds that contain a carbon-phosphorus bond) are a diverse group of chemicals that include, among others, insecticides, antihelmintics (drugs that are used for killing parasitic worms) and nerve gases. For example, organophosphorus (OP) compounds are, but not limited to insecticides (for example malathion, parathion, diazinon, fenthion, etc.), nerve gases (for example soman, sarin, tabun, VX, etc.), ophthalmic agents (for example echothiophate, isoflurophate, etc.), antihelmintics such as trichlorofon and herbicides (for example tribufos, merphos, etc.).

A possible strategy to prevent the toxic manifestations of OP poisoning is to sequester OP compounds in the circulation using exogenously administered AChE, thereby detoxifying them before they can inhibit the endogenous AChE. However, and as indicated above recombinant choline esterases have short half lives in the circulation system.

Figure 9:
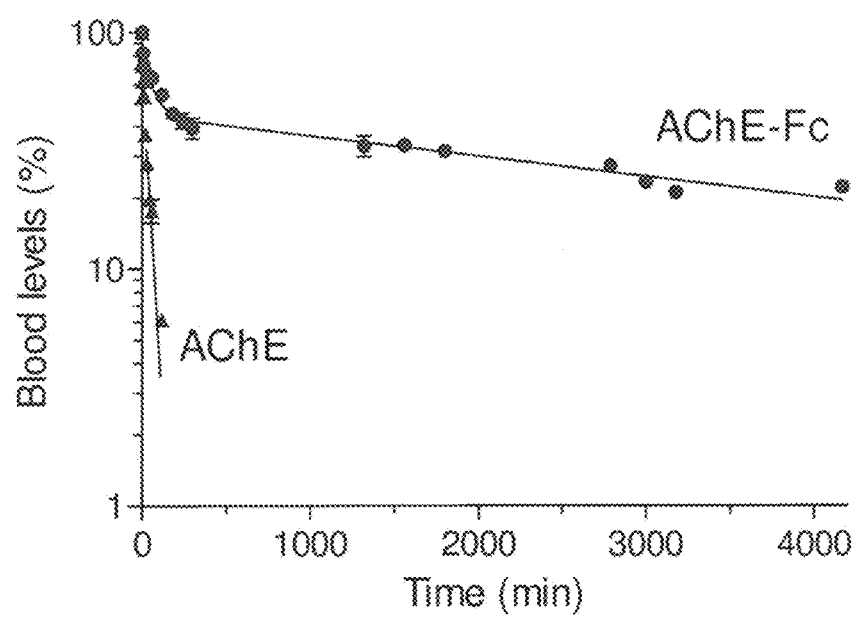
FIG. 9 is a graph showing AChE and AChE-Fc levels in mouse serum following administration of the recombinant (AChE-Fc) and the native (AChE) enzymes.

Surprisingly, as described below, the circulatory half-life of the fusion polypeptide AChE-Fc as herein defined was extremely longer when compared to the half-life of free AChE (Table 3 below and FIG. 9). The prolonged half-life of the AChE-Fc fusion protein prepared as described above provides a clear prophylactic potential for scavenging compounds targeting the AChE enzyme (e.g. organophosphate compounds) from the circulatory system for as long as 60 hours, or more, after its injection.

Furthermore, the reactivity of the AChE-Fc fusion polypeptide, prepared as herein described, against the organophosphorus compounds VX and Sarin was verified as detailed in Table 4 below.

Therefore in another one of its aspects the present invention provides the fusion polypeptide or the pharmaceutical composition according to the invention for use in prophylaxis of organophosphate poisoning.

The term "prophylaxis" as herein defined refers to acting in a protective manner, to defend against or prevent from organophosphate poisoning.

In a further aspect the present invention provides a method of prophylaxis of organophosphate poisoning comprising administering an effective amount of the fusion polypeptide or the pharmaceutical composition according to the invention to a subject in need thereof.

Exposure to OP compounds may occur on a daily basis through inhalation, absorption, and ingestion, most commonly of food that has been treated with an organophosphate herbicide or insecticide. Exposure to OP compounds may also occur during war.

Therefore, the term "subject in need thereof" in the context of the present invention means warm-blooded animals, such as for example household animals or farm animals (e.g. dogs, cats, cattle, sheep, horses etc) and humans at risk of being exposed to OP compounds or anyone who is at a risk of coming in contact with OP compounds, for example farmers, agronomists, laboratory professionals and military personnel.

In specific embodiments the fusion polypeptide, the pharmaceutical composition comprising thereof or its use in a method according to the present invention is wherein said fusion polypeptide comprises the amino acid sequence denoted by SEQ ID NO: 17.

In further specific embodiments the fusion polypeptide, the pharmaceutical composition comprising thereof or its use in a method according to the present invention is wherein said fusion polypeptide consists of the amino acid sequence denoted by SEQ ID NO: 17.

Administration according to the present invention may be performed by any of the following routes: oral administration, intravenous, intramuscular, intraperitoneal, intratechal or subcutaneous injection, intrarectal administration, intranasal administration, ocular administration or topical administration. In preferred embodiments the administration is performed by intravenous or intramuscular injection.

In specific embodiments the fusion polypeptide or the pharmaceutical composition according to the invention is administered to the subject between about 30 days to about 1 minute before potential exposure to OP compounds.

In some embodiments the method of prophylaxis of organophosphate poisoning according to the invention further comprises administering an effective amount of at least one additional therapeutic agent as herein defined. In other specific embodiments the fusion polypeptide or the pharmaceutical composition as herein defined is administered with at least one additional therapeutic agent.

In some embodiments the fusion polypeptide or pharmaceutical composition comprising same as herein defined is administered concomitantly with the at least one additional therapeutic agent as herein defined. In other embodiments the fusion polypeptide or pharmaceutical composition comprising same as herein defined is administered before the administration of the at least one additional therapeutic agent as herein defined.

Currently, the standard medical therapy administered after exposure to OP compounds includes a muscarinic antagonist (usually atropine), an acetylcholinesterase reactivator (for example pralidoxime, 2-PAM), and benzodiazepines (for example diazepam).

Therefore in some embodiments the at least one additional therapeutic agent is selected from atropine, glycopyrrolate, benzodiazepines, pralidoxime and native cholinesterase(s).

The term "atropine" as known in the art refers to an agent indicated for temporary blockade of severe or life threatening muscarinic effects, e.g., as an antisialagogue, an antivagal agent, an antidote for organophosphorus or muscarinic mushroom poisoning, and to treat bradyasystolic cardiac arrest.

The term "glycopyrrolate" as known in the art refers to an anticholinergic agent.

Benzodiazepines as known in the art enhance the effect of the neurotransmitter gamma-aminobutyric acid (GABA) at the GABA receptor, resulting in sedative, hypnotic (sleep-inducing), anxiolytic (anti-anxiety), anticonvulsant, and muscle relaxant properties. These properties make benzodiazepines useful in treating anxiety, insomnia, agitation, seizures, muscle spasms, alcohol withdrawal and as a premedication for medical or dental procedures.

"Pralidoxime" (2-pyridine aldoxime methyl chloride or 2-PAM) belongs to a family of compounds called oximes that bind to organophosphate-inactivated acetylcholinesterase. It is known in the art for its use against poisoning by organophosphates or acetylcholinesterase inhibitors (nerve agents) in conjunction with atropine and diazepam.

The term "native cholinesterase" or "non fused cholinesterase" as herein defined refers to any native cholinesterase known in the art that may be used in conjunction with the fusion polypeptide as herein defined, for example but not limited to human AChE.

In some embodiments, administering at least one additional therapeutic agent directed against organophosphate compounds or counteracting their effect is performed as a further post exposure therapy step.

Thus, in specific embodiments, the additional therapeutic agent is administered after the exposure to organophosphates (or after exposure to organophosphate poisoning).

By the term "after the exposure to organophosphates" it is meant that the additional therapeutic agent as defined above is administered at least about 5, 6, 7, 8, 9, 10, 15, 20, 25, 30, 40, 50, 60 minutes or more after exposure to organophosphates. The at least one additional therapeutic agent as defined above may be formulated for self-administration.

The "effective amount" of the fusion polypeptide per se or comprised in the pharmaceutical composition as herein defined may be determined by a skilled person by considerations well known in the art.

The present invention further provides for a method of increasing the circulatory half-life of AChE, said method comprising preparing a fusion polypeptide comprising:
(c) an acetylcholinesterase (AChE) polypeptide component comprising a modified human AChE polypeptide having an amino acid sequence denoted by SEQ ID NO: 8 or variants thereof; and
(d) a fragment crystallizable (Fc) domain of human IgG, or variants thereof wherein the human AChE polypeptide component retains the functional activity of human AChE.

The term "circulatory half-life" with reference to AChE as herein defined refers to the time required for half of the AChE molecules administered to an organism to be metabolized or eliminated by normal biological processes.

The circulatory half-life of AChE or of the fusion polypeptide comprising AChE polypeptide component as herein defined may be measured using any method known to a person of skill in the art. For example and as exemplified herein below, the circulatory half-life of AChE may be measured in animals (for example mice) injected with the fusion polypeptide, where mice injected with the native AChE are used as control.

Blood samples are taken from these animals at different intervals, for example between 45 sec to 70 hours after injection. The blood samples withdrawn from the animals are processed and used for an ELISA assay to determine the presence of the fusion polypeptide comprising AChE polypeptide component as herein defined or the presence of native AChE.

By still another one of its aspects the present invention provides a fusion polypeptide as herein defined or a pharmaceutical composition comprising the fusion polypeptide as herein defined for preparing a medicament for the prophylaxis of organophosphate poisoning.

In specific embodiments the present invention provides a fusion polypeptide comprising the amino acid sequence denoted by SEQ ID NO: 17 or a pharmaceutical composition comprising said fusion polypeptide for preparing a medicament for the prophylaxis of organophosphate poisoning.

In further specific embodiments the present invention provides a fusion polypeptide consisting of the amino acid sequence denoted by SEQ ID NO: 17 or a pharmaceutical composition comprising said fusion polypeptide for preparing a medicament for the prophylaxis of organophosphate poisoning.

The present disclosure further provides a kit comprising:

(i) at least one fusion polypeptide comprising:

(a) an acetylcholinesterase (AChE) polypeptide component comprising a modified human AChE polypeptide having an amino acid sequence denoted by SEQ ID NO: 8 or variants thereof; and (b) a fragment crystallizable (Fc) domain of human IgG or variants thereof, wherein the fusion polypeptide retains the functional activity of human AChE; and (ii) instructions for use.

In some embodiments the kit as herein defined further comprises at least one additional therapeutic agent according to the present invention.

In some embodiments the kit as herein defined comprises the at least one fusion polypeptide in a first unit dosage form and the at least one additional therapeutic agent in a second unit dosage form.

The at least one fusion polypeptide and the at least one additional therapeutic agent may be administered to a subject in need thereof concomitantly or separately, before or after exposure of the subject to organophosphate poisoning.

It is appreciated that the term "purified" or "isolated" refers to molecules, such as amino acid or nucleic acid sequences, peptides, polypeptides or antibodies that are removed from their natural environment, isolated or separated. An "isolated fusion polypeptide", "an isolated nucleic acid construct" or an "isolated host cell" is therefore a purified fusion polypeptide, nucleic acid construct or host cell, respectively. As used herein, the term "purified" or "to purify" also refers to the removal of contaminants from a sample.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

When used in connection with an amino acid sequence, the term "comprising" means that a compound may include additional amino acid residues on either or both of the N- or C-termini of the given sequence.

EXAMPLES

Without further elaboration, it is believed that one skilled in the art can, using the preceding description, utilize the present disclosure to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Standard medicinal chemistry methods known in the art not specifically described herein are generally followed essentially in the series "Comprehensive Medicinal Chemistry" by various authors and editors, published by Pergamon Press.

Experimental Procedures

Primers

The primers designed and used for constructing the acetylcholinesterase (AChE) Fc-fusion protein described below are detailed in Table 1 below. All of the primers were synthesized by Integrated DNA Technologies (IDT).

TABLE 1

Primers designed and used for cloning of the AChE Fc-fusion protein

| SEQ ID NO: | Primer name | Sequence |
|---|---|---|
| 1 | K-AChET1 Forward | CTCCTGCTGCTCTGG CTGCCCGGGGCCAAA TGTGAGGGCCGGGAG GATGC |
| 2 | HuK2 Forward | TATAAGCAGAGCTCA TGGACATGAGGGCCC ATGTGCACCTTCTGG GGCTCCTGCTGCTCT GG |
| 3 | AChET Reverse | GAGCCTCCGAGGCGG TGGCGCTGAGCAAT TT |
| 4 | AChET-h2 Reverse | GAGTTTTGTCACTAG ATTTGGGCTCGGGAG CCTCCGAGGCGGTGG CGCT |
| 5 | AChET hinge Forward | GCCTCGGAGGCTCCC GAGCCCAAATCTAGT GACAA |
| 6 | HuK-ChE Forward | TATAAGCAGAGCTCA TGGACATGAGGGCCC ATG |
| 7 | Hinge Reverse | GTCCACCACCACGCA TGTG |

Assembly PCR

In order to construct a fusion protein that comprises the human Acetylcholine esterase enzyme linked to the Fc portion of an antibody, several different components were amplified from different sources and then assembled together by PCR, as detailed below.

Human AChE was amplified from the AChE vector (7) using primers having the nucleic acid sequences denoted by SEQ ID NO: 1 and SEQ ID NO: 3 (Table 1 above). The nucleic acid sequence encoding the AChE enzyme was amplified from the AChE vector without the sequence encoding the AChE N-terminal signal peptide and without the sequence encoding the last (C-terminal) 40 amino acids that comprise the AChE enzyme "tail". The AChE enzyme tail is involved in the formation of AChE tetramers (7). This procedure resulted in a nucleic acid sequence encoding a polypeptide having the amino acid sequence denoted by SEQ ID NO. 8 (Table 2), also termed herein "modified AChE". In other words, the procedure described above resulted in a nucleic acid sequence encoding a polypeptide fragment of the human AChE enzyme, which does not include the N-terminal signal peptide and from which a 40 amino acid-long C-terminal tail was deleted.

Then, a nucleic acid sequence encoding a five amino acids spacer, namely ASEAP (denoted by SEQ ID NO. 9, Table 2) was added to the 3' end of the nucleic acid construct encoding the modified AChE. This procedure resulted in a nucleic acid sequence encoding a polypeptide having the amino acid sequence denoted by SEQ ID NO. 10 (Table 2), namely the polypeptide resulting from fusing the peptide spacer of the amino acid sequence ASEAP to the C terminus of modified AChE.

A second PCR amplification was used to add a sequence encoding the Kappa-leader sequence (also referred to herein as "K"), having the amino acid sequence of MDMRAHVHLLGLLLLWLPGAKC (denoted by SEQ ID NO. 11, Table 2) to the 5' end of the sequence encoding the modified AChE (which is fused at its C terminus to the spacer), using primers having the nucleic acid sequences denoted by SEQ ID NO: 2 and SEQ ID NO: 4 (Table 1 above). This step resulted in a nucleic acid sequence encoding a polypeptide having the amino acid sequence denoted by SEQ ID NO: 13 (Table 2).

Alternatively, a nucleic acid sequence encoding the signal peptide of native human AChE, having the amino acid sequence denoted by SEQ ID NO: 12 (Table 2) was added to the 5' end of the sequence encoding the modified AChE (that in turn is conjugated to the spacer at its C terminus).

The hinge region of an IgG1 antibody (having the amino acid sequence defined by SEQ ID NO: 14, Table 2) was amplified from a mammalian (human) cDNA) full-length Ig expression vector designed by the inventors, using primers having the nucleic acid sequences denoted by SEQ ID NO: 5 and SEQ ID NO: 7 (Table 1). A cysteine residue that facilitates the covalent linkage at the hinge region between the heavy and the light chains of IgG1, was replaced by a serine, as detailed below, in order to prevent non-specific bonding.

The cysteine to serine substitution was performed by a point mutation inserted in the hinge region of IgG1 at position 1723 of the nucleic acid sequence denoted by SEQ ID NO: 18 (Table 2 and FIG. 2, encoding the full length fusion protein). This point mutation resulted in replacing a "T" with an "A", thereby replacing the Cysteine residue which is present at this position in the original (native) human AChE to Serine in the current fusion construct (namely C575 to S in the sequence denoted by SEQ ID NO: 16, Table 2) in order to prevent the formation of non-specific bonds.

The nucleic acid encoding the kappa-leader sequence followed by the modified AChE enzyme followed by the spacer (namely the nucleic acid sequence encoding the polypeptide denoted by SEQ ID NO: 13, Table 2) was then assembled 5' to the IgG1 hinge region by PCR (under the conditions of a single cycle of 2 min at 95° C., 35 cycles of 1 min at 94° C., 30 sec at 57° C. and 1.5 min at 72° C. and a final single cycle of 5 min at 72° C.), using primers having the nucleic acid sequences denoted by SEQ ID NO: 6 and SEQ ID NO: 7 (Table 1). The primers were also designed to add appropriate restriction sites to the leader-enzyme sequence.

TABLE 2

Sequences of the AChE Fc-fusion protein and components thereof

| SEQ ID NO: | Sequence | Name |
|---|---|---|
| 8 | EGREDAELLVTVRGGRLRGIRLKTPGGPVSAFLGIPF AEPPMGPRRFLPPEPKQPWSGVVDATTFQSVCYQYV DTLYPGFEGTEMWNPNRELSEDCLYLNVWTPYPRPT SPTPVLVWIYGGGFYSGASSLDVYDGRFLVQAERTV LVSMNYRVGAFGFLALPGSREAPGNVGLLDQRLAL QWVQENVAAFGGDPTSVTLFGESAGAASVGMHLL SPPSRGLFHRAVLQSGAPNGPWATVGMGEARRRAT QLAHLVGCPPGGTGGNDTELVACLRTRPAQVLVNH EWHVLPQESVFRFSFVPVVDGDFLSDTPEALINAGDF HGLQVLVGVVKDEGSYFLVYGAPGFSKDNESLISRA EFLAGVRVGVPQVSDLAAEAVVLHYTDWLHPEDPA RLREALSDVVGDHNVVCPVAQLAGRLAAQGARVY AYVFEHRASTLSWPLWMGVPHGYEIEFIFGIPLDPSR NYTAEEKIFAQRLMRYWANFARTGDPNEPRDPKAP QWPPYTAGAQQYVSLDLRPLEVRRGLRAQACAFVV NRFLPKLLSAT | Amino acid sequence of the Modified AChE |
| 9 | ASEAP | Amino acid sequence of the spacer |
| 10 | EGREDAELLVTVRGGRLRGIRLKTPGGPVSAFLGIPF AEPPMGPRRFLPPEPKQPWSGVVDATTFQSVCYQYV DTLYPGFEGTEMWNPNRELSEDCLYLNVWTPYPRPT SPTPVLVWIYGGGFYSGASSLDVYDGRFLVQAERTV LVSMNYRVGAFGFLALPGSREAPGNVGLLDQRLAL QWVQENVAAFGGDPTSVTLFGESAGAASVGMHLL SPPSRGLFHRAVLQSGAPNGPWATVGMGEARRRAT QLAHLVGCPPGGTGGNDTELVACLRTRPAQVLVNH EWHVLPQESVFRFSFVPVVDGDFLSDTPEALINAGDF HGLQVLVGVVKDEGSYFLVYGAPGFSKDNESLISRA EFLAGVRVGVPQVSDLAAEAVVLHYTDWLHPEDPA RLREALSDVVGDHNVVCPVAQLAGRLAAQGARVY AYVFEHRASTLSWPLWMGVPHGYEIEFIFGIPLDPSR NYTAEEKIFAQRLMRYWANFARTGDPNEPRDPKAP QWPPYTAGAQQYVSLDLRPLEVRRGLRAQACAFVV NRFLPKLLSATASEAP | Amino acid sequence of the Modified AChE fused to a spacer |
| 11 | MDMRAHVHLLGLLLLWLPGAKC | Amino acid sequence of the Kappa-leader sequence |
| 12 | MRPPQCLLHTPSLASPLLLLLLWLLGGGVGA | Amino acid sequence of the AChE signal peptide |
| 13 | MDMRAHVHLLGLLLLWLPGAKCEGREDAELLVTVR GGRLRGIRLKTPGGPVSAFLGIPFAEPPMGPRRFLPP EPKQPWSGVVDATTFQSVCYQYVDTLYPGFEGTEM WNPNRELSEDCLYLNVWTPYPRPTSPTPVLVWIYGG GFYSGASSLDVYDGRFLVQAERTVLVSMNYRVGAFG FLALPGSREAPGNVGLLDQRLALQWVQENVAAFGG DPTSVTLFGESAGAASVGMHLLSPPSRGLFHRAVLQ SGAPNGPWATVGMGEARRRATQLAHLVGCPPGGT GGNDTELVACLRTRPAQVLVNHEWHVLPQESVFRF SFVPVVDGDFLSDTPEALINAGDFHGLQVLVGVVKD EGSYFLVYGAPGFSKDNESLISRAEFLAGVRVGVPQV SDLAAEAVVLHYTDWLHPEDPARLREALSDVVGDH | Kappa-leader sequence fused to modified AChE that is fused to a spacer (K-Modified AChE-spacer) |

TABLE 2-continued

Sequences of the AChE Fc-fusion protein and components thereof

| SEQ ID NO: | Sequence | Name |
|---|---|---|
| | NVVCPVAQLAGRLAAQGARVYAYVFEHRASTLSWP LWMGVPHGYEIEFIFGIPLDPSRNYTAEEKIFAQRLM RYWANFARTGDPNEPRDPKAPQWPPYTAGAQQY VSLDLRPLEVRRGLRAQACAFWNRFLPKLLSATASEAP | |
| 14 | EPKSSDKTHTCPPCPAPELLGGPSVFLFPPKPKDTLMISRTPE VTCVVVD | hinge region of IgG1 |
| 15 | EPKSSDKTHTCPPCPAPELLGGPSVFLFPPKPKDTLM ISRTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSREEM TKNQVSLTCLVKGFYPSDIAVEWESNGQPENNYKTT PPVLDSDGSFFLYSKLTVDKSRWQQGNVFSCSVMH EALHNHYTQKSLSLSPGK | Amino acid sequence of the Fc domain |
| 16 | MDMRAHVHLLGLLLLWLPGAKCEGREDAELLVTV RGGRLRGIRLKTPGGPVSAFLGIPFAEPPMGPRRFL PPEPKQPWSGVVDATTFQSVCYQYVDTLYPGFEG TEMWNPNRELSEDCLYLNVWTPYPRPTSPTPVLV WIYGGGFYSGASSLDVYDGRFLVQAERTVLVSMN YRVGAFGFLALPGSREAPGNVGLLDQRLALQWVQ ENVAAFGGDPTSVTLFGESAGAASVGMHLLSPPSR GLFHRAVLQSGAPNGPWATVGMGEARRRATQLA HLVGCPPGGTGGNDTELVACLRTRPAQVLVNHEW HVLPQESVFRFSFVPVVDGDFLSDTPEALINAGDFH GLQVLVGVVKDEGSYFLVYGAPGFSKDNESLISRAE FLAGVRVGVPQVSDLAAEAVVLHYTDWLHPEDPA RLREALSDVVGDHNVVCPVAQLAGRLAAQGARVY AYVFEHRASTLSWPLWMGVPHGYEIEFIFGIPLDPS RNYTAEEKIFAQRLMRYWANFARTGDPNEPRDPK APQWPPYTAGAQQYVSLDLRPLEVRRGLRAQACA FWNRFLPKLLSATASEAPEPKSSDKTHTCPPCPAPE LLGGPSVFLFPPKPKDTLMISRTPEVTCVVVDVSHE DPEVKFNWYVDGVEVHNAKTKPREEQYNSTYRV VSVLTVLHQDWLNGKEYKCKVSNKALPAPIEKTIS KAKGQPREPQVYTLPPSREEMTKNQVSLTCLVKG FYPSDIAVEWESNGQPENNYKTTPPVLDSDGSFF LYSKLTVDKSRWQQGNVFSCSVMHEALHNHYTQ KSLSLSPGK | Amino acid sequence of the Kappa-leader sequence fused to Modified AChE, the spacer and the Fc domain (K-Modified AChE-spacer-Fc or K-NL1 fusion protein) |
| 17 | EGREDAELLVTVRGGRLRGIRLKTPGGPVSAFLGIPFAEPPMG PRRFLPPEPKQPWSGVVDATTFQSVCYQYVDTLYPGFEGTEM WNPNRELSEDCLYLNVWTPYPRPTSPTPVLVWIYGGGFYSGA SSLDVYDGRFLVQAERTVLVSMNYRVGAFGFLALPGSREAPG NVGLLDQRLALQWVQENVAAFGGDPTSVTLFGESAGAASVG MHLLSPPSRGLFHRAVLQSGAPNGPWATVGMGEARRRATQL AHLVGCPPGGTGGNDTELVACLRTRPAQVLVNHEWHVLPQE SVFRFSFVPVVDGDFLSDTPEALINAGDFHGLQVLVGVVKDE GSYFLVYGAPGFSKDNESLISRAEFLAGVRVGVPQVSDLAAE AVVLHYTDWLHPEDPARLREALSDVVGDHNVVCPVAQLAG RLAAQGARVYAYVFEHRASTLSWPLWMGVPHGYEIEFIFGIP LDPSRNYTAEEKIFAQRLMRYWANFARTGDPNEPRDPKAPQ WPPYTAGAQQYVSLDLRPLEVRRGLRAQACAFVVNRFLPKLL SATASEAPEPKSSDKTHTCPPCPAPELLGGPSVFLFPPKPKDTL MISRTPEVTCVVVDVSHEDPEVKFNWYVDGVEVHNAKTKPR EEQYNSTYRVVSVLTVLHQDWLNGKEYKCKVSNKALPAPIE KTISKAKGQPREPQVYTLPPSREEMTKNQVSLTCLVKGFYPSD IAVEWESNGQPENNYKTTPPVLDSDGSFFLYSKLTVDKSRWQ QGNVFSCSVMHEALHNHYTQKSLSLSPGK | Amino acid sequence of the NL1 fusion protein |
| 18 | ATGGACATGAGGGCCCATGTGCACCTTCTGGGGCTCCTGCT GCTCTGGCTGCCCGGGGCCAAATGTGAGGGCCGGGAGGAT GCAGAGCTGCTGGTGACGGTGCGTGGGGGCCGGCTGCGGG GCATTCGCCTGAAGACCCCCGGGGGCCCTGTCTCTGCTTC CTGGGCATCCCCTTTGCGGAGCCACCCATGGGACCCCGTCG CTTTCTGCCACCGGAGCCCAAGCAGCCTTGGTCAGGGGTGG TAGACGCTACAACCTTCCAGAGTGTCTGCTACCAATATGTG GACACCCTATACCCAGGTTTTGAGGGCACCGAGATGTGGA ACCCCAACCGTGAGCTGAGCGAGGACTGCCTGTACCTCAA CGTGTGGACACCATACCCCCGGCCTACATCCCCCACCCCTG TCCTCGTCTGGATCTATGGGGGTGGCTTCTACAGTGGGGCC TCCTCCTTGGACGTGTACGATGGCCGCTTCTTGGTACAGGC | Nucleic acid sequence encoding the K-NL1 fusion protein |

TABLE 2-continued

Sequences of the AChE Fc-fusion protein and components thereof

| SEQ ID NO: | Sequence | Name |
|---|---|---|
|  | CGAGAGGACTGTGCTGGTGTCCATGAACTACCGGGTGGGA GCCTTTGGCTTCCTGGCCCTGCCGGGGAGCCGAGAGGCCCC GGGCAATGTGGGTCTCCTGGATCAGAGGCTGGCCCTGCAG TGGGTGCAGGAGAACGTGGCAGCCTTCGGGGGTGACCCGA CATCAGTGACGCTGTTTGGGGAGAGCGCGGGAGCCGCCTC GGTGGGCATGCACCTGCTGTGTCCCCGCCCAGCCGGGGCCTGT TCCACAGGGCCGTGCTGCAGAGCGGTGCCCCCAATGGACC CTGGGCCACGTGGGCATGGGAGAGGCCCGTCGCAGGGCC ACGCAGCTGGCCCACCTTGTGGGCTGTCCTCCAGGCGGCAC TGGTGGGAATGACACAGAGCTGGTAGCCTGCCTTCGGACA CGACCAGCGCAGGTCCTGGTGAACCACGAATGGCACGTGC TGCCTCAAGAAAGCGTCTTCCGGTTCTCCTTCGTGCCTGTG GTAGATGGAGACTTCCTCAGTGACACCCCAGAGGCCCTCAT CAACGCGGGAGACTTCCACGGCCTGCAGGTGCTGGTGGGT GTGGTGAAGGATGAGGGCTCGTATTTTCTGGTTTACGGGGC CCCAGGCTTCAGCAAAGACAACGAGTCTCTCATCAGCCGG GCCGAGTTCCTGGCCGGGGTGCGGGTCGGGGTTCCCCAGG TAAGTGACCTGGCAGCCGAGGCTGTGGTCCTGCATTACACA GACTGGCTGCATCCCGAGGACCCGGCACGCCTGAGGGAGG CCCTGAGCGATGTGGTGGGCGACCACAATGTCGTGTGCCCC GTGGCCCAGCTGGCTGGGCGACTGGCTGCCCAGGGTGCCC GGGTCTACGCCTACGTCTTTGAACACCGTGCTTCCACGCTC TCCTGGCCCCTGTGGATGGGGGTGCCCCACGGCTACGAGAT CGAGTTCATCTTTGGGATCCCCCTGGACCCCTCTCGAAACT ACACGGCAGAGGAGAAAATCTTCGCCCAGCGACTGATGCG ATACTGGGCCAACTTTGCCCGCACAGGGGATCCCAATGAG CCCCGAGACCCCAAGGCCCCACAATGGCCCCCGTACACGG CGGGGGCTCAGCAGTACGTTAGTCTGGACCTGCGGCCGCT GGAGGTGCGGCGGGGCTGCGCGCCCAGGCCTGCGCCTTC TGGAACCGCTTCCTCCCCAAATTGCTCAGCGCCACCGCCTC GGAGGCTCCCGAGCCCAAATCTAGTGACAAAACTCACACA TGCCCACCGTGCCCAGCACCTGAACTCCTGGGGGGACCGTC AGTCTTCCTCTTCCCCCCAAAACCCAAGGACACCCTCATGA TCTCCCGGACCCCTGAGGTCACATGCGTGGTGGTGGACGTG AGCCACGAAGACCCTGAGGTCAAGTTCAACTGGTACGTGG ACGGCGTGGAGGTGCATAATGCCAAGACAAAGCCACGGGA GGAGCAGTACAACAGCACCTACCGGGTGGTCAGCGTCCTC ACCGTCCTGCACCAGGACTGGCTGAATGGCAAGGAGTACA AGTGCAAGGTCTCCAACAAAGCCCTCCCAGCCCCCATCGA GAAAACCATCTCCAAAGCCAAAGGGCAGCCACGGGAACCA CAGGTTTACACCCTGCCCCCATCCCGCGAGGAGATGACCA AGAACCAGGTCAGCCTGACCTGCCTGG TCAAAGGCTTCTATCCCAGCGACATCGCCGTGGAGTGGGA GAGCAATGGGCAGCCGGAGAACAACTACAAGACCACCCCT CCCGTGCTGGACTCCGACGGCTCCTTCTTCCTCTATAGCAA GCTCACCGTGGACAAGAGCAGGTGGCAGCAGGGGAACGTC TTCTCATGCTCCGTGATGCACGAGGCTCTGCACAACCACTA CACCCAGAAGAGCCTCTCCCTGTCTCCCGGTAAATGA |  |
| 19 | ATGCGGCCGCCACAGTGCCTTCTGCATACCCCCAGCCTTGC CAGCCCTCTGCTGCTGCTGCTGTTGTGGCTCCTGGGAGGTG GTGTTGGGGCGGAAGGTCGAGAGGACGCCGAGTTGCTGGT GACTGTCCGAGGGGACGGCTCCGGGGAATCCGCCTCAAA ACACCTGGGGCCCCGTCTCTGCGTTTCTGGGCATCCCTTT CGCAGAGCCACCCATGGGCCCCCGGAGATTCCTGCCCCCG GAACCCAAACAGCCTTGGTCAGGGGTGGTCGATGCCACAA CTTTCCAGAGCGTGTGCTATCAGTACGTTGACACCTTGTAT CCCGGATTTGAAGGCACTGAGATGTGGAACCCGAATCGAG AGCTGAGTGAGGACTGCCTGTATCTGAATGTGTGGACCCCG TACCCTAGACCAACCTCACCCACCCCTGTTCTCGTGTGGAT CTACGGGGAGGTTTTTACTCTGGGGCCAGCTCCCTGGACG TGTATGATGGCAGATTCCTGGTCCAGGCAGAACGGACAGT GCTCGTGAGTATGAATTATCGGGTGGGCGCCTTCGGATTCT TGGCACTGCCCGGATCCCGGGAGGCCCCAGGTAACGTGGG ACTCCTCGACCAGCGCCTGGCTCTGCAGTGGGTGCAAGAA AATGTAGCAGCGTTGGTGGGGACCCAACCAGTGTGACTCT CTTTGGTGAAAGCGCAGGGGCAGCTTCCGTGGGCATGCAT CTGTTGTCACCACCATCTAGGGGATTGTTCCACCGGGCTGT ACTGCAGTCTGGAGCGCCAAATGGACCATGGGCCACAGTG GGGATGGGTGAAGCCAGACGGCGCGCCACCCAGCTGGCAC ATCTGGTGGGCTGCCCACCTGGGGGCACCGGAGGCAACGA TACAGAACTGGTGGCCTGCCTTAGGACCCGCCCCGCTCAAG TCCTGGTGAATCACGAGTGGCATGTGCTCCCTCAGGAAAGC | Nucleic acid sequence encoding the SP-NL1 fusion protein |

TABLE 2-continued

Sequences of the AChE Fc-fusion protein and components thereof

| SEQ ID NO: | Sequence | Name |
|---|---|---|
| | GTGTTTCGGTTCTCATTCGTGCCCGTGGTGGATGGCGACTT TCTCAGCGACACACCCGAAGCGCTGATTAACGCCGGAGAT TTCCATGGCCTCCAGGTTCTTGTGGGTGTCGTAAAGGACGA GGGGTCCTACTTCCTGGTTTATGGCGCGCCAGGCTTCTCTA AGGATAATGAGAGCTTGATCTCTCGCGCGGAGTTTTTGGCA GGCGTGCGCGTCGGCGTGCCTCAGGTTTCAGACTTGGCAGC CGAGGCCGTGGTCCTCCATTATACGGACTGGCTGCACCCGG AGGATCCTGCCAGACTTCGCGAAGCTCTGTCAGACGTGGTC GGAGACCATAATGTCGTGTGCCCCGTGGCTCAGTTGGCTGG GCGCCTCGCAGCCCAAGGCGCCAGGGTATATGCGTACGTTT TCGAGCACCGCGCCAGCACACTCTCATGGCCCTCTTTGGATG GGCGTGCCCCACGGGTATGAAATCGAGTTCATATTCGGCAT CCCTCTGGATCCATCCAGAAACTACACCGCCGAAGAGAAG ATCTTCGCCCAGAGATTGATGAGATACTGGGCCAACTTTGC TCGGACCGGTGACCCTAACGAGCCCAGAGACCCGAAGGCT CCCCAGTGGCCTCCTTATACCGCGGGTGCACAGCAGTACGT AAGCCTGGACCTGAGACCACTGGAGGTGCGACGCGGACTG CGAGCACAGGCCTGCGCCTTTTGGAATCGGTTCCTCCCCAA GCTGTTGTCAGCCACCGCATCCGAAGCCCCCGAGCCCAAAT CTAGTGACAAAACTCACACATGCCCACCGTGCCCAGCACCT GAACTCCTGGGGGGACCGTCAGTCTTCCTCTTCCCCCCAAA ACCCAAGGACACCCTCATGATCTCCCGGACCCCTGAGGTCA CATGCGTGGTGGTGGACGTGAGCCACGAAGACCCTGAGGT CAAGTTCAACTGGTACGTGGACGGCGTGGAGGTGCATAAT GCCAAGACAAAGCCACGGGAGGAGCAGTACAACAGCACCT ACCGGGTGGTCAGCGTCCTCACCGTCCTGCACCAGGACTGG CTGAATGGCAAGGAGTACAAGTGCAAGGTCTCCAACAAAG CCCTCCCAGCCCCCATCGAGAAAACCATCTCCAAAGCCAA AGGGCAGCCACGGGAACCACAGGTTTACACCCTGCCCCCA TCCCGCGAGGAGATGACCAAGAACCAGGTCAGCCTGACCT GCCTGGTCAAAGGCTTCTATCCCAGCGACATCGCCGTGGAG TGGGAGAGCAATGGGCAGCCCGAGAACAACTACAAGACCA CCCCTCCCGTGCTGGACTCCGACGGCTCCTTCTTCCTCTATA GCAAGCTCACCGTGGACAAGAGCAGGTGGCAGCAGGGGA ACGTCTTCTCATGCTCCGTGATGCACGAGGCTCTGCACAAC CACTACACCCAGAAGAGCCTCTCCCTGTCTCCCGGTAAATG A | |
| 20 | ACCAAGGGCCCATCGGTCTTCCCACTGGCACCCTCCTCCAA GAGCACCTCTGGGGGCACAGCTGCCCTGGGCTGCCTGGTC AAGGACTACTTCCCTGAACCGGTGACGGTGTCGTGGAACTC AGGCGCCCTGACAAGCGGCGTGCACACCTTCCCGGCTGTG CTGCAGTCTTCAGGACTCTACTCCCTCAGCAGCGTGGTGAC CGTGCCCTCTAGCAGCTTGGGCACCCAGACCTACATCTGCA ACGTGAATCACAAGCCCAGCAACACCAAGGTGGACAAGAG AGTGGAGCCCAAATCTAGTGACAAAACTCACACATGCCCA CCGTGCCCAGCACCTGAACTCCTGGGGGACCGTCAGTCTT CCTCTTCCCCCCAAAACCCAAGGACACCCTCATGATCTCCC GGACCCCTGAGGTCACATGCGTGGTGGTGGACGTGAGCCA CGAAGACCCTGAGGTCAAGTTCAACTGGTACGTGGACGGC GTGGAGGTGCATAATGCCAAGACAAAGCCACGGGAGGAGC AGTACAACAGCACCTACCGGGTGGTCAGCGTCCTCACCGTC CTGCACCAGGACTGGCTGAATGGCAAGGAGTACAAGTGCA AGGTCTCCAACAAAGCCCTCCCAGCCCCCATCGAGAAAAC CATCTCCAAAGCCAAAGGGCAGCCACGGGAACCACAGGTT TACACCCTGCCCCCATCCCGCGAGGAGATGACCAAGAACC AGGTCAGCCTGACCTGCCTGGTCAAAGGCTTCTATCCCAGC GACATCGCCGTGGAGTGGGAGAGCAATGGGCAGCCCGAGA ACAACTACAAGACCACCCCTCCCGTGCTGGACTCCGACGG CTCCTTCTTCCTCTATAGCAAGCTCACCGTGGACAAGAGCA GGTGGCAGCAGGGGAACGTCTTCTCATGCTCCGTGATGCAC GAGGCTCTGCACAACCACTACACCCAGAAGAGCCTCTCCCT GTCTCCCGGTAAA | Nucleic acid sequence encoding the heavy-chain of human IgG1 |
| 21 | MRPPQCLLHTPSLASPLLLLLLWLLGGGVGAEGREDAELLVT VRGGRLRGIRLKTPGGPVSAFLGIPFAEPPMGPRRFLPPEPKQP WSGVVDATTFQSVCYQYVDTLYPGFEGTEMWNPNRELSEDC LYLNVWTPYPRPTSPTPVLVWIYGGGFYSGASSLDVYDGRFL VQAERTVLVSMNYRVGAFGFLALPGSREAPGNVGLLDQRLA LQWVQENVAAFGGDPTSVTLFGESAGAASVGMHLLSPPSRGL FHRAVLQSGAPNGPWATVGMGEARRRATQLAHLVGCPPGGT GGNDTELVACLRTRPAQVLVNHEWHVLPQESVFRFSFVPVVD GDFLSDTPEALINAGDFHGLQVLVGVVKDEGSYFLVYGAPGF | Amino acid sequence of the native AChE protein |

TABLE 2-continued

Sequences of the AChE Fc-fusion protein
and components thereof

| SEQ ID NO: | Sequence | Name |
|---|---|---|
| | SKDNESLISRAEFLAGVRVGVPQVSDLAAEAVVLHYTDWLHP<br>EDPARLREALSDVVGDHNVVCPVAQLAGRLAAQGARVYAY<br>VFEHRASTLSWPLWMGVPHGYEIEFIFGIPLDPSRNYTAEEKIF<br>AQRLMRYWANFARTGDPNEPRDPKAPQWPPYTAGAQQYVS<br>LDLRPLEVRRGLRAQACAFWNRFLPKLLSATDTLDEAERQW<br>KAEFHRWSSYMVHWKNQFDHYSKQDRCSDL | |

Cloning

A mammalian expression vector, containing the heavy-chain of human IgG1 (denoted by SEQ ID NO: 20, Table 2), under the control of the CMV promotor (designed by the inventors), was digested with the SacI/AleI restriction enzymes (Thermo scientific). This restriction removed the variable region, CH1 and hinge regions and the heavy chain leader. The nucleic acid sequence of the K-modified AChE-spacer-hinge (encoding the amino acid sequence denoted by SEQ ID NO: 13 fused N-terminal to the amino acid sequence denoted by SEQ ID NO: 14, Table 2) was also digested with the same restriction enzymes and then ligated to the digested vector, resulting in cloning (fusion) of the K-modified AChE-hinge N-terminal to the Fc portion (having the amino acid sequence denoted by SEQ ID NO: 15, Table 2). This step resulted in a nucleic acid having the sequence denoted by SEQ ID NO: 18 (Table 2 and FIG. 2) that encodes the polypeptide having the amino acid sequence denoted by SEQ ID NO: 16 (also referred to herein as the "K-NL1 fusion protein"). Upon cleavage of the K leader sequence in the host cell the resulting fusion polypeptide has the amino acid sequence denoted by SEQ ID NO: 17. The sequences are presented in Table 2 above.

The nucleic acid encoding a fusion protein comprising the native signal peptide of human AChE, the modified AChE and the spacer unit and Fc domain described above is denoted by SEQ ID NO: 19.

Single-stranded DNA of the fusion construct was prepared using Big Dye (Applied Biosystems) and the PCR products were analyzed with ABI PRISM 310 Genetic Analyzer (Applied Biosystems) to verify the integrity of the construct. Sequencing of the nucleic acid of the construct encoding the fusion polypeptide comprising the K-modified AChE-spacer-Fc domain, also referred to herein as the "K-NL1 fusion protein" confirmed that it comprises all the desired portions (namely the Kappa-leader sequence, the modified AChE, the spacer and the Fc domain including the hinge region, as described above). ELISA assay was used to confirm that the AChE part of the protein is active, as described below.

Polypeptide Expression and Purification

The plasmid (40 µg) comprising the nucleic acid sequence of the K-NL1 fusion construct was transiently transfected to FreeStyle HEK293 cells (30 ml, 1×10$^6$ cells/ml) (Life technology) and the supernatant was collected after seven days. Cell-culture supernatants were adsorbed to procainamide SEPHAROSE (a cross-linked, beaded form of agarose) 4B columns (4000 units/ml resin) which were then rinsed with 50 mM sodium phosphate buffer, pH 8.0/1 mM EDTA and again with 50 mM sodium phosphate buffer, pH 8.0/0.4 M NaCl/1 mM EDTA. Enzyme elution was performed with decamethonium (Sigma, 0.02 M) in 50 mM sodium phosphate buffer, pH 8.0/1 mM EDTA. Leader sequences are cleaved off prior to secretion and therefore the resulting protein, named the "NL1 fusion protein", comprised the modified AChE fused at the N-terminal to the Fc domain, where the modified AChE and the Fc domain are covalently linked by the spacer ASEAP. The amino acid sequence of the NL1 fusion protein is denoted by SEQ ID NO: 17 (Table 2 above). The concentration of each enzyme was determined using 7-(methylethoxyphosphinyloxy)-1-methylquinolinium iodide (MEPQ, prepared in-house as previously described (3)) titration. Briefly, active site titration of enzyme solutions was performed in the presence of 0.1 mg/ml BSA in 50 mM sodium phosphate buffer, pH 8.0, by adding various amounts of MEPQ Inhibition was allowed to proceed to completion and the residual activity was plotted against the concentration of inhibitor.

ELISA Assay

In order to assess the activity of the AChE after fusion to Fc (namely the NL1 fusion protein) and to verify that the obtained fusion AChE enzyme indeed comprises the Fc domain at the protein level, an ELISA assay was performed as described below. Maxisorp 96-well microtiter plates (Nunc) were coated with 2 µg/ml anti-human Fc antibody (50 µl/well, Goat anti-human IgG, FC specific, Sigma #I3391). The plates were then washed and blocked with PBST buffer (0.05% Tween 20, 2% BSA in PBS) at room temperature for one hour. NL1 fusion protein samples, directly obtained from the cell-culture supernatant or purified fractions (0.4-10 pM) were added to the wells and incubated for another hour. Elman's substrate mix (comprising 50 mM phosphate buffer pH 8, 0.1 mg/ml BSA, 1 mM Acetyl-thio-cholin (ATC), Sigma #A5751) and 0.6 mM dithiobisnitro-benzoate (DTNB, Sigma #D8130) was prepared and 100 µl were added to each well at the end of the incubation. This mix serves as a substrate for AChE and thus allows monitoring of its activity. The substrate hydrolysis was monitored by repeated spectrophotometric readings (412-650 nm) for 5 min, at 45 sec intervals using a spectrophotometer (VERSAmax microplate reader, Molecular Devices).

Western Blot Analysis

A sample of HEK293 cells expressing the NL1 fusion protein (namely cells transfected with the plasmid encoding the K-NL1 fusion protein), was boiled in 1× sample buffer (Bio-Rad) with or without β-mercaptoethanol, and loaded onto 4-12% pre-casted SDS-PAGE gel (Invitrogen). Antibodies used for detection: 1:100 mouse anti-HuAChE followed by 1:1000 rabbit anti-mouse IgG-AP (Sigma #A1902), or 1:1000 goat anti-human IgG (Fc specific) (Sigma #A9544).

Organophosphate Inhibitors

Sarin (O-isopropyl methylphosphonofluoridate) and VX (O-ethyl-S-(2-isopropylaminoethyl) methylphosphonothiolate, were prepared as previously described. (3). The purity of the OPs (>95%) was determined by 1H and 31P NMR spectroscopy. Stock solutions were kept at −20° C., and diluted in sodium phosphate buffer to the desired concentration, prior to use.

Kinetic Studies

AChE enzymatic activity was assayed as described before (11) in the presence of AChE substrate buffer (0.1 mg/ml BSA, 0.3 mM 5,5-dithio-bis-(2-nitrobenzoic acid) (DTNB), 50 mM sodium phosphate buffer (pH 8.0), and 0.5 mM Acetyl-thio-cholin (ATC, sigma) at 27° C. and monitored with a Thermomax microplate reader (Molecular Devices). Measurements of phosphorylation rates were carried out by monitoring residual activity (E) at various time points, following incubation of the enzyme in the presence of at least four different concentrations of an OP-inhibitor (I). The apparent bimolecular phosphorylation rate constants (ki) determined under pseudo first-order conditions were computed from the plot of slopes of ln(E) versus time at different inhibitor concentrations (12). Rate constants under second order conditions were determined from plots of ln {E/[I0−(E0−E)]} versus time.

Inhibition constants (KO by AChE and AChE-Fc were assayed as described before (3), by monitoring residual activity at various time points, after incubation of the enzymes in the presence of at least three different concentrations of propidium (3,8 diamino-5-3'-(trimethylammonium)propyl-6-phenylphenanthridniumiodide (Sigma) or BW284C51 (di(p-allyl-N-methylaminophenyl)pentan) (Sigma).

In Vivo Kinetics

Female outbred ICR mice (Charles River Laboratories) were maintained at 20-22° C. and a relative humidity of 50±10% on a 12-h light/dark cycle, fed with commercial rodent chow (Koffolk Inc.) and provided with tap water ad libitum. Treatment of animals was in accordance with regulations outlined in the USDA Animal Welfare Act and the conditions specified in Guide for Care and Use of Laboratory Animals (National Institute of Health, 1996). Animal studies were approved by the local ethical committee on animal experiments.

Pharmacokinetic experiments in mice (three mice, 26-28 gr, per enzyme sample) were carried out essentially as described previously (3). Briefly, mice were injected intravenously with native human AChE (HuAChE, to reach 30-fold increase over endogenous background levels) or with AChE-Fc in 0.2 ml PBS. At different time points, blood samples (5 μl) were drawn from the tail vein, diluted 20-fold in PBS, and centrifuged for three minutes at 3000 rpm for the removal of red blood cells. The levels of native HuAChE in each sample were determined as described above and expressed as the percent of the initial concentration at time zero (background levels of endogenous AChE activity were subtracted from all measurements). The levels of AChE-Fc in each sample were determined using captured ELISA, as follows: Maxisorp 96-well microtiter plates (Nunc, Roskilde, Denmark) were coated overnight with 5 μg/ml of anti-human Fc F(ab)$_2$ fragments antibody (sigma; 50 μl/well) in NaHCO$_3$ buffer (50 mM, pH 9.6), washed and blocked with PBST buffer at room temperature for one hour. Samples were serially diluted in PBST, added to the coated plates and incubated for one hour at 37° C. Plates were then washed with PBST, incubated with the AChE substrate buffer and color formation was monitored as described below. Values of AChE-Fc are expressed as the percent of the initial concentration at time zero. Pharmacokinetic parameters were calculated using the Prism software (GraphPad Software Inc., USA).

Example 1

Preparation of an AChE-Fc Fusion Protein Using a K-Leader Sequence

As indicated above, choline esterases have short half lives in the human circulation system. In order to prolong the circulatory life-time of Acetylcholinesterase (AChE), an AchE was fused to the Fc domain of human IgG1, as described above.

First, a AChE-Fc fusion protein construct was prepared by fusing a modified AChE, which lacks both its N-terminal signal peptide and its C-terminal tail, to the Fc domain of human IgG1 using the K-leader sequence as a secretion signal sequence.

Briefly, a modified AChE was prepared by deleting the N-terminal signal peptide and the C-terminal 40 amino acid residues from the native human AChE enzyme (the amino acid of the native human AChE is denoted for example by SEQ ID NO: 21). The resulting modified AChE (denoted by SEQ ID NO: 8) was fused through its C-terminus to a short peptide spacer having the amino acid sequence ASEAP (denoted by SEQ ID NO: 9, Table 2), resulting in a polypeptide construct having the amino acid sequence denoted by SEQ ID NO: 10 (Table 2).

A sequence encoding the human Kappa-leader sequence having the amino acid sequence denoted by SEQ ID NO: 11 (Table 2) was then added to the 5' end of the sequence encoding the modified AChE that is in turn linked to the spacer, thereby obtaining the polypeptide K-Modified AChE-spacer, the amino acid sequence of which is denoted by SEQ ID NO: 13 (Table 2).

Fusion of the above polypeptide to the Fc domain of human IgG1 was performed in a two-step procedure, as described above, resulting in a fusion polypeptide (also termed herein the "NL1 fusion protein") that comprises from it N-terminal to it C-terminal end the modified AChE, and the Fc domain of human IgG1 linked via a spacer (ASEAP) situated between the modified AChE and the Fc domain of human IgG1.

The amino acid sequence of the above modified AChE-Fc fusion protein comprising the spacer is shown in FIG. 1A for a construct comprising the amino acid residues of the kappa leader sequence (also termed herein the K-NL1 fusion protein) and in FIG. 1B for a construct from which the kappa leader sequence was deleted (termed herein NL1 fusion protein). The nucleic acid sequence encoding the above modified AChE-Fc fusion protein comprising the Kappa-leader sequence and the spacer (namely the K-NL1 fusion protein) is shown in FIG. 2.

Sequencing of NL1 fusion protein confirmed that it comprises all of the desired portions (AChE, Fc).

As shown in FIG. 3, a Western blot analysis performed with protein samples of the modified AChE-Fc fusion protein prepared as described above (the NL1 fusion protein) confirm that the NL1 fusion protein indeed comprises both AChE and Fc and that the fusion protein is a dimer of about 250 KDa under non-reducing conditions (namely in the absence of β-mercaptoethanol). Without wishing to be bound by theory, the polypeptide is expressed as a monomer and a stable dimer is formed by non-covalent interactions.

Figure 4:
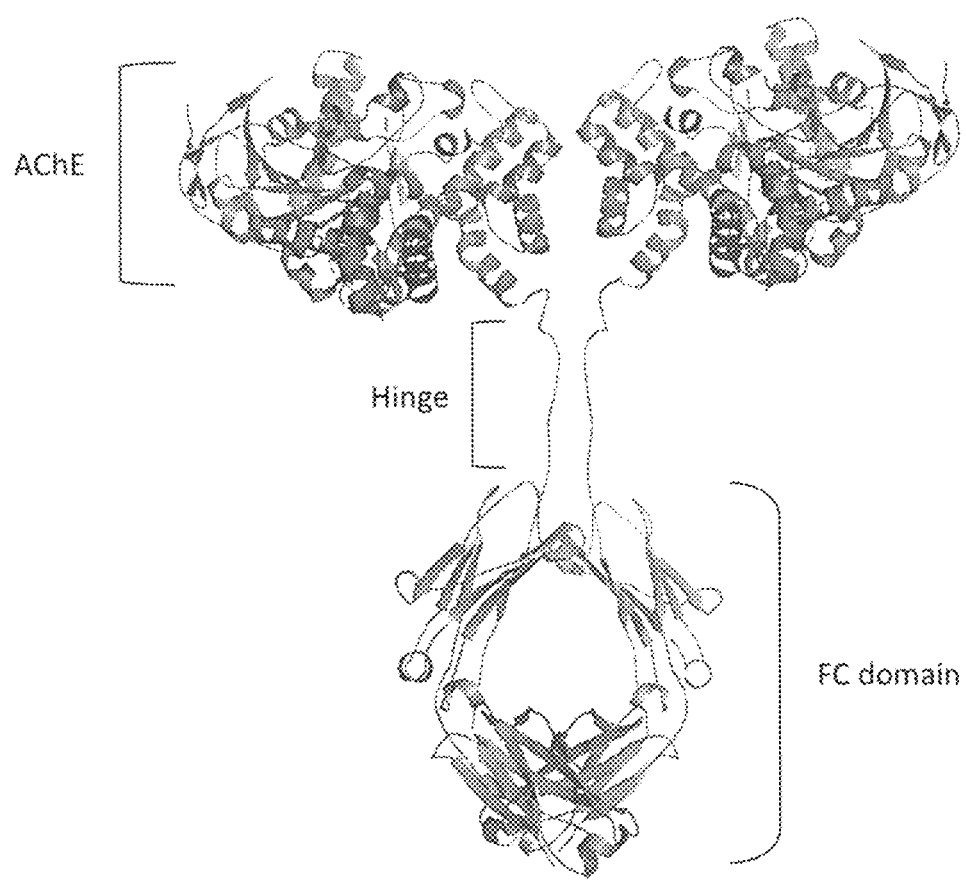
FIG. 4 is a schematic representation (ribbon diagram) of the NL1 fusion protein comprising the modified AChE fused to a spacer (at the hinge region) and to Fc fusion protein, at a dimeric form.
Figure 6:
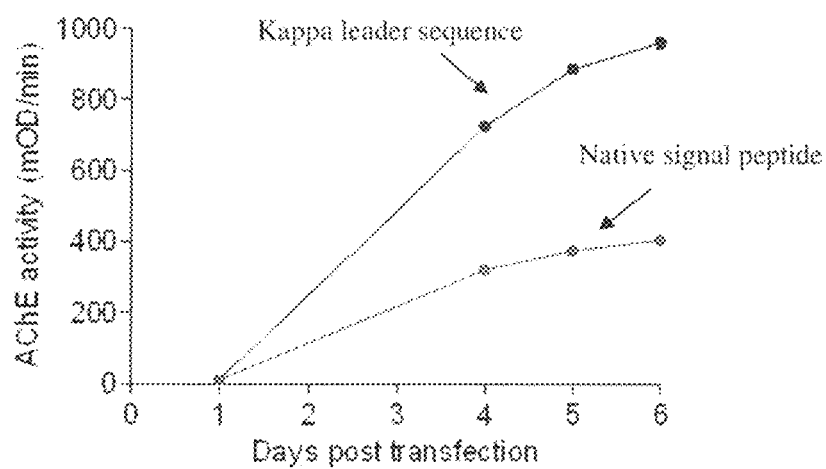
FIG. 6 shows expression profiles of AChE-Fc fusion protein (presented as AChE activity mOD/minute) generated using transient expression of HEK293 cells that were transfected with vector containing either kappa-light chain or the native signal peptide of human AChE (HuAChE), as indicated. Points are average±SEM of triplicate analysis.

A schematic presentation (ribbon diagram) of the NL1 fusion protein is provided in FIG. 4. The upper right and left side "arms" of the polypeptide schematically shown in FIG. 4 represent the two monomers of the modified AChE. Each monomer of the modified AChE is independently covalently linked to the Fc domain (lower panel of FIG. 4) through a spacer peptide, situated at the hinge region. In other words, the designed protein comprises a homodimer of two human AChE enzymatic moieties, where each one of the two AChE moieties is independently fused to a human Fc (HuFc) moiety, resulting in a 250 kDa molecule.

Example 2

Preparation of an AChE-Fc Fusion Protein Using the Signal Peptide of Native AChE A construct containing the NL1 protein, linked to the AChE native signal peptide instead of the Kappa leader (also termed herein the SP-NL1 fusion protein), was synthesized by Integrated DNA Technologies (IDT). In other words, the K-leader sequence was replaced by the native AChE signal peptide. The amino acid sequence of the AChE signal peptide is denoted by SEQ ID NO: 12.

The construct was cloned to the expression vector, as described above for K-NL1, and transiently transfected into HEK293 cells. The nucleic acid sequence construct encoding the SP-NL1 fusion protein is denoted by SEQ ID NO: 19 (Table 2) and is shown in FIG. 5. The resulting protein expressed as well as K-NL1.

As demonstrated in FIG. 6, both vectors, namely the vector with the AChE native signal peptide and the vector with the Kappa leader sequence, could induce the secretion of active fusion protein, yet the levels obtained by transfecting with the vector containing the Kappa light-chain signal peptide sequence were two fold higher.

Example 3

ELISA Activity Assay of the AChE-Fc Fusion Protein

First, in order to verify that the obtained fusion AChE enzyme indeed comprises the Fc domain at the protein level and that the resulting fusion polypeptide is active, an ELISA assay was performed as described above.

As shown in FIG. 7A, an active AChE-Fc fusion protein can be seen in the supernatant of the HEK293 cells that were transiently transfected with the plasmid encoding for the fusion protein (using the SP-NL1 construct). Similar results were obtained using the purified AChE-Fc fusion protein that was obtained from transfecting cells with a plasmid encoding the K-NL1 fusion protein construct (FIG. 7B).

Example 4

Pharmacokinetic Analysis of the AChE Fusion Protein in Mice

The therapeutic use of the AChE-Fc fusion protein prepared as described above requires both an efficient enzymatic function as well as extended plasma half-life. In order to assess the pharmacokinetic characteristics (half-life) of the AChE fusion protein prepared as described above it was first necessary to establish a specific and sensitive assay that will enable monitoring the circulatory levels of the AChE-Fc with minimal interferences from endogenous AChE that naturally resides in the blood. To that end, a functional capture ELISA assay was designed, as detailed above.

Briefly, plates were coated with antibodies directed against the human Fc for immobilization of the AChE-Fc present in blood samples, as schematically shown in FIG. 8. Then, plates were washed and the specific AChE substrate Acetyl-thio-cholin (ATC) was added for colorimetric kinetic detection of the enzyme according to a previously reported protocol (11). As shown in FIG. 8, the assay exhibited a clear dose response between the concentration of AChE-Fc and color formation and high sensitivity of detection of the fusion protein at the sub pM concentration range. Owing to the specificity of the assay format, control naïve serum samples did not induce any color formation (virtually zero background). These results indicated that the novel assay can be used to monitor the AChE-Fc levels in mice serum.

The above functional capture ELISA assay was then used for assessing the AChE-Fc fusion protein blood levels in vivo, in mice. As detailed above, AChE-Fc, as well as HuAChE (the native AChE), were administered intravenously to mice, and their pharamacokinetic profiles were determined.

As shown in FIG. 9, the AChE (native enzyme) cleared rapidly from the blood stream, with a half life 03) of about 30 min (Table 3 below) and mean resident time (MRT) value of 40 min, in good agreement with previously reported data (13). The AChE-Fc, however, exhibited a totally different profile with significantly longer circulatory lifetime which was 100-fold slower than the native enzyme. As presented in Table 3 below, 99% of the AChE-Fc molecules have a half life of 4000 min and the overall calculated MRT value is about 6000 min

TABLE 3

Pharmacokinetic parameters of AChE and AChE-Fc in mice blood[a]

| | rHuAChE | AChE-Fc |
|---|---|---|
| Distribution phase | | |
| $t_{1/2\alpha}$ (min) | 1 ± 0.4 | 47 ± 18 |
| AUC (%)[b] | 6 | 1 |
| Elimination phase | | |
| $t_{1/2\beta}$ (min) | 29 ± 3 | 4020 ± 800 |
| AUC (%)[b] | 94 | 99 |
| MRT (min) | 40 ± 4 | 5800 ± 1100 |

[a]Presented data is average ± SEM of 3 mice for each enzyme.
[b]The percentage each term contributes to the area under the curve.

The prolonged half-life of the AChE-Fc fusion protein prepared as described above provides a clear prophylactic potential for scavenging compounds targeting the AChE enzyme (e.g. organophosphate compounds) from the circulatory system for as long as 60 hours, or more, after its injection.

Example 5

Kinetic Analysis of the AChE Fusion Protein

In order to verify that the AChE-Fc fusion protein has retained the catalytic activity of the native AChE enzyme, an in vitro kinetic analysis was performed as described above and it was found that both enzymes share the same kinetic hydrolysis parameters toward Acetyl-thio-cholin (ATC, Table 4).

In order to further evaluate whether the structure of the enzymatic moiety remained intact, the interactions of AChE-Fc with propidium, a peripheral anionic site ligand and with the bis-quaternary inhibitor BW284c51 whose binding site spans both the peripheral and the active-center gorge, were measured. The fusion protein displayed high affinity toward these two ligands, with similar values as the native enzyme (Table 4).

In addition, the bioscavenging potential of AChE-Fc toward various nerve agents was examined. To that end, the reactivity of the fusion protein towards sarin, a representative of the "G-agents" oragnophosphonates was determined. The apparent bimolecular rate constant ($k_i$) of AChE-Fc towards sarin was found to be $11.5 \times 10^5 M^{-1}$ min, indicating that it retained its full bioscavenging activity as the HuAChE (Table 4). Similarly, both AChE-Fc and HuAChE exhibit similar inhibition rate constants toward VX, a charged oragnophosphonate of the "V-agents", with $k_i$ of 400 and $450 \times 10^5 M^{-1}$ min$^{-1}$, respectively (Table 4).

TABLE 4

Rate constants of ATC hydrolysis, enzyme inhibition and phosphorylation of AChE and AChE-Fc

| | ATC | | | $K_i$ | | | |
|---|---|---|---|---|---|---|---|
| | $K_m$ (mM) | $K_{cat}$ ($\times 10^{-5}$ min$^{-1}$) | $K_{app}$ ($\times 10^8$ M$^{-1}$min$^{-1}$) | Propidium ($\mu$M)$^a$ | BW284c5 (nM)$^a$ | VX ($\times 10^5$ M$^{-1}$min$^{-1}$)$^b$ | Sarin |
| HuAChE | 0.19 | 5.2 | 27 | 12.5 | 17.8 | 450 | 10.3 |
| AChE-Fc | 0.18 | 4.5 | 25 | 11.1 | 19.2 | 400 | 11.5 |

$^a$Enzyme inhibition constant
$^b$Apparent bimolecular rate constant for phosphylation Taken together the above results demonstrate that the AChE-Fc conjugate polypeptide maintained its reactivity towards various ligands and organophosphates and is a potential candidate as a prophylactic and scavenging agent against compounds targeting the AChE enzyme.

The invention claimed is:

1. A fusion polypeptide comprising:
   (a) an acetylcholinesterase (AChE) polypeptide component consisting of a modified human AChE polypeptide of SEQ ID NO: 8 or a variant thereof, wherein said variant (i) is not full length human AChE and (ii) is an N-terminal and C-terminal truncated version of human AChE; and (b) a fragment crystallizable (Fc) domain of human IgG or variants thereof, wherein the fusion polypeptide retains the functional activity of human AChE.

2. The fusion polypeptide according to claim 1, wherein said Fc domain comprises an amino acid sequence that is at least 70% identical to the amino acid sequence denoted by SEQ ID NO: 15 and wherein said Fc domain retains its functional activity.

3. The fusion polypeptide according to claim 1, wherein said fusion polypeptide comprises a dimer of two identical monomers, wherein each one of the identical monomers comprises an acetylcholinesterase (AChE) polypeptide component and an Fc domain of human IgG.

4. The fusion polypeptide according to claim 1, wherein said fusion polypeptide comprises a dimer of a first and second monomers, wherein said first monomer comprises an AChE polypeptide component and an Fc domain of human IgG and said second monomer comprises an Fc domain of human IgG.

5. The fusion polypeptide according to claim 1, wherein said fusion polypeptide further comprises a spacer covalently linking the AChE polypeptide component and the Fc domain of human IgG.

6. A fusion polypeptide, comprising:
(a) an acetylcholinesterase (AChE) polypeptide component comprising of a modified human AChE polypeptide having an amino acid sequence denoted by SEQ ID NO: 8 or variants thereof; and
(b) a fragment crystallizable (Fc) domain of human IgG or variants thereof, wherein the fusion polypeptide retains the functional activity of human AChE and further comprises a spacer covalently linking the AChE polypeptide component and the Fc domain of human IgG, and wherein said spacer comprises or consists of the amino acid sequence ASEAP denoted by SEQ ID NO: 9.

7. The fusion polypeptide according to claim 1, wherein said modified human AChE polypeptide comprises an amino acid sequence that is at least 70% identical to the amino acid sequence denoted by SEQ ID NO: 8 and wherein said human AChE polypeptide component retains the functional activity of human AChE.

8. The fusion polypeptide according to claim 1, wherein said modified human AChE polypeptide comprises an amino acid substitution in at least one position of SEQ ID NO: 8 and wherein said human AChE polypeptide component retains the functional activity of human AChE.

9. The fusion polypeptide according to claim 8, wherein said modified human AChE polypeptide comprises the amino acid Ala at a position corresponding to position 338 of the amino acid sequence denoted by SEQ ID NO: 8.

10. The fusion polypeptide according to claim 1, wherein said modified human AChE polypeptide consists of the amino acid sequence denoted by SEQ ID NO: 8.

11. A fusion polypeptide, comprising:
(a) an acetylcholinesterase (AChE) polypeptide component comprising a modified human AChE polypeptide having an amino acid sequence denoted by SEQ ID NO: 8; and
(b) a fragment crystallizable (Fc) domain of human IgG or variants thereof, wherein the fusion polypeptide retains the functional activity of human AChE and wherein said fusion polypeptide comprises the amino acid sequence denoted by SEQ ID NO: 17.

12. A pharmaceutical composition comprising the fusion polypeptide according to claim 1 and a pharmaceutically acceptable carrier.

13. A method of prophylaxis of organophosphate poisoning comprising administering an effective amount of the fusion polypeptide according to claim 1 or a pharmaceutical composition comprising thereof to a subject in need thereof.

14. The method according to claim 13, wherein said method further comprises administering at least one additional therapeutic agent.

15. A method of increasing the circulatory half-life of AChE, said method comprising preparing a fusion polypeptide of claim 1.

16. A kit comprising:
(i) at least one fusion polypeptide of claim 1; and
(ii) instructions for use.

17. The kit according to claim 16, wherein said kit further comprises at least one additional therapeutic agent.

* * * * *

SEQUENCE LISTING

<160> NUMBER OF SEQ ID NOS: 26

<210> SEQ ID NO 1
<211> LENGTH: 50
<212> TYPE: DNA
<213> ORGANISM: Artificial Sequence
<220> FEATURE:
<223> OTHER INFORMATION: Forward primer K-AChET1
<220> FEATURE:
<221> NAME/KEY: misc_feature
<223> OTHER INFORMATION: Synthetic

<400> SEQUENCE: 1
ctcctgctgc tctggctgcc cggggccaaa tgtgagggcc gggaggatgc     50

<210> SEQ ID NO 2
<211> LENGTH: 62
<212> TYPE: DNA
<213> ORGANISM: Artificial Sequence
<220> FEATURE:
<223> OTHER INFORMATION: Forward primer HuK2
<220> FEATURE:
<221> NAME/KEY: misc_feature
<223> OTHER INFORMATION: Synthetic

<400> SEQUENCE: 2
tataagcaga gctcatggac atgagggccc atgtgcacct tctgggctc ctgctgctct     60 gg     62

<210> SEQ ID NO 3
<211> LENGTH: 31
<212> TYPE: DNA
<213> ORGANISM: Artificial Sequence
<220> FEATURE:
<223> OTHER INFORMATION: Reverse primer AChET
<220> FEATURE:
<221> NAME/KEY: misc_feature
<223> OTHER INFORMATION: Synthetic

<400> SEQUENCE: 3
gagcctccga ggcggtggcg ctgagcaatt t                                          31

<210> SEQ ID NO 4
<211> LENGTH: 49
<212> TYPE: DNA
<213> ORGANISM: Artificial Sequence
<220> FEATURE:
<223> OTHER INFORMATION: Reverse primer AChET-h2
<220> FEATURE:
<221> NAME/KEY: misc_feature
<223> OTHER INFORMATION: Synthetic

<400> SEQUENCE: 4
gagttttgtc actagatttg ggctcgggag cctccgaggc ggtggcgct                       49

<210> SEQ ID NO 5
<211> LENGTH: 35
<212> TYPE: DNA
<213> ORGANISM: Artificial Sequence
<220> FEATURE:
<223> OTHER INFORMATION: Foward primer AChET hinge
<220> FEATURE:
<221> NAME/KEY: misc_feature
<223> OTHER INFORMATION: Synthetic

<400> SEQUENCE: 5
gcctcggagg ctcccgagcc caaatctagt gacaa                                      35

<210> SEQ ID NO 6
<211> LENGTH: 33
<212> TYPE: DNA
<213> ORGANISM: Artificial Sequence
<220> FEATURE:
<223> OTHER INFORMATION: Forward primer HuK-ChE
<220> FEATURE:
<221> NAME/KEY: misc_feature
<223> OTHER INFORMATION: Synthetic

<400> SEQUENCE: 6
tataagcaga gctcatggac atgagggccc atg                                        33

<210> SEQ ID NO 7
<211> LENGTH: 19
<212> TYPE: DNA
<213> ORGANISM: Artificial Sequence
<220> FEATURE:
<223> OTHER INFORMATION: Reverse Primer Hinge
<220> FEATURE:
<221> NAME/KEY: misc_feature
<223> OTHER INFORMATION: Synthetic

<400> SEQUENCE: 7
gtccaccacc acgcatgtg                                                        19

<210> SEQ ID NO 8
<211> LENGTH: 543
<212> TYPE: PRT
<213> ORGANISM: Artificial Sequence
<220> FEATURE:
<223> OTHER INFORMATION: Amino acid sequence of the Modified AChE
<220> FEATURE:
<221> NAME/KEY: misc_feature
<223> OTHER INFORMATION: Synthetic

<400> SEQUENCE: 8

Glu Gly Arg Glu Asp Ala Glu Leu Leu Val Thr Val Arg Gly Gly Arg
1               5                   10                  15

Leu Arg Gly Ile Arg Leu Lys Thr Pro Gly Gly Pro Val Ser Ala Phe

```
                     20                  25                  30
Leu Gly Ile Pro Phe Ala Glu Pro Met Gly Pro Arg Arg Phe Leu
            35                  40                  45
Pro Pro Glu Pro Lys Gln Pro Trp Ser Gly Val Val Asp Ala Thr Thr
 50                  55                  60
Phe Gln Ser Val Cys Tyr Gln Tyr Val Asp Thr Leu Tyr Pro Gly Phe
 65                  70                  75                  80
Glu Gly Thr Glu Met Trp Asn Pro Asn Arg Glu Leu Ser Glu Asp Cys
                85                  90                  95
Leu Tyr Leu Asn Val Trp Thr Pro Tyr Pro Arg Pro Thr Ser Pro Thr
                100                 105                 110
Pro Val Leu Val Trp Ile Tyr Gly Gly Phe Tyr Ser Gly Ala Ser
            115                 120                 125
Ser Leu Asp Val Tyr Asp Gly Arg Phe Leu Val Gln Ala Glu Arg Thr
            130                 135                 140
Val Leu Val Ser Met Asn Tyr Arg Val Gly Ala Phe Gly Phe Leu Ala
145                 150                 155                 160
Leu Pro Gly Ser Arg Glu Ala Pro Gly Asn Val Gly Leu Leu Asp Gln
                165                 170                 175
Arg Leu Ala Leu Gln Trp Val Gln Glu Asn Val Ala Ala Phe Gly Gly
                180                 185                 190
Asp Pro Thr Ser Val Thr Leu Phe Gly Glu Ser Ala Gly Ala Ala Ser
                195                 200                 205
Val Gly Met His Leu Leu Ser Pro Pro Ser Arg Gly Leu Phe His Arg
            210                 215                 220
Ala Val Leu Gln Ser Gly Ala Pro Asn Gly Pro Trp Ala Thr Val Gly
225                 230                 235                 240
Met Gly Glu Ala Arg Arg Arg Ala Thr Gln Leu Ala His Leu Val Gly
                245                 250                 255
Cys Pro Pro Gly Gly Thr Gly Gly Asn Asp Thr Glu Leu Val Ala Cys
                260                 265                 270
Leu Arg Thr Arg Pro Ala Gln Val Leu Val Asn His Glu Trp His Val
            275                 280                 285
Leu Pro Gln Glu Ser Val Phe Arg Phe Ser Phe Val Pro Val Val Asp
            290                 295                 300
Gly Asp Phe Leu Ser Asp Thr Pro Glu Ala Leu Ile Asn Ala Gly Asp
305                 310                 315                 320
Phe His Gly Leu Gln Val Leu Val Gly Val Val Lys Asp Glu Gly Ser
                325                 330                 335
Tyr Phe Leu Val Tyr Gly Ala Pro Gly Phe Ser Lys Asp Asn Glu Ser
                340                 345                 350
Leu Ile Ser Arg Ala Glu Phe Leu Ala Gly Val Arg Val Gly Val Pro
            355                 360                 365
Gln Val Ser Asp Leu Ala Ala Glu Ala Val Val Leu His Tyr Thr Asp
            370                 375                 380
Trp Leu His Pro Glu Asp Pro Ala Arg Leu Arg Glu Ala Leu Ser Asp
385                 390                 395                 400
Val Val Gly Asp His Asn Val Val Cys Pro Val Ala Gln Leu Ala Gly
                405                 410                 415
Arg Leu Ala Ala Gln Gly Ala Arg Val Tyr Ala Tyr Val Phe Glu His
                420                 425                 430
Arg Ala Ser Thr Leu Ser Trp Pro Leu Trp Met Gly Val Pro His Gly
            435                 440                 445
```

-continued

```
Tyr Glu Ile Glu Phe Ile Phe Gly Ile Pro Leu Asp Pro Ser Arg Asn
            450                 455                 460

Tyr Thr Ala Glu Glu Lys Ile Phe Ala Gln Arg Leu Met Arg Tyr Trp
465                 470                 475                 480

Ala Asn Phe Ala Arg Thr Gly Asp Pro Asn Glu Pro Arg Asp Pro Lys
            485                 490                 495

Ala Pro Gln Trp Pro Pro Tyr Thr Ala Gly Ala Gln Gln Tyr Val Ser
            500                 505                 510

Leu Asp Leu Arg Pro Leu Glu Val Arg Arg Gly Leu Arg Ala Gln Ala
            515                 520                 525

Cys Ala Phe Trp Asn Arg Phe Leu Pro Lys Leu Leu Ser Ala Thr
530                 535                 540
```

<210> SEQ ID NO 9
<211> LENGTH: 5
<212> TYPE: PRT
<213> ORGANISM: Artificial Sequence
<220> FEATURE:
<223> OTHER INFORMATION: Amino acid sequence of the spacer
<220> FEATURE:
<221> NAME/KEY: misc_feature
<223> OTHER INFORMATION: Synthetic

<400> SEQUENCE: 9

```
Ala Ser Glu Ala Pro
1               5
```

<210> SEQ ID NO 10
<211> LENGTH: 548
<212> TYPE: PRT
<213> ORGANISM: Artificial Sequence
<220> FEATURE:
<223> OTHER INFORMATION: Amino acid sequence of the Modified AChE fused
      to a spacer
<220> FEATURE:
<221> NAME/KEY: misc_feature
<223> OTHER INFORMATION: Synthetic

<400> SEQUENCE: 10

```
Glu Gly Arg Glu Asp Ala Glu Leu Leu Val Thr Val Arg Gly Gly Arg
1               5                   10                  15

Leu Arg Gly Ile Arg Leu Lys Thr Pro G

```
Leu Pro Gly Ser Arg Glu Ala Pro Gly Asn Val Gly Leu Leu Asp Gln
            165                 170                 175

Arg Leu Ala Leu Gln Trp Val Gln Glu Asn Val Ala Ala Phe Gly Gly
        180                 185                 190

Asp Pro Thr Ser Val Thr Leu Phe Gly Glu Ser Ala Gly Ala Ala Ser
    195                 200                 205

Val Gly Met His Leu Leu Ser Pro Ser Arg Gly Leu Phe His Arg
210                 215                 220

Ala Val Leu Gln Ser Gly Ala Pro Asn Gly Pro Trp Ala Thr Val Gly
225                 230                 235                 240

Met Gly Glu Ala Arg Arg Arg Ala Thr Gln Leu Ala His Leu Val Gly
                245                 250                 255

Cys Pro Pro Gly Gly Thr Gly Gly Asn Asp Thr Glu Leu Val Ala Cys
            260                 265                 270

Leu Arg Thr Arg Pro Ala Gln Val Leu Val Asn His Glu Trp His Val
        275                 280                 285

Leu Pro Gln Glu Ser Val Phe Arg Phe Ser Phe Val Pro Val Val Asp
    290                 295                 300

Gly Asp Phe Leu Ser Asp Thr Pro Glu Ala Leu Ile Asn Ala Gly Asp
305                 310                 315                 320

Phe His Gly Leu Gln Val Leu Val Gly Val Val Lys Asp Glu Gly Ser
                325                 330                 335

Tyr Phe Leu Val Tyr Gly Ala Pro Gly Phe Ser Lys Asp Asn Glu Ser
            340                 345                 350

Leu Ile Ser Arg Ala Glu Phe Leu Ala Gly Val Arg Val Gly Val Pro
        355                 360                 365

Gln Val Ser Asp Leu Ala Ala Glu Ala Val Val Leu His Tyr Thr Asp
    370                 375                 380

Trp Leu His Pro Glu Asp Pro Ala Arg Leu Arg Glu Ala Leu Ser Asp
385                 390                 395                 400

Val Val Gly Asp His Asn Val Val Cys Pro Val Ala Gln Leu Ala Gly
                405                 410                 415

Arg Leu Ala Ala Gln Gly Ala Arg Val Tyr Ala Tyr Val Phe Glu His
            420                 425                 430

Arg Ala Ser Thr Leu Ser Trp Pro Leu Trp Met Gly Val Pro His Gly
        435                 440                 445

Tyr Glu Ile Glu Phe Ile Phe Gly Ile Pro Leu Asp Pro Ser Arg Asn
    450                 455                 460

Tyr Thr Ala Glu Glu Lys Ile Phe Ala Gln Arg Leu Met Arg Tyr Trp
465                 470                 475                 480

Ala Asn Phe Ala Arg Thr Gly Asp Pro Asn Glu Pro Arg Asp Pro Lys
                485                 490                 495

Ala Pro Gln Trp Pro Pro Tyr Thr Ala Gly Ala Gln Gln Tyr Val Ser
            500                 505                 510

Leu Asp Leu Arg Pro Leu Glu Val Arg Arg Gly Leu Arg Ala Gln Ala
        515                 520                 525

Cys Ala Phe Trp Asn Arg Phe Leu Pro Lys Leu Leu Ser Ala Thr Ala
    530                 535                 540

Ser Glu Ala Pro
545

<210> SEQ ID NO 11
<211> LENGTH: 22
<212> TYPE: PRT
```

<213> ORGANISM: Homo sapiens

<400> SEQUENCE: 11

Met Asp Met Arg Ala His Val His Leu Leu Gly Leu Leu Leu Leu Trp
1               5                   10                  15

Leu Pro Gly Ala Lys Cys
            20

<210> SEQ ID NO 12
<211> LENGTH: 31
<212> TYPE: PRT
<213> ORGANISM: Homo sapiens

<400> SEQUENCE: 12

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala
            20                  25                  30

<210> SEQ ID NO 13
<211> LENGTH: 570
<212> TYPE: PRT
<213> ORGANISM: Artificial Sequence
<220> FEATURE:
<223> OTHER INFORMATION: Kappa-leader sequence fused to modified AChE
      that is fused to a spacer (K-Modified AChE-spacer)
<220> FEATURE:
<221> NAME/KEY: misc_feature
<223> OTHER INFORMATION: Synthetic

<400> SEQUENCE: 13

Met Asp Met Arg Ala His Val His Leu Leu Gly Leu Leu Leu Leu Trp
1               5                   10                  15

Leu Pro Gly Ala Lys Cys Glu Gly Arg Glu Asp Ala Glu Leu Leu Val
            20                  25                  30

Thr Val Arg Gly Gly Arg Leu Arg Gly Ile Arg Leu Lys Thr Pro Gly
        35                  40                  45

Gly Pro Val Ser Ala Phe Leu Gly Ile Pro Phe Ala Glu Pro Pro Met
    50                  55                  60

Gly Pro Arg Arg Phe Leu Pro Pro Glu Pro Lys Gln Pro Trp Ser Gly
65                  70                  75                  80

Val Val Asp Ala Thr Thr Phe Gln Ser Val Cys Tyr Gln Tyr Val Asp
                85                  90                  95

Thr Leu Tyr Pro Gly Phe Glu Gly Thr Glu Met Trp Asn Pro Asn Arg
            100                 105                 110

Glu Leu Ser Glu Asp Cys Leu Tyr Leu Asn Val Trp Thr Pro Tyr Pro
        115                 120                 125

Arg Pro Thr Ser Pro Thr Pro Val Leu Val Trp Ile Tyr Gly Gly Gly
    130                 135                 140

Phe Tyr Ser Gly Ala Ser Ser Leu Asp Val Tyr Asp Gly Arg Phe Leu
145                 150                 155                 160

Val Gln Ala Glu Arg Thr Val Leu Val Ser Met Asn Tyr Arg Val Gly
                165                 170                 175

Ala Phe Gly Phe Leu Ala Leu Pro Gly Ser Arg Glu Ala Pro Gly Asn
            180                 185                 190

Val Gly Leu Leu Asp Gln Arg Leu Ala Leu Gln Trp Val Gln Glu Asn
        195                 200                 205

Val Ala Ala Phe Gly Gly Asp Pro Thr Ser Val Thr Leu Phe Gly Glu
    210                 215                 220

Ser Ala Gly Ala Ala Ser Val Gly Met His Leu Leu Ser Pro Pro Ser
225                 230                 235                 240

Arg Gly Leu Phe His Arg Ala Val Leu Gln Ser Gly Ala Pro Asn Gly
                245                 250                 255

Pro Trp Ala Thr Val Gly Met Gly Glu Ala Arg Arg Arg Ala Thr Gln
            260                 265                 270

Leu Ala His Leu Val Gly Cys Pro Gly Gly Thr Gly Gly Asn Asp
        275                 280                 285

Thr Glu Leu Val Ala Cys Leu Arg Thr Arg Pro Ala Gln Val Leu Val
    290                 295                 300

Asn His Glu Trp His Val Leu Pro Gln Glu Ser Val Phe Arg Phe Ser
305                 310                 315                 320

Phe Val Pro Val Val Asp Gly Asp Phe Leu Ser Asp Thr Pro Glu Ala
                325                 330                 335

Leu Ile Asn Ala Gly Asp Phe His Gly Leu Gln Val Leu Val Gly Val
                340                 345                 350

Val Lys Asp Glu Gly Ser Tyr Phe Leu Val Tyr Gly Ala Pro Gly Phe
            355                 360                 365

Ser Lys Asp Asn Glu Ser Leu Ile Ser Arg Ala Glu Phe Leu Ala Gly
        370                 375                 380

Val Arg Val Gly Val Pro Gln Val Ser Asp Leu Ala Ala Glu Ala Val
385                 390                 395                 400

Val Leu His Tyr Thr Asp Trp Leu His Pro Glu Asp Pro Ala Arg Leu
                405                 410                 415

Arg Glu Ala Leu Ser Asp Val Val Gly Asp His Asn Val Val Cys Pro
                420                 425                 430

Val Ala Gln Leu Ala Gly Arg Leu Ala Ala Gln Gly Ala Arg Val Tyr
            435                 440                 445

Ala Tyr Val Phe Glu His Arg Ala Ser Thr Leu Ser Trp Pro Leu Trp
        450                 455                 460

Met Gly Val Pro His Gly Tyr Glu Ile Glu Phe Ile Phe Gly Ile Pro
465                 470                 475                 480

Leu Asp Pro Ser Arg Asn Tyr Thr Ala Glu Glu Lys Ile Phe Ala Gln
                485                 490                 495

Arg Leu Met Arg Tyr Trp Ala Asn Phe Ala Arg Thr Gly Asp Pro Asn
            500                 505                 510

Glu Pro Arg Asp Pro Lys Ala Pro Gln Trp Pro Pro Tyr Thr Ala Gly
        515                 520                 525

Ala Gln Gln Tyr Val Ser Leu Asp Leu Arg Pro Leu Glu Val Arg Arg
    530                 535                 540

Gly Leu Arg Ala Gln Ala Cys Ala Phe Trp Asn Arg Phe Leu Pro Lys
545                 550                 555                 560

Leu Leu Ser Ala Thr Ala Ser Glu Ala Pro
                565                 570

<210> SEQ ID NO 14
<211> LENGTH: 50
<212> TYPE: PRT
<213> ORGANISM: Homo sapiens

<400> SEQUENCE: 14

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro

```
                    20                  25                  30
Lys Asp Thr Leu Met Ile Ser Arg Thr Pro Glu Val Thr Cys Val Val
            35                  40                  45

Val Asp
    50

<210> SEQ ID NO 15
<211> LENGTH: 232
<212> TYPE: PRT
<213> ORGANISM: Homo sapiens

<400> SEQUENCE: 15

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 16
<211> LENGTH: 802
<212> TYPE: PRT
<213> ORGANISM: Artificial Sequence
<220> FEATURE:
<223> OTHER INFORMATION: Amino acid sequence of the Kappa-leader
      sequence fused to Modified AChE, the spacer and the Fc domain (K-
      Modified AChE-spacer-Fc or K-NL1 fusion protein)
<220> FEATURE:
<221> NAME/KEY: misc_feature
<223> OTHER INFORMATION: Synthetic

<400> SEQUENCE: 16

Met Asp Met Arg Ala His Val Leu Leu Gly Leu Leu Leu Leu Trp
1               5                   10                  15
```

-continued

```
Leu Pro Gly Ala Lys Cys Glu Gly Arg Glu Asp Ala Glu Leu Leu Val
             20                  25                  30

Thr Val Arg Gly Gly Arg Leu Arg Gly Ile Arg Leu Lys Thr Pro Gly
         35                  40                  45

Gly Pro Val Ser Ala Phe Leu Gly Ile Pro Phe Ala Glu Pro Pro Met
 50                  55                  60

Gly Pro Arg Arg Phe Leu Pro Pro Glu Pro Lys Gln Pro Trp Ser Gly
 65                  70                  75                  80

Val Val Asp Ala Thr Thr Phe Gln Ser Val Cys Tyr Gln Tyr Val Asp
                 85                  90                  95

Thr Leu Tyr Pro Gly Phe Glu Gly Thr Glu Met Trp Asn Pro Asn Arg
            100                 105                 110

Glu Leu Ser Glu Asp Cys Leu Tyr Leu Asn Val Trp Thr Pro Tyr Pro
        115                 120                 125

Arg Pro Thr Ser Pro Thr Pro Val Leu Val Trp Ile Tyr Gly Gly Gly
        130                 135                 140

Phe Tyr Ser Gly Ala Ser Ser Leu Asp Val Tyr Asp Gly Arg Phe Leu
145                 150                 155                 160

Val Gln Ala Glu Arg Thr Val Leu Val Ser Met Asn Tyr Arg Val Gly
                165                 170                 175

Ala Phe Gly Phe Leu Ala Leu Pro Gly Ser Arg Glu Ala Pro Gly Asn
            180                 185                 190

Val Gly Leu Leu Asp Gln Arg Leu Ala Leu Gln Trp Val Gln Glu Asn
        195                 200                 205

Val Ala Ala Phe Gly Gly Asp Pro Thr Ser Val Thr Leu Phe Gly Glu
        210                 215                 220

Ser Ala Gly Ala Ala Ser Val Gly Met His Leu Leu Ser Pro Pro Ser
225                 230                 235                 240

Arg Gly Leu Phe His Arg Ala Val Leu Gln Ser Gly Ala Pro Asn Gly
                245                 250                 255

Pro Trp Ala Thr Val Gly Met Gly Glu Ala Arg Arg Arg Ala Thr Gln
            260                 265                 270

Leu Ala His Leu Val Gly Cys Pro Pro Gly Gly Thr Gly Gly Asn Asp
        275                 280                 285

Thr Glu Leu Val Ala Cys Leu Arg Thr Arg Pro Ala Gln Val Leu Val
        290                 295                 300

Asn His Glu Trp His Val Leu Pro Gln Glu Ser Val Phe Arg Phe Ser
305                 310                 315                 320

Phe Val Pro Val Val Asp Gly Asp Phe Leu Ser Asp Thr Pro Glu Ala
                325                 330                 335

Leu Ile Asn Ala Gly Asp Phe His Gly Leu Gln Val Leu Val Gly Val
            340                 345                 350

Val Lys Asp Glu Gly Ser Tyr Phe Leu Val Tyr Gly Ala Pro Gly Phe
        355                 360                 365

Ser Lys Asp Asn Glu Ser Leu Ile Ser Arg Ala Glu Phe Leu Ala Gly
        370                 375                 380

Val Arg Val Gly Val Pro Gln Val Ser Asp Leu Ala Ala Glu Ala Val
385                 390                 395                 400

Val Leu His Tyr Thr Asp Trp Leu His Pro Glu Asp Pro Ala Arg Leu
                405                 410                 415

Arg Glu Ala Leu Ser Asp Val Val Gly Asp His Asn Val Val Cys Pro
            420                 425                 430

Val Ala Gln Leu Ala Gly Arg Leu Ala Ala Gln Gly Ala Arg Val Tyr
```

```
                      435                 440                 445
Ala Tyr Val Phe Glu His Arg Ala Ser Thr Leu Ser Trp Pro Leu Trp
450                 455                 460

Met Gly Val Pro His Gly Tyr Glu Ile Glu Phe Ile Phe Gly Ile Pro
465                 470                 475                 480

Leu Asp Pro Ser Arg Asn Tyr Thr Ala Glu Glu Lys Ile Phe Ala Gln
                485                 490                 495

Arg Leu Met Arg Tyr Trp Ala Asn Phe Ala Arg Thr Gly Asp Pro Asn
                500                 505                 510

Glu Pro Arg Asp Pro Lys Ala Pro Gln Trp Pro Pro Tyr Thr Ala Gly
            515                 520                 525

Ala Gln Gln Tyr Val Ser Leu Asp Leu Arg Pro Leu Glu Val Arg Arg
530                 535                 540

Gly Leu Arg Ala Gln Ala Cys Ala Phe Trp Asn Arg Phe Leu Pro Lys
545                 550                 555                 560

Leu Leu Ser Ala Thr Ala Ser Glu Ala Pro Glu Pro Lys Ser Ser Asp
                565                 570                 575

Lys Thr His Thr Cys Pro Pro Cys Pro Ala Pro Glu Leu Leu Gly Gly
                580                 585                 590

Pro Ser Val Phe Leu Phe Pro Pro Lys Pro Lys Asp Thr Leu Met Ile
            595                 600                 605

Ser Arg Thr Pro Glu Val Thr Cys Val Val Val Asp Val Ser His Glu
610                 615                 620

Asp Pro Glu Val Lys Phe Asn Trp Tyr Val Asp Gly Val Glu Val His
625                 630                 635                 640

Asn Ala Lys Thr Lys Pro Arg Glu Glu Gln Tyr Asn Ser Thr Tyr Arg
                645                 650                 655

Val Val Ser Val Leu Thr Val Leu His Gln Asp Trp Leu Asn Gly Lys
                660                 665                 670

Glu Tyr Lys Cys Lys Val Ser Asn Lys Ala Leu Pro Ala Pro Ile Glu
            675                 680                 685

Lys Thr Ile Ser Lys Ala Lys Gly Gln Pro Arg Glu Pro Gln Val Tyr
690                 695                 700

Thr Leu Pro Pro Ser Arg Glu Glu Met Thr Lys Asn Gln Val Ser Leu
705                 710                 715                 720

Thr Cys Leu Val Lys Gly Phe Tyr Pro Ser Asp Ile Ala Val Glu Trp
                725                 730                 735

Glu Ser Asn Gly Gln Pro Glu Asn Asn Tyr Lys Thr Thr Pro Pro Val
                740                 745                 750

Leu Asp Ser Asp Gly Ser Phe Phe Leu Tyr Ser Lys Leu Thr Val Asp
            755                 760                 765

Lys Ser Arg Trp Gln Gln Gly Asn Val Phe Ser Cys Ser Val Met His
770                 775                 780

Glu Ala Leu His Asn His Tyr Thr Gln Lys Ser Leu Ser Leu Ser Pro
785                 790                 795                 800

Gly Lys

<210> SEQ ID NO 17
<211> LENGTH: 780
<212> TYPE: PRT
<213> ORGANISM: Artificial Sequence
<220> FEATURE:
<223> OTHER INFORMATION: Amino acid sequence of the NL1 fusion protein
<220> FEATURE:
<221> NAME/KEY: misc_feature
```

<223> OTHER INFORMATION: Synthetic

<400> SEQUENCE: 17

```
Glu Gly Arg Glu Asp Ala Glu Leu Leu Val Thr Val Arg Gly Gly Arg
1               5                   10                  15
Leu Arg Gly Ile Arg Leu Lys Thr Pro Gly Gly Pro Val Ser Ala Phe
            20                  25                  30
Leu Gly Ile Pro Phe Ala Glu Pro Pro Met Gly Pro Arg Arg Phe Leu
        35                  40                  45
Pro Pro Glu Pro Lys Gln Pro Trp Ser Gly Val Val Asp Ala Thr Thr
    50                  55                  60
Phe Gln Ser Val Cys Tyr Gln Tyr Val Asp Thr Leu Tyr Pro Gly Phe
65                  70                  75                  80
Glu Gly Thr Glu Met Trp Asn Pro Asn Arg Glu Leu Ser Glu Asp Cys
                85                  90                  95
Leu Tyr Leu Asn Val Trp Thr Pro Tyr Pro Arg Pro Thr Ser Pro Thr
            100                 105                 110
Pro Val Leu Val Trp Ile Tyr Gly Gly Phe Tyr Ser Gly Ala Ser
        115                 120                 125
Ser Leu Asp Val Tyr Asp Gly Arg Phe Leu Val Gln Ala Glu Arg Thr
    130                 135                 140
Val Leu Val Ser Met Asn Tyr Arg Val Gly Ala Phe Gly Phe Leu Ala
145                 150                 155                 160
Leu Pro Gly Ser Arg Glu Ala Pro Gly Asn Val Gly Leu Leu Asp Gln
                165                 170                 175
Arg Leu Ala Leu Gln Trp Val Gln Glu Asn Val Ala Ala Phe Gly Gly
            180                 185                 190
Asp Pro Thr Ser Val Thr Leu Phe Gly Glu Ser Ala Gly Ala Ala Ser
        195                 200                 205
Val Gly Met His Leu Leu Ser Pro Pro Ser Arg Gly Leu Phe His Arg
    210                 215                 220
Ala Val Leu Gln Ser Gly Ala Pro Asn Gly Pro Trp Ala Thr Val Gly
225                 230                 235                 240
Met Gly Glu Ala Arg Arg Arg Ala Thr Gln Leu Ala His Leu Val Gly
                245                 250                 255
Cys Pro Pro Gly Gly Thr Gly Gly Asn Asp Thr Glu Leu Val Ala Cys
            260                 265                 270
Leu Arg Thr Arg Pro Ala Gln Val Leu Val Asn His Glu Trp His Val
        275                 280                 285
Leu Pro Gln Glu Ser Val Phe Arg Phe Ser Phe Val Pro Val Val Asp
    290                 295                 300
Gly Asp Phe Leu Ser Asp Thr Pro Glu Ala Leu Ile Asn Ala Gly Asp
305                 310                 315                 320
Phe His Gly Leu Gln Val Leu Val Gly Val Val Lys Asp Glu Gly Ser
                325                 330                 335
Tyr Phe Leu Val Tyr Gly Ala Pro Gly Phe Ser Lys Asp Asn Glu Ser
            340                 345                 350
Leu Ile Ser Arg Ala Glu Phe Leu Ala Gly Val Arg Val Gly Val Pro
        355                 360                 365
Gln Val Ser Asp Leu Ala Ala Glu Ala Val Val Leu His Tyr Thr Asp
    370                 375                 380
Trp Leu His Pro Glu Asp Pro Ala Arg Leu Arg Glu Ala Leu Ser Asp
385                 390                 395                 400
```

Val Val Gly Asp His Asn Val Val Cys Pro Val Ala Gln Leu Ala Gly
        405                 410                 415

Arg Leu Ala Ala Gln Gly Ala Arg Val Tyr Ala Tyr Val Phe Glu His
        420                 425                 430

Arg Ala Ser Thr Leu Ser Trp Pro Leu Trp Met Gly Val Pro His Gly
        435                 440                 445

Tyr Glu Ile Glu Phe Ile Phe Gly Ile Pro Leu Asp Pro Ser Arg Asn
        450                 455                 460

Tyr Thr Ala Glu Glu Lys Ile Phe Ala Gln Arg Leu Met Arg Tyr Trp
465                 470                 475                 480

Ala Asn Phe Ala Arg Thr Gly Asp Pro Asn Glu Pro Arg Asp Pro Lys
            485                 490                 495

Ala Pro Gln Trp Pro Pro Tyr Thr Ala Gly Ala Gln Gln Tyr Val Ser
                500                 505                 510

Leu Asp Leu Arg Pro Leu Glu Val Arg Arg Gly Leu Arg Ala Gln Ala
            515                 520                 525

Cys Ala Phe Trp Asn Arg Phe Leu Pro Lys Leu Leu Ser Ala Thr Ala
530                 535                 540

Ser Glu Ala Pro Glu Pro Lys Ser Ser Asp Lys Thr His Thr Cys Pro
545                 550                 555                 560

Pro Cys Pro Ala Pro Glu Leu Leu Gly Gly Pro Ser Val Phe Leu Phe
                565                 570                 575

Pro Pro Lys Pro Lys Asp Thr Leu Met Ile Ser Arg Thr Pro Glu Val
            580                 585                 590

Thr Cys Val Val Val Asp Val Ser His Glu Asp Pro Glu Val Lys Phe
        595                 600                 605

Asn Trp Tyr Val Asp Gly Val Glu Val His Asn Ala Lys Thr Lys Pro
610                 615                 620

Arg Glu Glu Gln Tyr Asn Ser Thr Tyr Arg Val Val Ser Val Leu Thr
625                 630                 635                 640

Val Leu His Gln Asp Trp Leu Asn Gly Lys Glu Tyr Lys Cys Lys Val
                645                 650                 655

Ser Asn Lys Ala Leu Pro Ala Pro Ile Glu Lys Thr Ile Ser Lys Ala
            660                 665                 670

Lys Gly Gln Pro Arg Glu Pro Gln Val Tyr Thr Leu Pro Pro Ser Arg
        675                 680                 685

Glu Glu Met Thr Lys Asn Gln Val Ser Leu Thr Cys Leu Val Lys Gly
690                 695                 700

Phe Tyr Pro Ser Asp Ile Ala Val Glu Trp Glu Ser Asn Gly Gln Pro
705                 710                 715                 720

Glu Asn Asn Tyr Lys Thr Thr Pro Pro Val Leu Asp Ser Asp Gly Ser
                725                 730                 735

Phe Phe Leu Tyr Ser Lys Leu Thr Val Asp Lys Ser Arg Trp Gln Gln
            740                 745                 750

Gly Asn Val Phe Ser Cys Ser Val Met His Glu Ala Leu His Asn His
        755                 760                 765

Tyr Thr Gln Lys Ser Leu Ser Leu Ser Pro Gly Lys
770                 775                 780

<210> SEQ ID NO 18
<211> LENGTH: 3745
<212> TYPE: DNA
<213> ORGANISM: Artificial Sequence
<220> FEATURE:
<223> OTHER INFORMATION: Nucleic acid sequence encoding the K-NL1 fusion

```
        protein
<220> FEATURE:
<221> NAME/KEY: misc_feature
<223> OTHER INFORMATION: Synthetic

<400> SEQUENCE: 18
atggacatga gggcccatgt gcaccttctg gggctcctgc tgctctggct gcccggggcc       60
aaatgtgagg gccgggagga tgcagagctg ctggtgacgg tgcgtggggg ccggctgcgg      120
ggcattcgcc tgaagacccc cggggggccct gtctctgctt tcctgggcat ccccctttgcg    180 gagccaccca tgggaccccg tcgctttctg ccaccggagc ccaagcagcc ttggtcaggg      240
gtggtagacg ctacaacctt ccagagtgtc tgctaccaat atgtggacac cctataccca      300
ggttttgagg gcaccgagat gtggaacccc aaccgtgagc tgagcgagga ctgcctgtac      360
ctcaacgtgt ggacaccata ccccggcct acatccccca ccctgtcct cgtctggatc       420 tatgggggtg gcttctacag tggggcctcc tccttggacg tgtacgatgg ccgcttcttg      480
gtacaggccg agaggactgt gctggtgtcc atgaactacc gggtgggagc ctttggcttc      540
ctggccctgc cggggagccg agaggcccccg ggcaatgtgg gtctcctgga tcagaggctg     600
gccctgcagt gggtgcagga aacgtggca gccttcgggg gtgacccgac atcagtgacg      660
ctgtttgggg agagcgcggg agccgcctcg gtgggcatgc acctgctgtc cccgcccagc     720 cggggccctgt tccacagggc cgtgctgcag agcggtgccc ccaatggacc ctgggccacg    780
gtgggcatgg gagaggcccg tcgcagggcc acgcagctgg cccaccttgt gggctgtcct     840
ccaggcggca ctggtgggaa tgacacagag ctggtagcct gccttcggac acgaccagcg    900
caggtcctgg tgaaccacga atggcacgtg ctgcctcaag aaagcgtctt ccggttctcc     960
ttcgtgcctg tggtagatgg agacttcctc agtgacaccc cagaggccct catcaacgcg    1020
ggagacttcc acggcctgca ggtgctggtg ggtgtggtga aggatgaggg ctcgtatttt    1080
ctggtttacg gggccccagg cttcagcaaa gacaacgagt ctctcatcag ccgggccgag    1140
ttcctggccg gggtgcgggt cggggttccc caggtaagtg acctggcagc cgaggctgtg    1200
gtcctgcatt acacagactg gctgcatccc gaggacccgg cacgcctgag ggaggccctg    1260
agcgatgtgg tgggcgacca caatgtcgtg tgccccgtgg cccagctggc tgggcgactg    1320
gctgcccagg gtgcccatgg acatgagggc ccatgtgcac cttctgggc tcctgctgct    1380 ctggctgccc ggggccaaat gtgagggccg ggaggatgca gagctgctgg tgacggtgcg    1440 tggggggccgg ctgcggggca ttcgcctgaa gaccccgg gccctgtct ctgctttcct     1500 gggcatcccc tttgcggagc cacccatggg accccgtcgc tttctgccac cggagcccaa    1560
gcagccttgg tcaggggtgg tagacgctac aaccttccag agtgtctgct accaatatgt    1620
ggacacccta tacccaggtt ttgagggcac cgagatgtgg aacccaacc gtgagctgag     1680 cgaggactgc ctgtacctca acgtgtggac accataccccс cggcctacat cccccacccc    1740
tgtcctcgtc tggatctatg ggggtggctt ctacagtggg gcctcctcct tggacgtgta    1800
cgatggccgc ttcttggtac aggccgagag gactgtgctg gtgtccatga actaccgggt    1860
gggagccttt ggcttcctgg ccctgccggg gagccgagag gccccgggca atgtgggtct    1920
cctggatcag aggctggccc tgcagtgggt gcaggagaac gtggcagcct tcgggggtga    1980
cccgacatca gtgacgctgt ttggggagag cgcgggagcc gcctcggtgg gcatgcacct    2040
gctgtccccg cccagccggg gcctgttcca cagggccgtg ctgcagagcg tgccccaa     2100 tggaccctgg gccacggtgg gcatgggaga ggcccgtcgc agggcacgc agctggccca    2160
```

| | |
|---|---|
| ccttgtgggc tgtcctccag gcggcactgg tgggaatgac acagagctgg tagcctgcct | 2220 |
| tcggacacga ccagcgcagg tcctggtgaa ccacgaatgg cacgtgctgc ctcaagaaag | 2280 |
| cgtcttccgg ttctccttcg tgcctgtggt agatggagac ttcctcagtg acccccaga | 2340 |
| ggccctcatc aacgcgggag acttccacgc cctgcaggtg ctggtgggtg tggtgaagga | 2400 |
| tgagggctcg tattttctgg tttacggggc cccaggcttc agcaaagaca acgagtctct | 2460 |
| catcagccgg gccgagttcc tggccggggt gcgggtcggg gttccccagg taagtgacct | 2520 |
| ggcagccgag gctgtggtcc tgcattacac agactggctg catcccgagg acccggcacg | 2580 |
| cctgagggag gccctgagcg atgtggtggg cgaccacaat gtcgtgtgcc ccgtggccca | 2640 |
| gctggctggg cgactggctg cccaggggtgc ccgggtctac gcctacgtct ttgaacaccg | 2700 |
| tgcttccacg ctctcctggc ccctgtggat ggggtgccc cacggctacg agatcgagtt | 2760 |
| catctttggg atcccctgg accctctcg aaactacacg gcagaggaga aaatcttcgc | 2820 |
| ccagcgactg atgcgatact gggccaactt tgcccgcaca ggggatccca atgagccccg | 2880 |
| agaccccaag gccccacaat ggcccccgta acgcgcgggg gctcagcagt acgttagtct | 2940 |
| ggacctgcgg ccgctggagg tgcggcgggg gctgcgcgcc caggcctgcg ccttctggaa | 3000 |
| ccgcttcctc cccaaattgc tcagcgccac cgcctcggag gctcccgagc caaatctag | 3060 |
| tgacaaaact cacacatgcc caccgtgccc agcacctgaa ctcctggggg gaccgtcagt | 3120 |
| cttcctcttc cccccaaaac ccaaggacac cctcatgatc tcccggaccc ctgaggtcac | 3180 |
| atgcgtggtg gtggacgtga gccacgaaga ccctgaggtc aagttcaact ggtacgtgga | 3240 |
| cggcgtggag gtgcataatg ccaagacaaa gccacgggag gagcagtaca acagcaccta | 3300 |
| ccgggtggtc agcgtcctca ccgtcctgca ccaggactgg ctgaatggca aggagtacaa | 3360 |
| gtgcaaggtc tccaacaaag ccctcccagc ccccatcgag aaaaccatct ccaaagccaa | 3420 |
| agggcagcca cgggaaccac aggtttacac cctgcccccca tcccgcgagg agatgaccaa | 3480 |
| gaaccaggtc agcctgacct gcctggtcaa aggcttctat cccagcgaca tcgccgtgga | 3540 |
| gtgggagagc aatgggcagc cggagaacaa ctacaagacc cccctcccg tgctggactc | 3600 |
| cgacggctcc ttcttcctct atagcaagct caccgtggac aagagcaggt ggcagcaggg | 3660 |
| gaacgtcttc tcatgctccg tgatgcacga ggctctgcac aaccactaca cccagaagag | 3720 |
| cctctcctg tctcccggta aatga | 3745 |

<210> SEQ ID NO 19
<211> LENGTH: 2436
<212> TYPE: DNA
<213> ORGANISM: Artificial Sequence
<220> FEATURE:
<223> OTHER INFORMATION: Nucleic acid sequence encoding the SP-NL1 fusion protein
<220> FEATURE:
<221> NAME/KEY: misc_feature
<223> OTHER INFORMATION: Synthetic

<400> SEQUENCE: 19

| | |
|---|---|
| atgcggccgc cacagtgcct tctgcatacc cccagccttg ccagccctct gctgctgctg | 60 |
| ctgttgtggc tcctgggagg tggtgttggg cggaaggtc gagaggacgc cgagttgctg | 120 |
| gtgactgtcc gaggggacg gctccgggga tccgcctca aaacacctgg ggccccgtc | 180 |
| tctgcgtttc tgggcatccc tttcgcagag ccacccatgg gccccggag attcctgccc | 240 |
| ccggaaccca acagccttg gtcaggggtg tcgatgcca aactttcca gagcgtgtgc | 300 |
| tatcagtacg ttgacacctt gtatcccgga tttgaaggca ctgagatgtg aacccgaat | 360 |

```
cgagagctga gtgaggactg cctgtatctg aatgtgtgga ccccgtaccc tagaccaacc      420
tcacccaccc ctgttctcgt gtggatctac gggggaggtt tttactctgg ggccagctcc      480
ctggacgtgt atgatggcag attcctggtc caggcagaac ggacagtgct cgtgagtatg      540
aattatcggg tgggcgcctt cggattcttg cactgcccg gatcccggga ggccccaggt       600
aacgtgggac tcctcgacca gcgcctggct ctgcagtggg tgcaagaaaa tgtagcagcg      660
tttggtgggg acccaaccag tgtgactctc tttggtgaaa gcgcaggggc agcttccgtg      720
ggcatgcatc tgttgtcacc accatctagg ggattgttcc accgggctgt actgcagtct      780
ggagcgccaa atgaccatg ggccacagtg gggatgggtg aagccagacg gcgcgccacc       840
cagctggcac atctggtggg ctgcccacct gggggcaccg gaggcaacga tacagaactg      900
gtggcctgcc ttaggacccg ccccgctcaa gtcctggtga atcacgagtg gcatgtgctc      960
cctcaggaaa gcgtgtttcg gttctcattc gtgcccgtgg tggatggcga ctttctcagc     1020
gacacacccg aagcgctgat taacgccgga gatttccatg gcctccaggt tcttgtgggt     1080
gtcgtaaagg acgaggggtc ctacttcctg gtttatggcg cgccaggctt ctctaaggat     1140
aatgagagct tgatctctcg cgcggagttt ttggcaggcg tgcgcgtcgg cgtgcctcag     1200
gtttcagact tggcagccga ggccgtggtc ctccattata cggactggct gcacccggag     1260
gatcctgcca gacttcgcga agctctgtca gacgtggtcg gagaccataa tgtcgtgtgc     1320
cccgtggctc agttggctgg gcgcctcgca gcccaaggcg ccagggtata tgcgtacgtt     1380
ttcgagcacc gcgccagcac actctcatgg cctctttgga tgggcgtgcc ccacgggtat     1440
gaaatcgagt tcatattcgg catccctctg gatccatcca gaaactacac cgccgaagag     1500
aagatcttcg cccagagatt gatgagatac tgggccaact ttgctcggac cggtgaccct     1560
aacgagccca gagacccgaa ggctccccag tggcctcctt ataccgcggg tgcacagcag     1620
tacgtaagcc tggacctgag accactggag gtgcgacgcg gactgcgagc acaggcctgc     1680
gccttttgga atcggttcct ccccaagctg ttgtcagcca ccgcatccga agcccccgag     1740
cccaaatcta gtgacaaaac tcacacatgc ccaccgtgcc cagcacctga actcctgggg     1800
ggaccgtcag tcttcctctt ccccccaaaa cccaaggaca cctcatgat ctcccggacc      1860 cctgaggtca catgcgtggt ggtggacgtg agccacgaag accctgaggt caagttcaac     1920
tggtacgtgg acggcgtgga ggtgcataat gccaagacaa agccacggga ggagcagtac     1980
aacagcacct accgggtggt cagcgtcctc accgtcctgc accaggactg gctgaatggc     2040
aaggagtaca agtgcaaggt ctccaacaaa gccctcccag cccccatcga gaaaaccatc     2100
tccaaagcca agggcagccc acgggaacca caggtttaca ccctgccccc atcccgcgag     2160
gagatgacca gaaccaggt cagcctgacc tgcctggtca aaggcttcta tcccagcgac      2220
atcgccgtgg agtgggagag caatgggcag cccgagaaca actacaagac caccctcccc     2280
gtgctggact ccgacggctc cttcttcctc tatagcaagc tcaccgtgga caagagcagg     2340
tggcagcagg ggaacgtctt ctcatgctcc gtgatgcacg aggctctgca caaccactac     2400
acccagaaga gcctctccct gtctcccggt aaatga                               2436
```

<210> SEQ ID NO 20
<211> LENGTH: 984
<212> TYPE: DNA
<213> ORGANISM: Homo sapiens

<400> SEQUENCE: 20

```
accaagggcc catcggtctt cccactggca ccctcctcca agagcacctc tgggggcaca      60
gctgccctgg gctgcctggt caaggactac ttccctgaac cggtgacggt gtcgtggaac     120
tcaggcgccc tgacaagcgg cgtgcacacc ttcccggctg tgctgcagtc ttcaggactc     180
tactccctca gcagcgtggt gaccgtgccc tctagcagct ggggcaccca gacctacatc     240
tgcaacgtga atcacaagcc cagcaacacc aaggtggaca gagagtgga gcccaaatct     300 agtgacaaaa ctcacacatg cccaccgtgc ccagcacctg aactcctggg gggaccgtca     360
gtcttcctct tccccccaaa acccaaggac accctcatga tctcccggac ccctgaggtc     420
acatgcgtgg tggtggacgt gagccacgaa gaccctgagg tcaagttcaa ctggtacgtg     480
gacggcgtgg aggtgcataa tgccaagaca aagccacggg aggagcagta caacagcacc     540
taccgggtgg tcagcgtcct caccgtcctg caccaggact ggctgaatgg caaggagtac     600
aagtgcaagg tctccaacaa agccctccca gcccccatcg agaaaaccat ctccaaagcc     660
aaagggcagc cacgggaacc acaggtttac accctgcccc catcccgcga ggagatgacc     720
aagaaccagg tcagcctgac ctgcctggtc aaaggcttct atcccagcga catcgccgtg     780
gagtgggaga gcaatgggca gcccgagaac aactacaaga ccacccctcc cgtgctggac     840
tccgacggct ccttcttcct ctatagcaag ctcaccgtgg acaagagcag gtggcagcag     900
gggaacgtct tctcatgctc cgtgatgcac gaggctctgc acaaccacta cacccagaag     960
agcctctccc tgtctcccgg taaa                                            984
```

<210> SEQ ID NO 21
<211> LENGTH: 614
<212> TYPE: PRT
<213> ORGANISM: Homo sapiens

<400> SEQUENCE: 21

```
Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
```

```
                195                 200                 205
Leu Ala Leu Gln Trp Val Gln Glu Asn Val Ala Ala Phe Gly Gly Asp
    210                 215                 220
Pro Thr Ser Val Thr Leu Phe Gly Glu Ser Ala Gly Ala Ala Ser Val
225                 230                 235                 240
Gly Met His Leu Leu Ser Pro Ser Arg Gly Leu Phe His Arg Ala
            245                 250                 255
Val Leu Gln Ser Gly Ala Pro Asn Gly Pro Trp Ala Thr Val Gly Met
            260                 265                 270
Gly Glu Ala Arg Arg Arg Ala Thr Gln Leu Ala His Leu Val Gly Cys
        275                 280                 285
Pro Pro Gly Gly Thr Gly Gly Asn Asp Thr Glu Leu Val Ala Cys Leu
        290                 295                 300
Arg Thr Arg Pro Ala Gln Val Leu Val Asn His Glu Trp His Val Leu
305                 310                 315                 320
Pro Gln Glu Ser Val Phe Arg Phe Ser Phe Val Pro Val Val Asp Gly
                325                 330                 335
Asp Phe Leu Ser Asp Thr Pro Glu Ala Leu Ile Asn Ala Gly Asp Phe
                340                 345                 350
His Gly Leu Gln Val Leu Val Gly Val Val Lys Asp Glu Gly Ser Tyr
            355                 360                 365
Phe Leu Val Tyr Gly Ala Pro Gly Phe Ser Lys Asp Asn Glu Ser Leu
370                 375                 380
Ile Ser Arg Ala Glu Phe Leu Ala Gly Val Arg Val Gly Val Pro Gln
385                 390                 395                 400
Val Ser Asp Leu Ala Ala Glu Ala Val Val Leu His Tyr Thr Asp Trp
                405                 410                 415
Leu His Pro Glu Asp Pro Ala Arg Leu Arg Glu Ala Leu Ser Asp Val
                420                 425                 430
Val Gly Asp His Asn Val Val Cys Pro Val Ala Gln Leu Ala Gly Arg
            435                 440                 445
Leu Ala Ala Gln Gly Ala Arg Val Tyr Ala Tyr Val Phe Glu His Arg
450                 455                 460
Ala Ser Thr Leu Ser Trp Pro Leu Trp Met Gly Val Pro His Gly Tyr
465                 470                 475                 480
Glu Ile Glu Phe Ile Phe Gly Ile Pro Leu Asp Pro Ser Arg Asn Tyr
                485                 490                 495
Thr Ala Glu Glu Lys Ile Phe Ala Gln Arg Leu Met Arg Tyr Trp Ala
                500                 505                 510
Asn Phe Ala Arg Thr Gly Asp Pro Asn Glu Pro Arg Asp Pro Lys Ala
            515                 520                 525
Pro Gln Trp Pro Pro Tyr Thr Ala Gly Ala Gln Gln Tyr Val Ser Leu
        530                 535                 540
Asp Leu Arg Pro Leu Glu Val Arg Arg Gly Leu Arg Ala Gln Ala Cys
545                 550                 555                 560
Ala Phe Trp Asn Arg Phe Leu Pro Lys Leu Leu Ser Ala Thr Asp Thr
                565                 570                 575
Leu Asp Glu Ala Glu Arg Gln Trp Lys Ala Glu Phe His Arg Trp Ser
            580                 585                 590
Ser Tyr Met Val His Trp Lys Asn Gln Phe Asp His Tyr Ser Lys Gln
            595                 600                 605
Asp Arg Cys Ser Asp Leu
        610
```

<210> SEQ ID NO 22
<211> LENGTH: 802
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 22

```
Met Asp Met Arg Ala His Val His Leu Leu Gly Leu Leu Leu Leu Trp
1               5                   10                  15

Leu Pro Gly Ala Lys Cys Glu Gly Arg Glu Asp Ala Glu Leu Leu Val
            20                  25                  30

Thr Val Arg Gly Gly Arg Leu Arg Gly Ile Arg Leu Lys Thr Pro Gly
        35                  40                  45

Gly Pro Val Ser Ala Phe Leu Gly Ile Pro Phe Ala Glu Pro Pro Met
    50                  55                  60

Gly Pro Arg Arg Phe Leu Pro Pro Glu Pro Lys Gln Pro Trp Ser Gly
65                  70                  75                  80

Val Val Asp Ala Thr Thr Phe Gln Ser Val Cys Tyr Gln Tyr Val Asp
                85                  90                  95

Thr Leu Tyr Pro Gly Phe Glu Gly Thr Glu Met Trp Asn Pro Asn Arg
            100                 105                 110

Glu Leu Ser Glu Asp Cys Leu Tyr Leu Asn Val Trp Thr Pro Tyr Pro
        115                 120                 125

Arg Pro Thr Ser Pro Thr Pro Val Leu Val Trp Ile Tyr Gly Gly Gly
    130                 135                 140

Phe Tyr Ser Gly Ala Ser Ser Leu Asp Val Tyr Asp Gly Arg Phe Leu
145                 150                 155                 160

Val Gln Ala Glu Arg Thr Val Leu Val Ser Met Asn Tyr Arg Val Gly
                165                 170                 175

Ala Phe Gly Phe Leu Ala Leu Pro Gly Ser Arg Glu Ala Pro Gly Asn
            180                 185                 190

Val Gly Leu Leu Asp Gln Arg Leu Ala Leu Gln Trp Val Gln Glu Asn
        195                 200                 205

Val Ala Ala Phe Gly Gly Asp Pro Thr Ser Val Thr Leu Phe Gly Glu
    210                 215                 220

Ser Ala Gly Ala Ala Ser Val Gly Met His Leu Leu Ser Pro Pro Ser
225                 230                 235                 240

Arg Gly Leu Phe His Arg Ala Val Leu Gln Ser Gly Ala Pro Asn Gly
                245                 250                 255

Pro Trp Ala Thr Val Gly Met Gly Glu Ala Arg Arg Arg Ala Thr Gln
            260                 265                 270

Leu Ala His Leu Val Gly Cys Pro Pro Gly Gly Thr Gly Gly Asn Asp
        275                 280                 285

Thr Glu Leu Val Ala Cys Leu Arg Thr Arg Pro Ala Gln Val Leu Val
    290                 295                 300

Asn His Glu Trp His Val Leu Pro Gln Glu Ser Val Phe Arg Phe Ser
305                 310                 315                 320

Phe Val Pro Val Val Asp Gly Asp Phe Leu Ser Asp Thr Pro Glu Ala
                325                 330                 335

Leu Ile Asn Ala Gly Asp Phe His Gly Leu Gln Val Leu Val Gly Val
            340                 345                 350
```

```
Val Lys Asp Glu Gly Ser Tyr Phe Leu Val Tyr Gly Ala Pro Gly Phe
    355                 360                 365

Ser Lys Asp Asn Glu Ser Leu Ile Ser Arg Ala Glu Phe Leu Ala Gly
    370                 375                 380

Val Arg Val Gly Val Pro Gln Val Ser Asp Leu Ala Ala Glu Ala Val
385                 390                 395                 400

Val Leu His Tyr Thr Asp Trp Leu His Pro Glu Asp Pro Ala Arg Leu
                405                 410                 415

Arg Glu Ala Leu Ser Asp Val Val Gly Asp His Asn Val Val Cys Pro
                420                 425                 430

Val Ala Gln Leu Ala Gly Arg Leu Ala Ala Gln Gly Ala Arg Val Tyr
                435                 440                 445

Ala Tyr Val Phe Glu His Arg Ala Ser Thr Leu Ser Trp Pro Leu Trp
                450                 455                 460

Met Gly Val Pro His Gly Tyr Glu Ile Glu Phe Ile Phe Gly Ile Pro
465                 470                 475                 480

Leu Asp Pro Ser Arg Asn Tyr Thr Ala Glu Glu Lys Ile Phe Ala Gln
                485                 490                 495

Arg Leu Met Arg Tyr Trp Ala Asn Phe Ala Arg Thr Gly Asp Pro Asn
                500                 505                 510

Glu Pro Arg Asp Pro Lys Ala Pro Gln Trp Pro Pro Tyr Thr Ala Gly
                515                 520                 525

Ala Gln Gln Tyr Val Ser Leu Asp Leu Arg Pro Leu Glu Val Arg Arg
                530                 535                 540

Gly Leu Arg Ala Gln Ala Cys Ala Phe Trp Asn Arg Phe Leu Pro Lys
545                 550                 555                 560

Leu Leu Ser Ala Thr Ala Ser Glu Ala Pro Glu Pro Lys Ser Ser Asp
                565                 570                 575

Lys Thr His Thr Cys Pro Pro Cys Pro Ala Pro Glu Leu Leu Gly Gly
                580                 585                 590

Pro Ser Val Phe Leu Phe Pro Pro Lys Pro Lys Asp Thr Leu Met Ile
                595                 600                 605

Ser Arg Thr Pro Glu Val Thr Cys Val Val Val Asp Val Ser His Glu
    610                 615                 620

Asp Pro Glu Val Lys Phe Asn Trp Tyr Val Asp Gly Val Glu Val His
625                 630                 635                 640

Asn Ala Lys Thr Lys Pro Arg Glu Glu Gln Tyr Asn Ser Thr Tyr Arg
                645                 650                 655

Val Val Ser Val Leu Thr Val Leu His Gln Asp Trp Leu Asn Gly Lys
                660                 665                 670

Glu Tyr Lys Cys Lys Val Ser Asn Lys Ala Leu Pro Ala Pro Ile Glu
                675                 680                 685

Lys Thr Ile Ser Lys Ala Lys Gly Gln Pro Arg Glu Pro Gln Val Tyr
    690                 695                 700

Thr Leu Pro Pro Ser Arg Glu Glu Met Thr Lys Asn Gln Val Ser Leu
705                 710                 715                 720

Thr Cys Leu Val Lys Gly Phe Tyr Pro Ser Asp Ile Ala Val Glu Trp
                725                 730                 735

Glu Ser Asn Gly Gln Pro Glu Asn Asn Tyr Lys Thr Thr Pro Pro Val
                740                 745                 750

Leu Asp Ser Asp Gly Ser Phe Phe Leu Tyr Ser Lys Leu Thr Val Asp
                755                 760                 765
```

-continued

Lys Ser Arg Trp Gln Gln Gly Asn Val Phe Ser Cys Ser Val Met His
770                 775                 780

Glu Ala Leu His Asn His Tyr Thr Gln Lys Ser Leu Ser Leu Ser Pro
785                 790                 795                 800

Gly Lys

<210> SEQ ID NO 23
<211> LENGTH: 780
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 23

Glu Gly Arg Glu Asp Ala Glu Leu Leu Val Thr Val Arg Gly Gly Arg
1               5                   10                  15

Leu Arg Gly Ile Arg Leu Lys Thr Pro Gly Gly Pro Val Ser Ala Phe
            20                  25                  30

Leu Gly Ile Pro Phe Ala Glu Pro Pro Met Gly Pro Arg Arg Phe Leu
        35                  40                  45

Pro Pro Glu Pro Lys Gln Pro Trp Ser Gly Val Val Asp Ala Thr Thr
50                  55                  60

Phe Gln Ser Val Cys Tyr Gln Tyr Val Asp Thr Leu Tyr Pro Gly Phe
65                  70                  75                  80

Glu Gly Thr Glu Met Trp Asn Pro Asn Arg Glu Leu Ser Glu Asp Cys
                85                  90                  95

Leu Tyr Leu Asn Val Trp Thr Pro Tyr Pro Arg Pro Thr Ser Pro Thr
            100                 105                 110

Pro Val Leu Val Trp Ile Tyr Gly Gly Gly Phe Tyr Ser Gly Ala Ser
        115                 120                 125

Ser Leu Asp Val Tyr Asp Gly Arg Phe Leu Val Gln Ala Glu Arg Thr
130                 135                 140

Val Leu Val Ser Met Asn Tyr Arg Val Gly Ala Phe Gly Phe Leu Ala
145                 150                 155                 160

Leu Pro Gly Ser Arg Glu Ala Pro Gly Asn Val Gly Leu Leu Asp Gln
                165                 170                 175

Arg Leu Ala Leu Gln Trp Val Gln Glu Asn Val Ala Ala Phe Gly Gly
            180                 185                 190

Asp Pro Thr Ser Val Thr Leu Phe Gly Glu Ser Ala Gly Ala Ala Ser
        195                 200                 205

Val Gly Met His Leu Leu Ser Pro Ser Arg Gly Leu Phe His Arg
210                 215                 220

Ala Val Leu Gln Ser Gly Ala Pro Asn Gly Pro Trp Ala Thr Val Gly
225                 230                 235                 240

Met Gly Glu Ala Arg Arg Arg Ala Thr Gln Leu Ala His Leu Val Gly
                245                 250                 255

Cys Pro Pro Gly Gly Thr Gly Gly Asn Asp Thr Glu Leu Val Ala Cys
            260                 265                 270

Leu Arg Thr Arg Pro Ala Gln Val Leu Val Asn His Glu Trp His Val
        275                 280                 285

Leu Pro Gln Glu Ser Val Phe Arg Phe Ser Phe Val Pro Val Val Asp
290                 295                 300

Gly Asp Phe Leu Ser Asp Thr Pro Glu Ala Leu Ile Asn Ala Gly Asp

```
305                 310                 315                 320
    Phe His Gly Leu Gln Val Leu Gly Val Val Lys Asp Glu Gly Ser
                    325                 330                 335

Tyr Phe Leu Val Tyr Gly Ala Pro Gly Phe Ser Lys Asp Asn Glu Ser
                    340                 345                 350

Leu Ile Ser Arg Ala Glu Phe Leu Ala Gly Val Arg Val Gly Val Pro
                    355                 360                 365

Gln Val Ser Asp Leu Ala Ala Glu Ala Val Val Leu His Tyr Thr Asp
                    370                 375                 380

Trp Leu His Pro Glu Asp Pro Ala Arg Leu Arg Glu Ala Leu Ser Asp
    385                 390                 395                 400

Val Val Gly Asp His Asn Val Val Cys Pro Val Ala Gln Leu Ala Gly
                        405                 410                 415

Arg Leu Ala Ala Gln Gly Ala Arg Val Tyr Ala Tyr Val Phe Glu His
                    420                 425                 430

Arg Ala Ser Thr Leu Ser Trp Pro Leu Trp Met Gly Val Pro His Gly
                    435                 440                 445

Tyr Glu Ile Glu Phe Ile Phe Gly Ile Pro Leu Asp Pro Ser Arg Asn
                    450                 455                 460

Tyr Thr Ala Glu Glu Lys Ile Phe Ala Gln Arg Leu Met Arg Tyr Trp
    465                 470                 475                 480

Ala Asn Phe Ala Arg Thr Gly Asp Pro Asn Glu Pro Arg Asp Pro Lys
                    485                 490                 495

Ala Pro Gln Trp Pro Pro Tyr Thr Ala Gly Ala Gln Gln Tyr Val Ser
                    500                 505                 510

Leu Asp Leu Arg Pro Leu Glu Val Arg Arg Gly Leu Arg Ala Gln Ala
                    515                 520                 525

Cys Ala Phe Trp Asn Arg Phe Leu Pro Lys Leu Leu Ser Ala Thr Ala
                    530                 535                 540

Ser Glu Ala Pro Glu Pro Lys Ser Ser Asp Lys Thr His Thr Cys Pro
    545                 550                 555                 560

Pro Cys Pro Ala Pro Glu Leu Leu Gly Gly Pro Ser Val Phe Leu Phe
                        565                 570                 575

Pro Pro Lys Pro Lys Asp Thr Leu Met Ile Ser Arg Thr Pro Glu Val
                    580                 585                 590

Thr Cys Val Val Val Asp Val Ser His Glu Asp Pro Glu Val Lys Phe
                    595                 600                 605

Asn Trp Tyr Val Asp Gly Val Glu Val His Asn Ala Lys Thr Lys Pro
                    610                 615                 620

Arg Glu Glu Gln Tyr Asn Ser Thr Tyr Arg Val Val Ser Val Leu Thr
    625                 630                 635                 640

Val Leu His Gln Asp Trp Leu Asn Gly Lys Glu Tyr Lys Cys Lys Val
                        645                 650                 655

Ser Asn Lys Ala Leu Pro Ala Pro Ile Glu Lys Thr Ile Ser Lys Ala
                    660                 665                 670

Lys Gly Gln Pro Arg Glu Pro Gln Val Tyr Thr Leu Pro Pro Ser Arg
                    675                 680                 685

Glu Glu Met Thr Lys Asn Gln Val Ser Leu Thr Cys Leu Val Lys Gly
                    690                 695                 700

Phe Tyr Pro Ser Asp Ile Ala Val Glu Trp Glu Ser Asn Gly Gln Pro
    705                 710                 715                 720

Glu Asn Asn Tyr Lys Thr Thr Pro Pro Val Leu Asp Ser Asp Gly Ser
                        725                 730                 735
```

```
Phe Phe Leu Tyr Ser Lys Leu Thr Val Asp Lys Ser Arg Trp Gln Gln
            740                 745                 750

Gly Asn Val Phe Ser Cys Ser Val Met His Glu Ala Leu His Asn His
            755                 760                 765

Tyr Thr Gln Lys Ser Leu Ser Leu Ser Pro Gly Lys
    770                 775                 780

<210> SEQ ID NO 24
<211> LENGTH: 2409
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 24
```

| | | | | |
|---|---|---|---|---|
| atggacatga gggcccatgt gcaccttctg gggctcctgc tgctctggct gcccggggcc | 60 |
| aaatgtgagg gccgggagga tgcagagctg ctggtgacgg tgcgtggggg ccggctgcgg | 120 |
| ggcattcgcc tgaagacccc cggggggccct gtctctgctt tcctgggcat ccccttttgcg | 180 |
| gagccaccca tgggacccccg tcgctttctg ccaccggagc ccaagcagcc ttggtcaggg | 240 |
| gtggtagacg ctacaacctt ccagagtgtc tgctaccaat atgtggacac cctatacccca | 300 |
| ggtttttgagg gcaccgagat gtggaacccc aaccgtgagc tgagcgagga ctgcctgtac | 360 |
| ctcaacgtgt ggaccaccata ccccggcct acatccccca cccctgtcct cgtctggatc | 420 |
| tatgggggtg gcttctacag tggggcctcc tccttggacg tgtacgatgg ccgcttcttg | 480 |
| gtacaggccg agaggactgt gctggtgtcc atgaactacc gggtgggagc ctttggcttc | 540 |
| ctggccctgc cggggagccg agaggccccg ggcaatgtgg gtctcctgga tcagaggctg | 600 |
| gccctgcagt gggtgcagga aacgtggca gccttcgggg gtgacccgac atcagtgacg | 660 |
| ctgtttgggg agagcgcggg agccgcctcg gtgggcatgc acctgctgtc cccgcccagc | 720 |
| cggggcctgt tccacagggc cgtgctgcag agcggtgccc ccaatggacc ctgggccacg | 780 |
| gtgggcatgg agaggcccg tcgcagggcc acgcagctgg cccaccttgt gggctgtcct | 840 |
| ccaggcggca ctggtgggaa tgacacagag ctggtagcct gccttcggac acgaccagcg | 900 |
| caggtcctgg tgaaccacga atggcacgtg ctgcctcaag aaagcgtctt ccggttctcc | 960 |
| ttcgtgcctg tggtagatgg agacttcctc agtgacaccc cagaggccct catcaacgcg | 1020 |
| ggagacttcc acggcctgca ggtgctggtg ggtgtggtga aggatgaggg ctcgtatttt | 1080 |
| ctggtttacg gggccccagg cttcagcaaa gacaacgagt ctctcatcag ccgggccgag | 1140 |
| ttcctggccg gggtgcgggt cggggttccc caggtaagtg acctggcagc cgaggctgtg | 1200 |
| gtcctgcatt acacagactg gctgcatccc gaggacccgg cacgcctgag ggaggccctg | 1260 |
| agcgatgtgg tgggcgacca caatgtcgtg tgccccgtgg cccagctggc tgggcgactg | 1320 |
| gctgcccagg gtgcccgggt ctacgcctac gtctttgaac accgtgcttc cacgctctcc | 1380 |
| tggcccctgt ggatgggggt gccccacggc tacgagatcg agttcatctt tgggatcccc | 1440 |
| ctggaccccct ctcgaaacta cacggcagag gagaaaatct tcgcccagcg actgatgcga | 1500 |
| tactgggcca actttgcccg cacaggggat cccaatgagc ccgagaccc caaggcccca | 1560 |
| caatggcccc cgtacacggc gggggctcag cagtacgtta gtctggacct gcggccgctg | 1620 |
| gaggtgcggc gggggctgcg cgcccaggcc tgcgccttct ggaaccgctt cctccccaaa | 1680 |

```
ttgctcagcg ccaccgcctc ggaggctccc gagcccaaat ctagtgacaa aactcacaca    1740
tgcccaccgt gcccagcacc tgaactcctg gggggaccgt cagtcttcct cttccccca     1800 aaacccaagg acaccctcat gatctcccgg acccctgagg tcacatgcgt ggtggtggac    1860
gtgagccacg aagaccctga ggtcaagttc aactggtacg tggacggcgt ggaggtgcat    1920
aatgccaaga caaagccacg ggaggagcag tacaacagca cctaccgggt ggtcagcgtc    1980
ctcaccgtcc tgcaccagga ctggctgaat ggcaaggagt acaagtgcaa ggtctccaac    2040
aaagccctcc cagccccat cgagaaaacc atctccaaag ccaagggca gccacgggaa      2100 ccacaggttt acaccctgcc cccatcccgc gaggagatga ccaagaacca ggtcagcctg    2160
acctgcctgg tcaaaggctt ctatcccagc gacatcgccg tggagtggga gagcaatggg    2220
cagcccgaga caactacaa gaccacccct cccgtgctgg actccgacgg ctccttcttc     2280
ctctatagca agctcaccgt ggacaagagc aggtggcagc aggggaacgt cttctcatgc    2340
tccgtgatgc acgaggctct gcacaaccac tacacccaga gagcctctc cctgtctccc     2400 ggtaaatga                                                             2409
```

<210> SEQ ID NO 25
<211> LENGTH: 2436
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Synthetic

<400> SEQUENCE: 25

```
atgcggccgc cacagtgcct tctgcatacc cccagccttg ccagccctct gctgctgctg      60
ctgttgtggc tcctgggagg tggtgttggg gcggaaggtc gagaggacgc cgagttgctg    120
gtgactgtcc gagggggacg gctccgggga atccgcctca aaacacctgg ggccccgtc     180 tctgcgtttc tgggcatccc tttcgcagag ccacccatgg gccccggag attcctgccc    240 ccggaaccca aacagccttg gtcagggggtg gtcgatgcca caactttcca gagcgtgtgc   300
tatcagtacg ttgacacctt gtatcccgga tttgaaggca ctgagatgtg gaacccgaat    360
cgagagctga gtgaggactg cctgtatctg aatgtgtgga ccccgtaccc tagaccaacc    420
tcacccaccg ctgttctcgt gtggatctac gggggagggt tttactctgg ggccagctcc    480
ctggacgtgt atgatggcag attcctggtc caggcagaac ggacagtgct cgtgagtatg    540
aattatcggg tgggcgcctt cggattcttg cactgcccg gatcccggga ggccccaggt    600
aacgtgggac tcctcgacca gcgcctggct ctgcagtggg tgcaagaaaa tgtagcagcg    660
tttggtgggg acccaaccag tgtgactctc tttggtgaaa gcgcaggggc agcttccgtg    720
ggcatgcatc tgttgtcacc accatctagg ggattgttcc accgggctgt actgcagtct    780
ggagcgccaa atgaccatg gccacagtg gggatgggtg aagccagacg gcgcgccacc     840
cagctggcac atctggtggg ctgcccacct gggggcaccg gaggcaacga tacagaactg    900
gtggcctgcc ttaggaccg ccccgctcaa gtcctggtga tcacgagtg gcatgtgctc     960 cctcaggaaa gcgtgtttcg gttctcattc gtgcccgtgg tggatggcga ctttctcagc   1020
gacacacccg aagcgctgat aacgccgga gatttccatg gcctccaggt tcttgtgggt    1080
gtcgtaaagg acgagggggtc ctacttcctg gtttatggcg cgccaggctt ctctaaggat    1140
aatgagagct tgatctctcg cgcggagttt ttggcaggcg tgcgcgtcgg cgtgcctcag    1200
```

```
gtttcagact tggcagccga ggccgtggtc ctccattata cggactggct gcacccggag    1260
gatcctgcca gacttcgcga agctctgtca gacgtggtcg gagaccataa tgtcgtgtgc    1320
cccgtggctc agttggctgg gcgcctcgca gcccaaggcg ccagggtata tgcgtacgtt    1380
ttcgagcacc gcgccagcac actctcatgg cctctttgga tgggcgtgcc ccacgggtat    1440
gaaatcgagt tcatattcgg catccctctg gatccatcca gaaactacac cgccgaagag    1500
aagatcttcg cccagagatt gatgagatac tgggccaact ttgctcggac cggtgaccct    1560
aacgagccca gagacccgaa ggctccccag tggcctcctt ataccgcggg tgcacagcag    1620
tacgtaagcc tggacctgag accactggag gtgcgacgcg gactgcgagc acaggcctgc    1680
gccttttgga atcggttcct ccccaagctg ttgtcagcca ccgcatccga agcccccgag    1740
cccaaatcta gtgacaaaac tcacacatgc ccaccgtgcc cagcacctga actcctgggg    1800
ggaccgtcag tcttcctctt ccccccaaaa cccaaggaca cctcatgat ctcccggacc     1860 cctgaggtca catgcgtggt ggtggacgtg agccacgaag accctgaggt caagttcaac    1920
tggtacgtgg acggcgtgga ggtgcataat gccaagacaa agccacggga ggagcagtac    1980
aacagcacct accgggtggt cagcgtcctc accgtcctgc accaggactg gctgaatggc    2040
aaggagtaca agtgcaaggt ctccaacaaa gccctcccag cccccatcga gaaaaccatc    2100
tccaaagcca aagggcagcc acgggaacca caggtttaca cctgccccc atcccgcgag    2160 gagatgacca gaaccaggt cagcctgacc tgcctggtca aaggcttcta tcccagcgac     2220
atcgccgtgg agtgggagag caatgggcag cccgagaaca actacaagac caccctcc     2280 gtgctggact ccgacggctc cttcttcctc tatagcaagc tcaccgtgga caagagcagg    2340
tggcagcagg ggaacgtctt ctcatgctcc gtgatgcacg aggctctgca caaccactac    2400
acccagaaga gcctctccct gtctccgggt aaatga                             2436
```

<210> SEQ ID NO 26
<211> LENGTH: 20
<212> TYPE: PRT
<213> ORGANISM: Artificial Sequence
<220> FEATURE:
<223> OTHER INFORMATION: Synthetic

<400> SEQUENCE: 26

```
Gly Gly Gly Ser Gly Gly Gly Ser Gly Gly Gly Ser Gly Gly Gly Ser
1               5                   10                  15

Gly Gly Gly Ser
            20
```